(12) United States Patent
Xu et al.

(10) Patent No.: US 9,133,207 B2
(45) Date of Patent: Sep. 15, 2015

(54) TETRANDRINE DERIVATIVES WITH SUBSTITUTED 5-CARBON, PREPARATION METHOD AND USE THEREOF

(75) Inventors: Rongzhen Xu, Zhejiang (CN); Frank Rong, Zhajiang (CN); Fuwen Xie, Fujian (CN); Hongxi Lai, Fujian (CN)

(73) Assignee: Hangzhou Bensheng Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/239,759

(22) PCT Filed: Aug. 20, 2012

(86) PCT No.: PCT/CN2012/080384
§ 371 (c)(1),
(2), (4) Date: Jun. 6, 2014

(87) PCT Pub. No.: WO2013/026383
PCT Pub. Date: Feb. 28, 2013

(65) Prior Publication Data
US 2014/0343047 A1  Nov. 20, 2014

(30) Foreign Application Priority Data
Aug. 19, 2011  (WO) ................ PCT/CN2011/078622

(51) Int. Cl.
*C07D 491/18* (2006.01)
*C07D 491/22* (2006.01)
*C07D 491/147* (2006.01)

(52) U.S. Cl.
CPC .......... *C07D 491/22* (2013.01); *C07D 491/147* (2013.01); *C07D 491/18* (2013.01)

(58) Field of Classification Search
CPC .................................................. C07D 491/18
USPC .......................................... 540/469; 514/279
See application file for complete search history.

(56) References Cited

PUBLICATIONS

Translation of International Search Report for PCT/CN2012/080384. Mailed Dec. 6, 2012. (4 pages).
Translation of the Written Opinion of the International Search Authority for PCT/CN2012/080834. Mailed Dec. 6, 2012. (7 pages).
Translation of the International Preliminary Report on Patentability for PCT/CN2012/080834. Mailed Feb. 25, 2014. (8 pages).

*Primary Examiner* — Bruck Kifle
(74) *Attorney, Agent, or Firm* — Lathrop & Gage LLP; Brian C. Trinque

(57) ABSTRACT

The present invention belongs to the field of natural medicine and pharmaceutical chemistry and specifically relates to novel 5-substituted tetrandrine derivatives of formula (I) and a pharmaceutically acceptable adduct, complex and salt thereof, to a process for the preparation of these compounds, pharmaceutical compositions containing such compounds and their use in preparing antineoplastic medicaments.

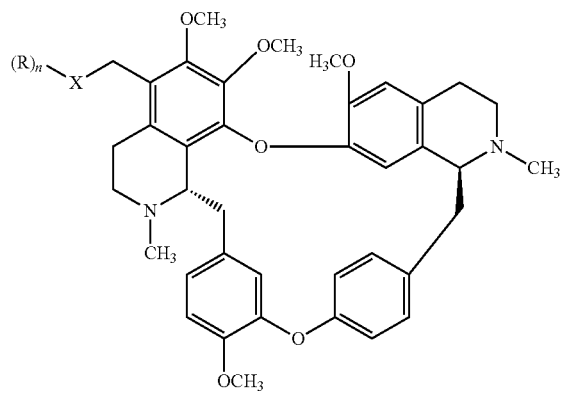

21 Claims, 5 Drawing Sheets

TETRANDRINE DERIVATIVES WITH SUBSTITUTED 5-CARBON, PREPARATION METHOD AND USE THEREOF

RELATED APPLICATIONS

This application is a 35 U.S.C. §371 filing of International Application No. PCT/CN2012/080384, filed Aug. 20, 2012; which claims priority to International Patent Application No. PCT/CN2011/078622, filed Aug. 19, 2011. The entire contents of each are incorporated herein by reference.

TECHNICAL FIELD

The present invention belongs to the field of natural medicine and pharmaceutical chemistry and relates to novel tetrandrine derivatives, in particular 5-substituted tetrandrine derivatives, to a process for the preparation of these compounds, compositions containing such compounds and their use in preparing antineoplastic medicaments.

BACKGROUND OF THE INVENTION

Tetrandrine, or TTD, with the chemical formula of 6,6',7,12-tetramethoxy-2,2'dimethylberbamine, is a bisbenzylisoquinoline alkaloid extracted from the root block of the Chinese herbal fangji. Tetrandrine has the effect of inhibiting the central nerves, as well as anti-inflammatory, analgesic and antipyretic effects. It directly expands peripheral blood vessels, leading to a prominent and persistent antihypertensive effect, and thus can find use in rheumatic pain, arthritis, neuralgia, muscle pain and various types of hypertension. Tetrandrine has negative inotropic effect, negative chronotropic effect and negative dromotropic effect on heart. Further, tetrandrine reduces myocardial consumption of oxygen, prolongs the myocardial refractory period and atrioventricular conduction, increases myocardial blood flow, reduces the total peripheral vascular resistance and brings down the blood pressure, during which the baroreflex-heart rate is not increasing. Due to the reduction of the afterload, the cardiac output may increase. These effects are all associated with the calcium antagonism thereof.

Therefore, tetrandrine and its derivatives and analogs are extensively studied around the world (Ji, Yubin et al., *Pharmacology of the Effective Components of Traditional Chinese Medicine and Their Applications*. Harbin: Heilongjiang Science and Technology Press, 1995; Su, J. Y. *Naunyn-Schmiedeberg's Arch Pharmacol.* 1993. 347:445-451; Wei, N.; Sun, H.; Wang, F. P. Cancer Chenother Pharmacol. 2011, 67:1017-1025; Rahman, A. U. Chem Pharm Bull, 2004, 52(7): 802; Wang, Jiwu et al., *Handbook of the Effective Components of Plant Drugs*. Beijing: People's Medical Publishing House, 1986; Knox, V. D. *Use of tetrandrine and its derivatives to treat malaria*. [P]. U.S. Pat. No. 5,025,020. 1991; Virginio, C.; Graziani, F.; Terstappen, G. C. Neuroscience Letters. 2005. 381:299-304; Karen, O. L.; Carolina, G. A.; Alexey, v. E.; Anatoly, K. Y. Org. Biomol. Chem. 2004, 2:1712-1718; Lin, Mubin et al., *Chemical Research on Tetrandrine-N-oxides*, Acta Chimica Sinica, 1984, 42(2):199-203; Tsutsumi, T.; Kobayashi, S.; Liu, Y. Y.; Kontani, H. Biol. Pharm. Bull. 26(3):313-317).

Tetrandrine and some derivatives or analogs thereof are as follows.

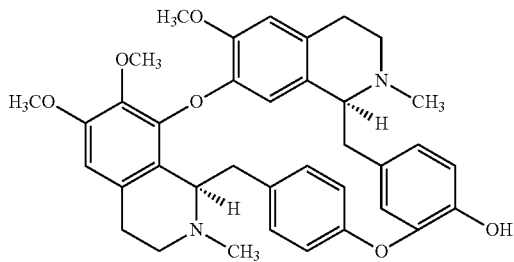

Oxyacanthine

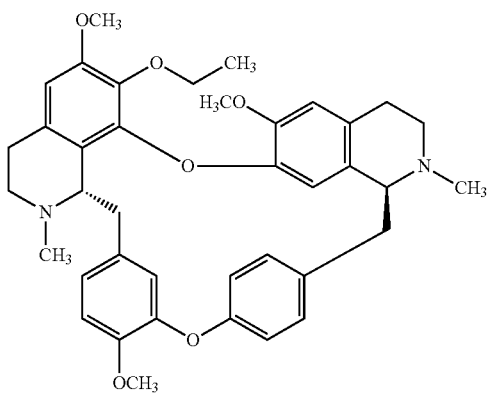

7-O-ethyl tetrandrine

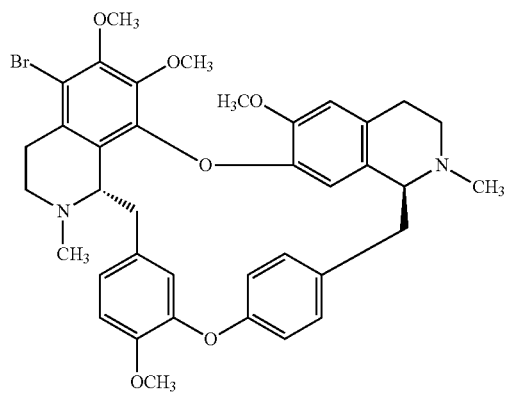

5-Bromotetrandrine

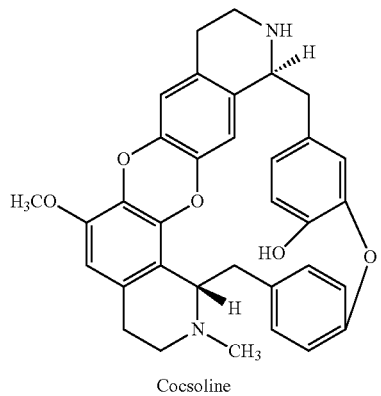

Cocsoline

CAS: 22226-73-9
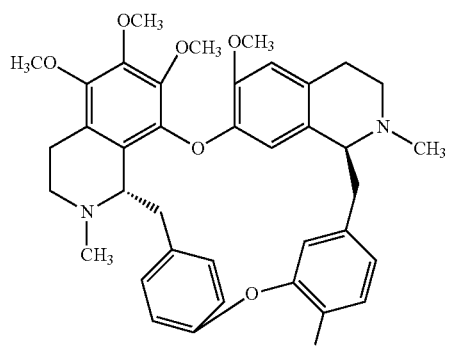
Thalrugosaminine
CAS: 6681-13-6
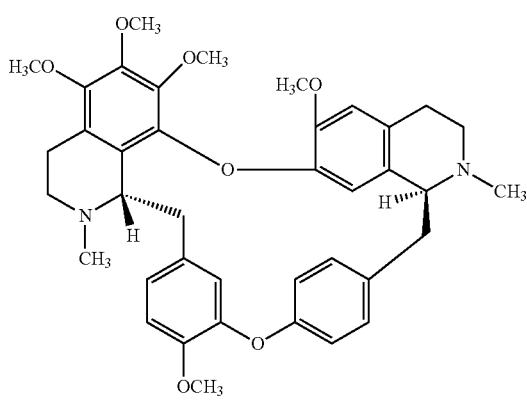
Hernandezine
CAS: 481-49-2
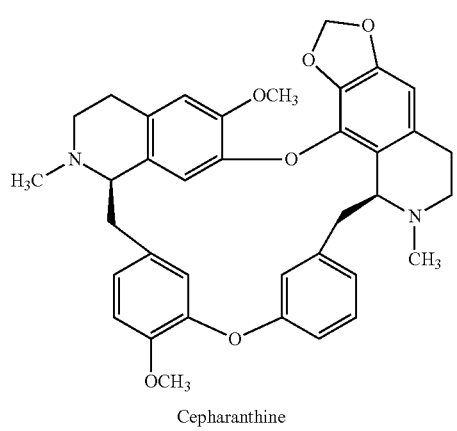
Cepharanthine
CAS: 518-94-5
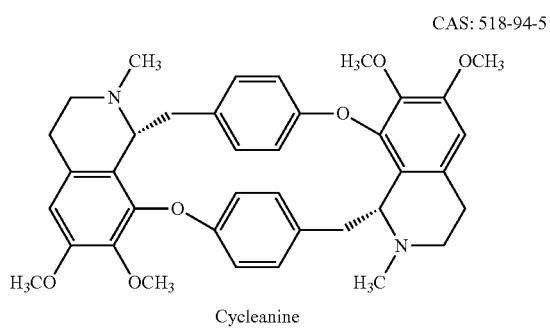
Cycleanine
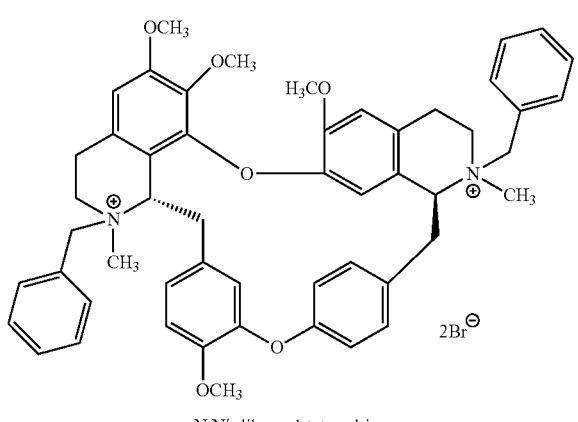
N,N'-dibenzyl-tetrandrine
CAS: 26279-88-9
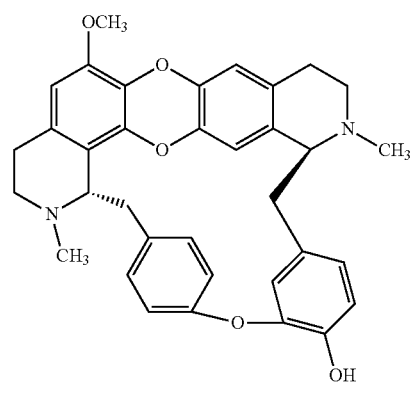
Cocsuline
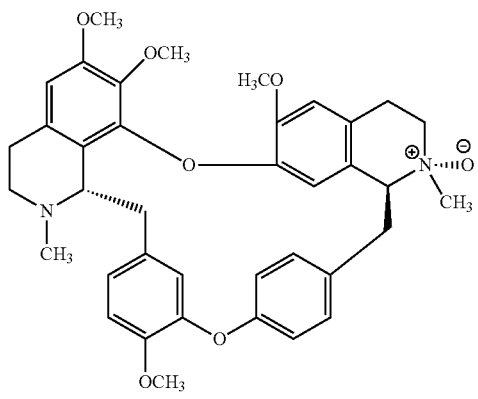
Tetrandrine 2'-N-α-oxide -continued

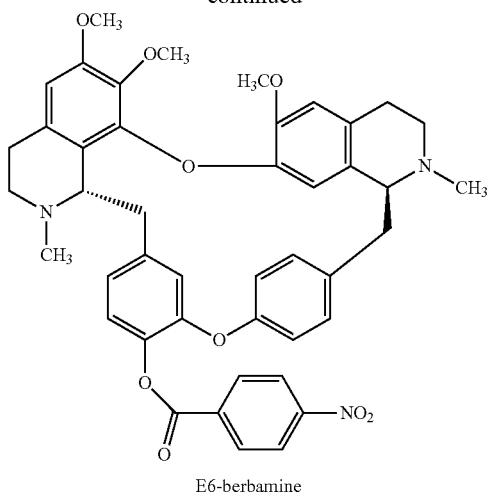

E6-berbamine

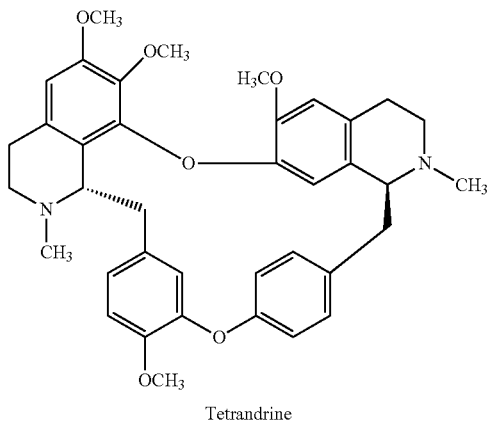

CAS: 518-34-3

Tetrandrine

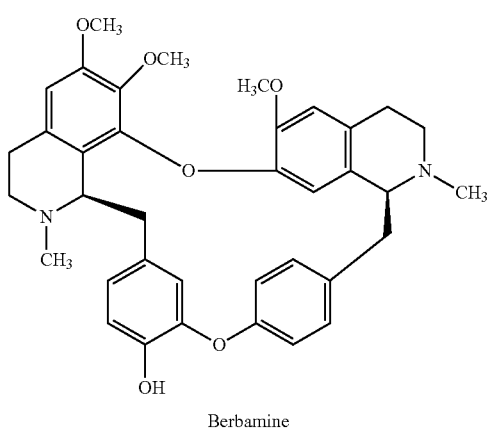

CAS: 478-61-5

Berbamine

-continued

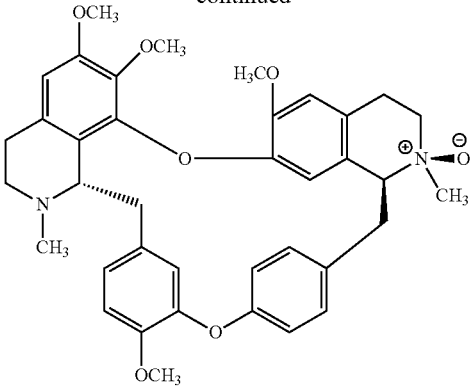

Tetrandrine 2'-N-β-oxide

Tetrandrine exhibits inhibition on the proliferation of cervical cancer HeLa cells. The studies use the MTT method to detect inhibition on the proliferation of the cervical cancer HeLa cell lines by tetrandrine in various concentrations and at different time. The cell apoptosis is detected by a flow cytometer and a confocal laser scanning microscopy. As is shown by the experiments, tetrandrine exhibits inhibition on proliferation of the cervical cancer HeLa cells, which has dependency on time and concentration. (Zhu Kexiu et al., *Qualitative and quantitative studies on tetrandrine-induced apoptosis of cervical cancer cells*, Journal of Xi'an Jiaotong University (Medical Sciences Edition), 2010, 31 (1), 102).

Tetrandrine can inhibit the proliferation of hepatoma cells. After tetrandrine acting on the hepatoma cells, reactive oxygen species (ROS) are generated within 2 hours, and the production of ROS increases significantly with the increase of dose. It is suggested that tetrandrine may generate reactive oxygen species by interfering with the mitochondrial function, which causes the cell lipid peroxidation, damages the DNA molecules or regulates related genes of apoptosis, thereby inhibiting the proliferation of hepatoma cells. (Jing Xubin et al., *Experimental studies on the tetrandrine-induced oxidative damage of hepatoma cells*, Journal of Clinical Hepatology, 2002, 18 (6), 366).

It is also reported that in vitro tetrandrine has obvious inhibitory effect on the growth of human neuroblastoma cell line TGW. Studies show that such inhibition gradually increases with the increase of dose, and such inhibition also increases apparently with prolonged inhibition time, showing a good dose-time correlation (Li Weisong et al., Journal of Clinical Pediatrics, *Experimental studies on tetrandrine-induced apoptosis of neuroblastoma cell line TDW*, 2006, 24 (6), 512).

In addition to the above effects of interferencing tumor cells, inhibiting their proliferation, inducing cell apoptosis and tumor growth, tetrandrine can also regulate the drug resistance of P-glycoprotein-mediated multidrug resistant cells and conduct the down regulation of the expression of the drug-resistant gene mdr1mRNA.

Some reports have proved by in vitro experiments that, after the application of tetrandrine in drug-resistant lung cancer, the drug-resistance index is reduced from 5.43 (while adriamycin is used) to 1.89, indicating that tetrandrine can reverse the drug resistance of drug-resistant lung cancer cell GLC-82/ADR to adriamycin. In addition, research is conducted on the reversal effect of tetrandrine on the human breast cancer multidrug resistant lines MCF-7/ADR, which has found out that 2.5 μmol/L tetrandrine can increase the adriamycin cytotoxicity on drug-resistant tumors by 20.4 times, indicating that tetrandrine has enormous potential in reversing the tumor ADR (Xu Meng et al., *Experimental* studies on the reversal of lung cancer chemotherapy resistance and resistance to apoptosis by tetrandrine, Practical Journal of cancer, 2003, 18(4): 347; Fu, L. W, et al. The multidrug resistance of tumour cells was reversed by tetrandrine in vitro and in xenografts derived from human breast adenocarcinoma MCF-7/adr cells. European Journal of Cancer, 2002, 38(3):418).

In addition, clinical experiments also substantiate that tetrandrine can promote the irradiated cancer cells to enter M phase from G2 phase, which shortens the time for the damage repair of radiotherapy cells, thereby achieving the purpose of radiosensitization.

Based on the experimental studies on tetrandrine increasing the radiosensitivity of breast cancer cells, some reports draw the conclusion that the cell cycle arrest induced after the irradiation is closely related to the p53 gene function. After cells receiving gamma irradiation, the Cyclin B1 and Cdc2 protein expression levels thereof are significantly lowered, and the mitotic index also decreases significantly, indicating that tetrandrine serves for removing G2-phase arrest, so as to significantly enhance the killing effect of gamma radiation on human breast cancer cells. In addition, some studies have also found that tetrandrine has radiosensitizing effect on stereo experiment of human esophageal cancer TE1 cells. Low concentrations of tetrandrine are chosen in some experiments to investigate the radiosensitizing effect, and it was found that the TE1 cell survival fraction exponentially declines with the increase of radiation dose, and that the maximum radiosensitization of 1.62 is reached at the drug concentration of 0.5 μg/mL, indicating that tetrandrine has certain radiosensitizing effect on esophageal cancer cells cultured in vitro, and the underlying mechanism may be that the G2+M phase cell arrest is removed by the increased expression of cyclin B1 (Tian Qingzhong et al., Study of potentiation of radiosensitivity by tetrandrine and its mechanism, Journal of Southeast University, 2005, 24 (4), 233; Yu Jingping et al., Radiosensitizing effect of tetrandrine in human esophageal carcinoma cells: A preliminary in vitro study, Chinese Journal of Radiation Oncology, 2010, 19 (6), 568).

It is apparent that tetrandrine medicaments of high activity are still needed in the market. Up to now, no reports have yet been seen on the synthesis and applications of tetrandrine derivatives modified and substituted on 5-carbon.

SUMMARY OF THE INVENTION

One object of the present invention is to provide novel 5-substituted tetrandrine derivatives characteristic of formula (I)

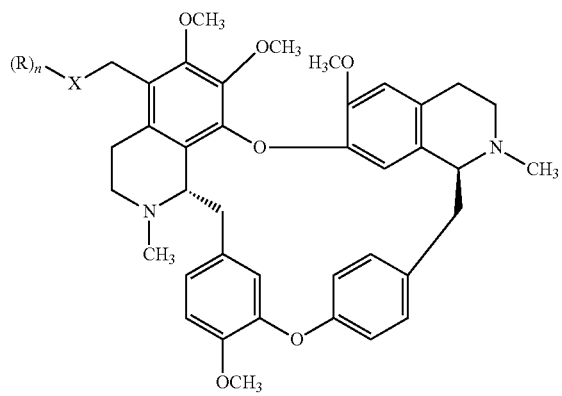

wherein

X is selected from oxygen, sulfur, nitrogen and carbonyloxy;

n is 1 or 2, wherein n=1 when X is oxygen or sulfur and n=2 when X is nitrogen;

R is independently selected from the group consisting of H, $C_1$-$C_6$ alkyl, $C_3$-$C_7$ cycloalkyl or cycloalkenyl, aryl or heteroaryl, aryl-$C_1$-$C_3$ alkyl, heteroaryl-$C_1$-$C_3$ alkyl, aryloxy-$C_1$-$C_3$ alkyl and heteroaryloxy-$C_1$-$C_3$ alkyl; when X is carbonyloxy, R can also be $C_1$-$C_6$ alkoxy or $C_1$-$C_6$ alkylthio; when X is nitrogen, the two R group together with the nitrogen atom to which they are connected can form non-aromatic nitrogen-containing heterocyclyl or nitrogen-containing heteroaryl; the aforementioned groups, except for H, are optionally substituted with a substituent selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said cycloalkyl, cycloalkenyl, aryl, heteroaryl, nitrogen-containing heterocyclyl or nitrogen-containing heteroaryl are optionally substituted with a substituent selected from $C_1$-$C_6$ alkyl, hydroxyl $C_1$-$C_6$ alkyl, thiol $C_1$-$C_6$ alkyl and phenyl;

or a pharmaceutically acceptable adduct, complex or salt thereof.

According to an embodiment of the present invention, the 5-substituted tetrandrine derivative or a pharmaceutically acceptable salt thereof of the present invention is represented by formula (I-b) (embodiment of formula (I) in which X is carbonyloxy)

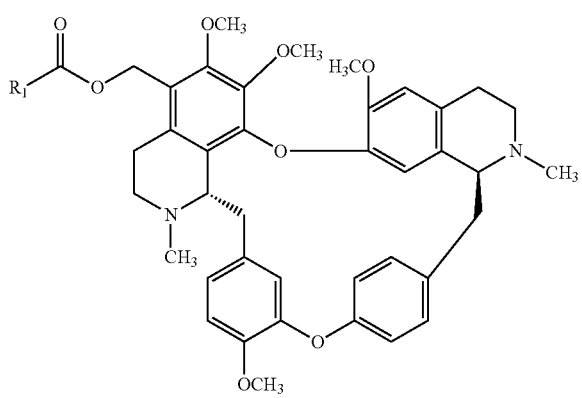

wherein $R_1$ is selected from H, $C_1$-$C_6$ alkyl, aryl or heteroaryl, $C_1$-$C_6$ alkoxy or $C_1$-$C_6$ alkylthio, which, except for H, are optionally substituted with substituents selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said aryl and heteroaryl are optionally substituted with a substituent selected from $C_1$-$C_6$ alkyl, hydroxyl $C_1$-$C_6$ alkyl and thiol $C_1$-$C_6$ alkyl.

According to another embodiment of the present invention, the 5-substituted tetrandrine derivative or a pharmaceutically acceptable salt thereof of the present invention is represented by formula (I-c) (embodiment of formula (I) in which X is nitrogen)

I-c

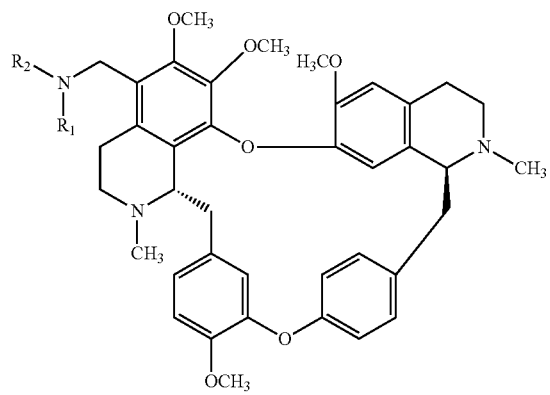

I-e

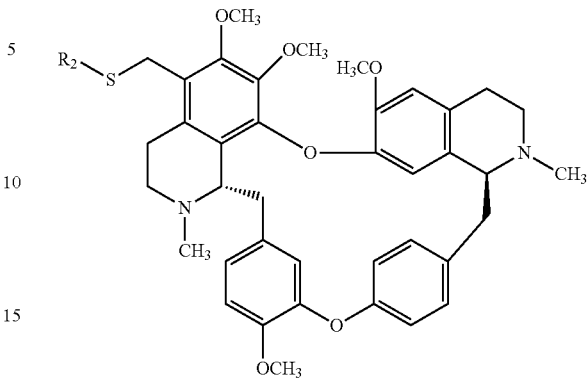

wherein $R_2$ is selected from $C_1$-$C_6$ alkyl, aryl, $C_3$-$C_7$ cycloalkyl or cycloalkenyl, aryl-$C_1$-$C_3$ alkyl, heteroaryl-$C_1$-$C_3$ alkyl, heterocyclyl-$C_1$-$C_3$ alkyl, aryloxy-$C_1$-$C_3$ alkyl or heteroaryloxy-$C_1$-$C_3$ alkyl, which are optionally substituted with a substituent selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said cycloalkyl, cycloalkenyl, aryl and heteroaryl are optionally substituted with a substituent selected from $C_1$-$C_6$ alkyl, hydroxyl $C_1$-$C_6$ alkyl or thiol $C_1$-$C_6$ alkyl.

wherein $R_1$ and $R_2$ are independently selected from H, $C_1$-$C_6$ alkyl, $C_3$-$C_7$ cycloalkyl or cycloalkenyl, aryl-$C_1$-$C_3$ alkyl, heteroaryl-$C_1$-$C_3$ alkyl, aryloxy-$C_1$-$C_3$ alkyl or heteroaryloxy-$C_1$-$C_3$ alkyl, or $R_1$ and $R_2$ together with the nitrogen atom to which they are connected form non-aromatic nitrogen-containing heterocyclyl or nitrogen-containing heteroaryl; the aforementioned radicals, except for H, are optionally substituted with substituents selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said cycloalkyl, cycloalkenyl, aryl, heteroaryl, nitrogen-containing heterocyclyl or nitrogen-containing heteroaryl are optionally substituted with a substituent selected from $C_1$-$C_6$ alkyl, hydroxyl $C_1$-$C_6$ alkyl, thiol $C_1$-$C_6$ alkyl and phenyl.

According to another embodiment of the present invention, the 5-substituted tetrandrine derivative or a pharmaceutically acceptable salt thereof of the present invention is represented by formula (I-d) or (I-e) (embodiments of formula (I) in which X is oxygen or sulfur), The second object of the present invention is to provide a process for preparing the 5-substituted tetrandrine derivative of formula (I) of the present invention:

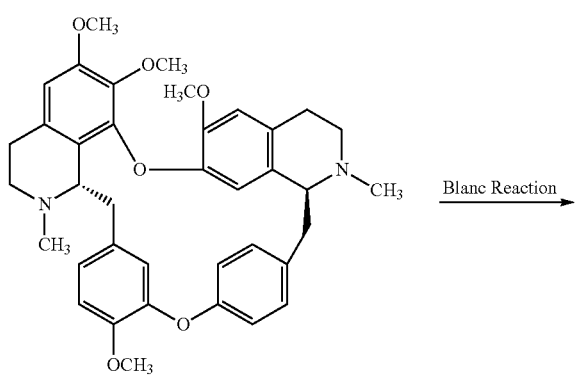

Tetrandrine

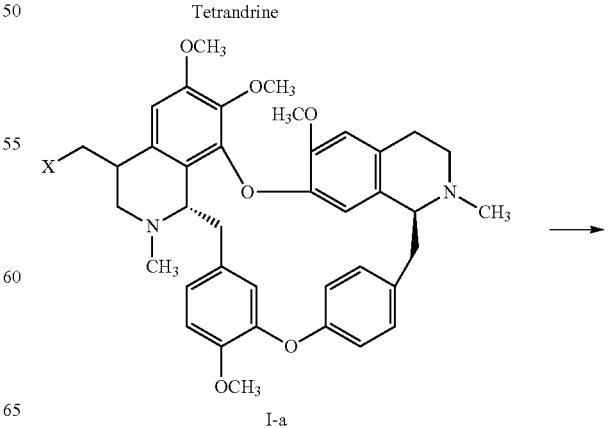

I-a

I-d

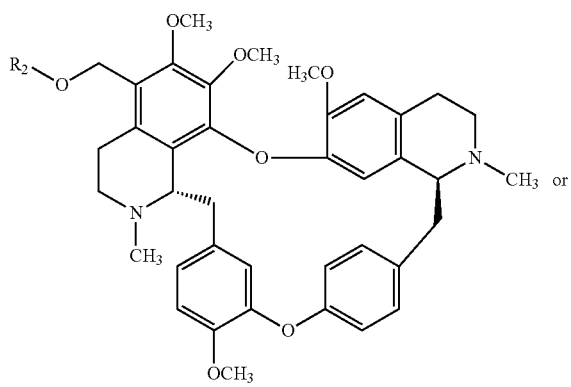

or

-continued

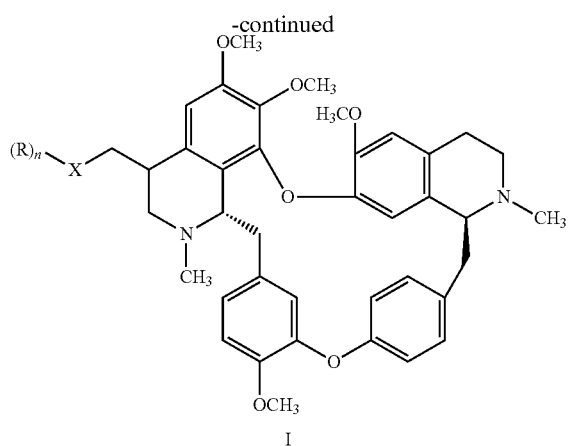

I

The 5-substituted tetrandrine derivative of formula (I) of the present invention can be prepared in a two-step reaction according to the above scheme. In the reaction, tetrandrine and formaldehyde are subjected to Blanc Reaction of chloromethylation in the presence of hydrochloric acid and zinc chloride to produce 5-chloromethyl-tetrandrine (I-a, X=Cl), and then said 5-chloromethyltetrandrine (I-a, X=Cl) are subjected to substitution reaction or condensation reaction with an appropriate small organic molecule to produce a 5-substituted tetrandrine derivative of formula (I), wherein R and X are defined as in above formula (I).

The third object of the present invention is to provide a pharmaceutical composition comprising the compound of the present invention. Said pharmaceutical composition comprises at least one compound of the present invention and optionally a pharmaceutically acceptable excipient.

The fourth object of the present invention is to provide the use of the compound of the present invention or a pharmaceutical composition comprising said compound in the manufacture of a medicament, in particular an antitumor medicament. Correspondingly, the present invention provides a method for treating a subject suffering from tumor, comprising administering to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor, prostate cancer and the like.

The present invention also relates to the compounds of the present invention used for treating a tumor.

DETAILED DESCRIPTION OF THE INVENTION

Figure 1:
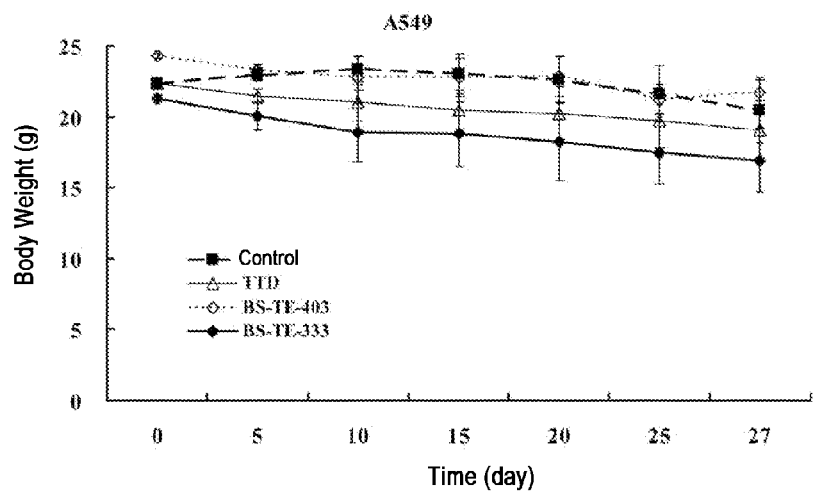
FIG. 1: the dynamic change of the effect of BS-TE-403 and BS-TE-333 on the body weight of nude mice.

The present invention provides a novel tetrandrine derivative with antitumor activity, in particular a 5-substituted tetrandrine derivative.

The present invention relates to a 5-substituted tetrandrine derivative of formula (I) or a pharmaceutically acceptable adduct, complex or salt thereof,

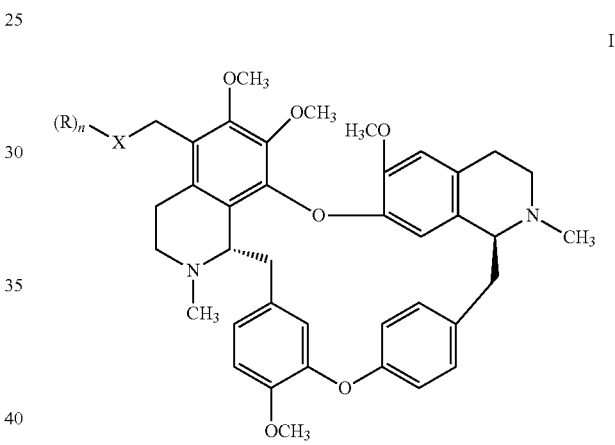

I wherein
X is selected from oxygen, sulfur, nitrogen and carbonyloxy;
n is 1 or 2, wherein n=1 when X is oxygen or sulfur and n=2 when X is nitrogen;
R is independently selected from H, $C_1$-$C_6$ alkyl, $C_3$-$C_7$ cycloalkyl or cycloalkenyl, aryl or heteroaryl, aryl-$C_1$-$C_3$ alkyl, heteroaryl-$C_1$-$C_3$ alkyl, aryloxy-$C_1$-$C_3$ alkyl or heteroaryloxy-$C_1$-$C_3$ alkyl; when X is carbonyloxy, R can also be $C_1$-$C_6$ alkoxy or $C_1$-$C_6$ alkylthio; when X is nitrogen, the two R groups together with the nitrogen atom to which they are connected can form non-aromatic nitrogen-containing heterocyclyl or nitrogen-containing heteroaryl; the aforementioned radicals, except for H, are optionally substituted with a substituent selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said cycloalkyl, cycloalkenyl, aryl, heteroaryl, nitrogen-containing heterocyclyl or nitrogen-containing heteroaryl are optionally substituted with a substituent selected from $C_1$-$C_6$ alkyl, hydroxyl $C_1$-$C_6$ alkyl, thiol $C_1$-$C_6$ alkyl and phenyl.

When X is carbonyloxy in formula (I), the 5-substituted tetrandrine derivative or a pharmaceutically acceptable salt thereof of the present invention is represented by formula (I-b)

I-b

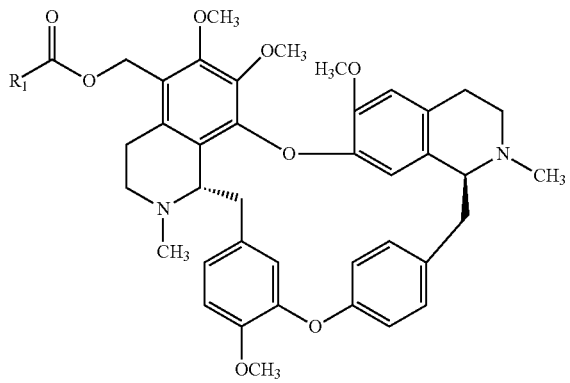

wherein $R_1$ is selected from H, $C_1$-$C_6$ alkyl, aryl or heteroaryl, $C_1$-$C_6$ alkoxy or $C_1$-$C_6$ alkylthio, which, except for H, are optionally substituted with a substituent selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said aryl and heteroaryl are optionally substituted with a substituent selected from $C_1$-$C_6$ alkyl, hydroxyl $C_1$-$C_6$ alkyl and thiol $C_1$-$C_6$ alkyl.

Preferably, in the 5-substituted tetrandrine derivative or a pharmaceutically acceptable salt thereof of formula (I-b), $R_1$ is selected from $C_1$-$C_6$ alkyl, aryl and heteroaryl.

More preferably, in the 5-substituted tetrandrine derivative or a pharmaceutically acceptable salt thereof of formula (I-b), $R_1$ is selected from methyl, ethyl, propyl, isopropyl, phenyl, dimethylaminophenyl, furyl, thienyl, methylthienyl and the like.

When X is nitrogen in formula (I), the 5-substituted tetrandrine derivative or a pharmaceutically acceptable salt thereof of the present invention is represented by formula (I-c)

I-c

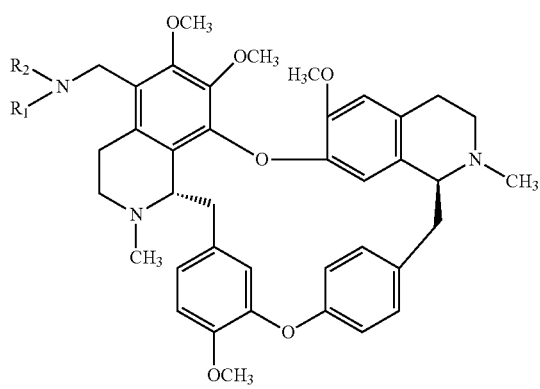

wherein $R_1$ and $R_2$ are independently selected from H, $C_1$-$C_6$ alkyl, $C_3$-$C_7$ cycloalkyl or cycloalkenyl, aryl-$C_1$-$C_3$ alkyl, heteroaryl-$C_1$-$C_3$ alkyl, aryloxy-$C_1$-$C_3$ alkyl, heteroaryloxy-$C_1$-$C_3$ alkyl, or $R_1$ and $R_2$, together with the nitrogen atom to which they are connected, form non-aromatic nitrogen-containing heterocyclyl or nitrogen-containing heteroaryl; the aforementioned radicals, except for H, are optionally substituted with a substituent selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said cycloalkyl, cycloalkenyl, aryl, heteroaryl, nitrogen-containing heterocyclyl or nitrogen-containing heteroaryl are optionally substituted with a substituent selected from $C_1$-$C_6$ alkyl, hydroxyl $C_1$-$C_6$ alkyl, thiol $C_1$-$C_6$ alkyl and phenyl.

Preferably, in the 5-substituted tetrandrine derivative or a pharmaceutically acceptable salt thereof of formula (I-c), $R_1$ and $R_2$ are independently selected from H, $C_1$-$C_6$ alkyl, $C_3$-$C_7$ cycloalkyl, aryl-$C_1$-$C_3$ alkyl, heteroaryl-$C_1$-$C_3$ alkyl, or $R_1$ and $R_2$ together with the nitrogen atom to which they are connected form non-aromatic nitrogen-containing heterocyclyl or nitrogen-containing heteroaryl.

Preferably, in the 5-substituted tetrandrine derivative or a pharmaceutically acceptable salt thereof of formula (I-c), the aforementioned radicals, except for H, are substituted with a substituent selected from the group consisting of amino, $C_1$-$C_6$ alkyl amino, nitro, cyano, hydroxyl, $C_1$-$C_6$ alkoxy; said cycloalkyl, cycloalkenyl, aryl, heteroaryl, nitrogen-containing heterocyclyl or nitrogen-containing heteroaryl are substituted with a substituent selected from $C_1$-$C_6$ alkyl, hydroxyl $C_1$-$C_6$ alkyl and phenyl.

Preferably, in the 5-substituted tetrandrine derivative or a pharmaceutically acceptable salt thereof of formula (I-c), $R_1$ and $R_2$ are independently selected from H, $C_1$-$C_6$ alkyl optionally substituted with hydroxyl or $C_1$-$C_6$ alkoxy, $C_3$-$C_7$ cycloalkyl optionally substituted with hydroxyl or $C_1$-$C_6$ alkoxy, aryl-$C_1$-$C_3$ alkyl optionally substituted on the aryl with $C_1$-$C_6$ alkyl, heteroaryl-$C_1$-$C_3$ alkyl optionally substituted on the heteroaryl with $C_1$-$C_6$ alkyl, or $R_1$ and $R_2$ together with the nitrogen atom to which they are connected form non-aromatic nitrogen-containing heterocyclyl or nitrogen-containing heteroaryl; said non-aromatic nitrogen-containing heterocyclyl is optionally substituted with a substituent selected from hydroxyl, hydroxyl $C_1$-$C_6$ alkyl, amino, $C_1$-$C_6$ alkyl amino, $C_1$-$C_6$ alkyl, cyano, nitro and phenyl.

Preferably, in the 5-substituted tetrandrine derivative or a pharmaceutically acceptable salt thereof of formula (I-c), $R_1$ and $R_2$ are independently selected from H, $C_1$-$C_3$ alkyl substituted with $C_1$-$C_3$ alkoxy, $C_3$-$C_6$ cycloalkyl, arylmethyl, aryl(methyl)methyl, heteroarylmethyl, or $R_1$ and $R_2$ together with the nitrogen atom to which they are connected form non-aromatic nitrogen-containing heterocyclyl; said non-aromatic nitrogen-containing heterocyclyl is optionally substituted with a substituent selected from hydroxyl, hydroxyl $C_1$-$C_6$ alkyl, amino, $C_1$-$C_6$ alkyl amino, $C_1$-$C_6$ alkyl, cyano, nitro and phenyl.

Preferably, in the 5-substituted tetrandrine derivative or a pharmaceutically acceptable salt thereof of formula (I-c), said non-aromatic nitrogen-containing heterocyclyl is a 5-7 membered ring, optionally comprising 1-2 heteroatoms selected from nitrogen, oxygen and sulfur in addition to the nitrogen atom connecting to $R_1$ and $R_2$; more preferably, said non-aromatic nitrogen-containing heterocyclyl is pyrrolidinyl, pyrrolinyl, piperidyl, piperazinyl, morpholinyl, thiomorpholinyl or diazacycloheptyl.

Preferably, in the 5-substituted tetrandrine derivative or a pharmaceutically acceptable salt thereof of formula (I-c), the aryl in those groups containing aryl is preferably phenyl; the heteroaryl in those groups containing heteroaryl is preferably a pyridyl optionally substituted with $C_1$-$C_3$ alkyl, an furyl optionally substituted with $C_1$-$C_3$ alkyl, or a thienyl optionally substituted with $C_1$-$C_3$ alkyl.

When X is oxygen or sulfur in formula (I), the 5-substituted tetrandrine derivative or a pharmaceutically acceptable salt thereof of the present invention is represented by formula (I-d) or (I-e)

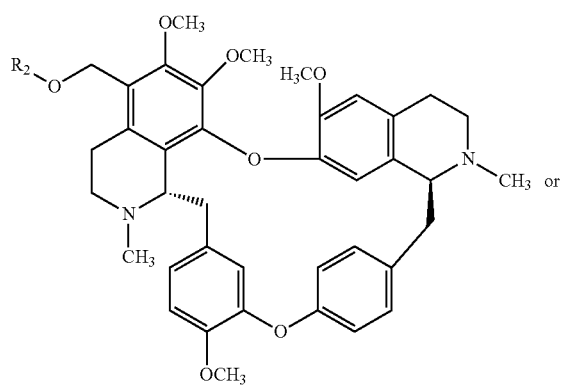

I-d

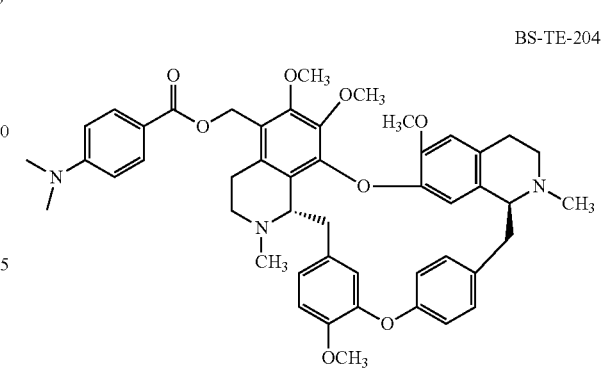

BS-TE-204

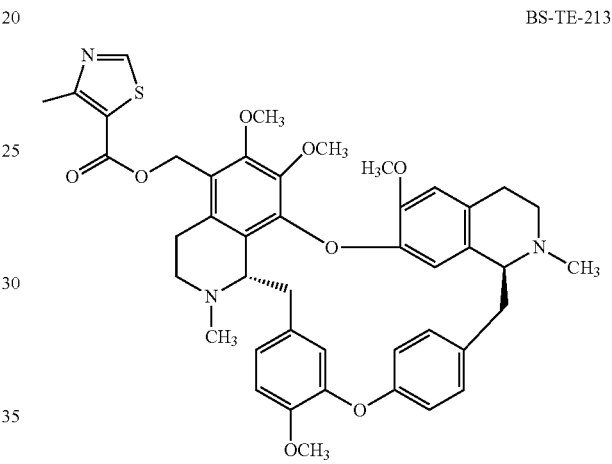

BS-TE-213

I-e

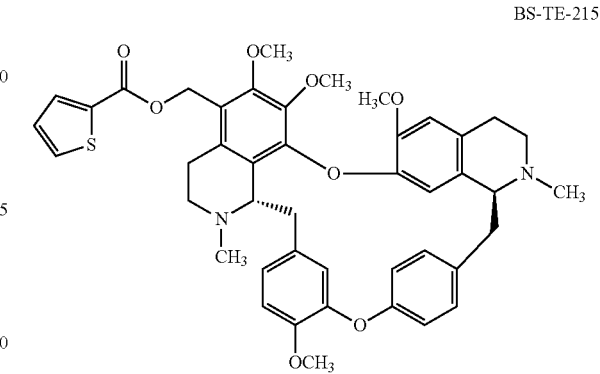

BS-TE-215

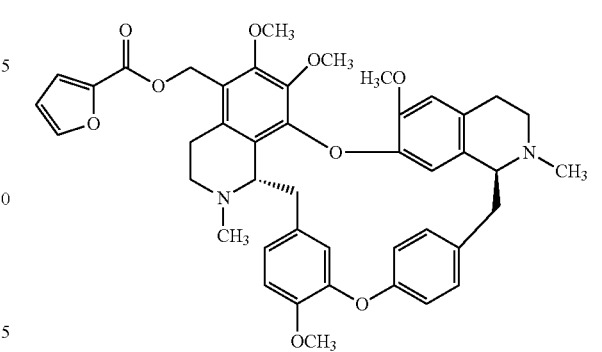

BS-TE-216 wherein $R_2$ is selected from $C_1$-$C_6$ alkyl, aryl, $C_3$-$C_7$ cycloalkyl or cycloalkenyl, aryl-$C_1$-$C_3$ alkyl, heteroaryl-$C_1$-$C_3$ alkyl, heterocyclyl-$C_1$-$C_3$ alkyl, aryloxy-$C_1$-$C_3$ alkyl or heteroaryloxy-$C_1$-$C_3$ alkyl, which are optionally substituted with a substituent selected from the group consisting of halogen, amino, $C_1$-$C_6$ alkyl amino, nitro, cyano, hydroxyl, $C_1$-$C_6$ alkoxy, thiol and $C_1$-$C_6$ alkylthio; said cycloalkyl, cycloalkenyl, aryl and heteroaryl are optionally substituted with a substituent selected from $C_1$-$C_6$ alkyl, hydroxyl $C_1$-$C_6$ alkyl and thiol $C_1$-$C_6$ alkyl.

Preferably, in the 5-substituted tetrandrine derivative or a pharmaceutically acceptable salt thereof of formula (I-d) or (I-e), $R_2$ is selected from aryl-$C_1$-$C_3$ alkyl, heteroaryl-$C_1$-$C_3$ alkyl, aryloxy-$C_1$-$C_3$ alkyl and heteroaryloxy-$C_1$-$C_3$ alkyl.

More preferably, in the 5-substituted tetrandrine derivative or a pharmaceutically acceptable salt thereof of formula (I-d) or (I-e), the aryl in those groups containing aryl or the heteroaryl in those groups containing heteroaryl is substituted with a substituent selected from halogen and $C_1$-$C_6$ alkoxy.

More preferably, in the 5-substituted tetrandrine derivative or a pharmaceutically acceptable salt thereof of formula (I-d) or (I-e), the aryl in those groups containing aryl is preferably phenyl and the heteroaryl in those groups containing heteroaryl is preferably pyridyl, imidazolyl or thienyl.

Some of the 5-substituted tetrandrine derivatives of the present invention are shown below. These examples are only intended to further illustrate the present invention but not to make any restriction over the scope of the present invention.

-continued
BS-TE-223
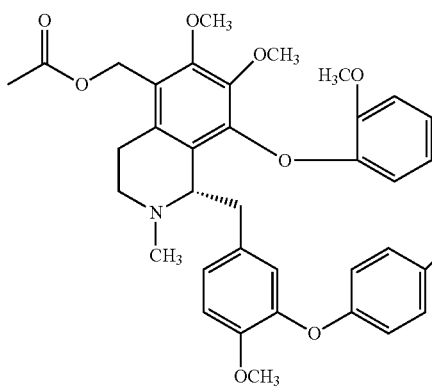
BS-TE-224
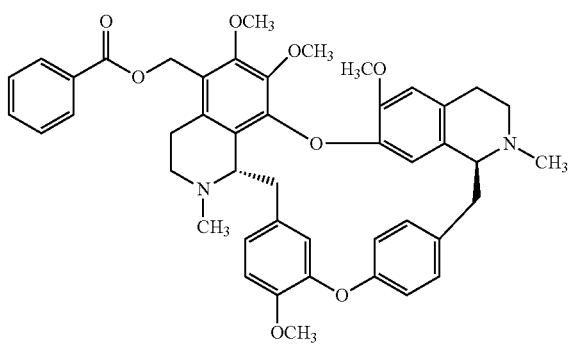
BS-TE-301
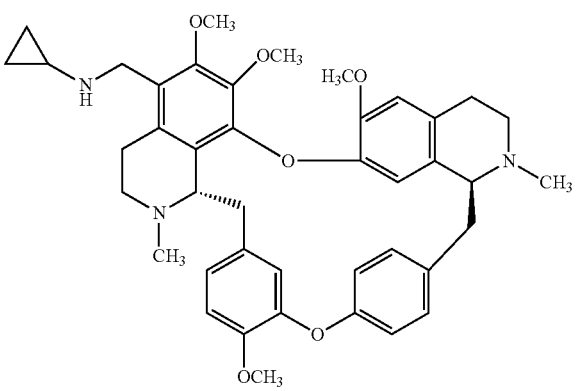
BS-TE-305
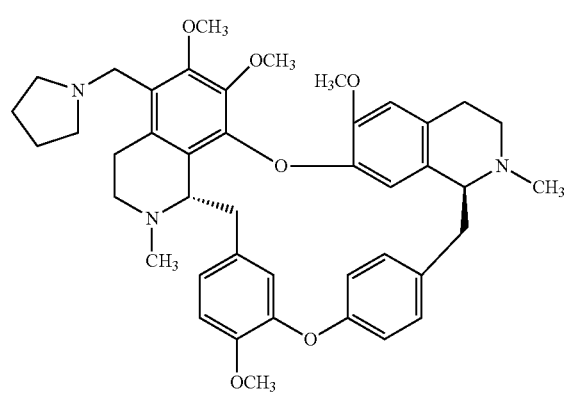
-continued
BS-TE-307
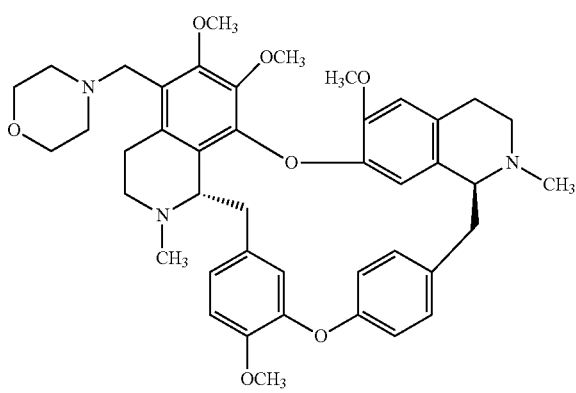
BS-TE-308
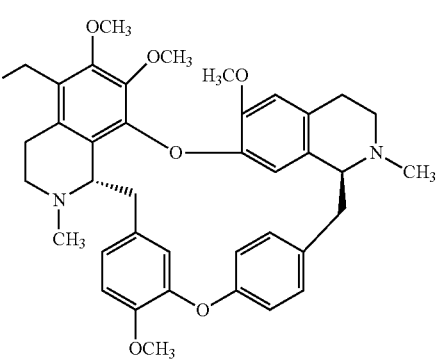
BS-TE-311
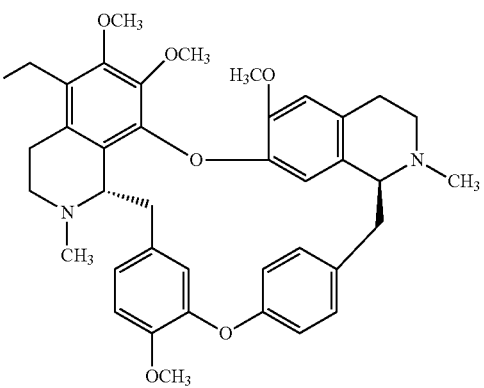
BS-TE-315
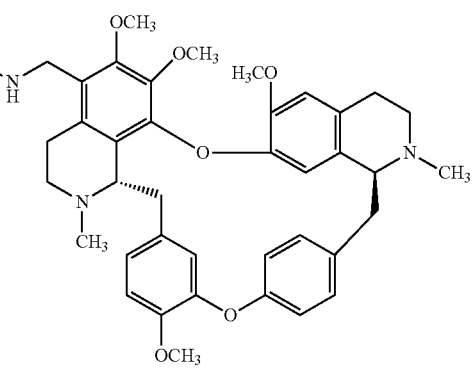

BS-TE-317
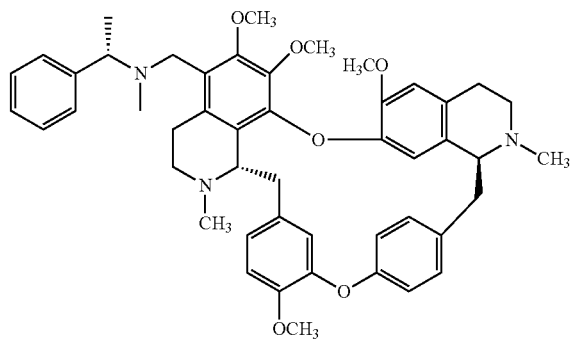
BS-TE-323
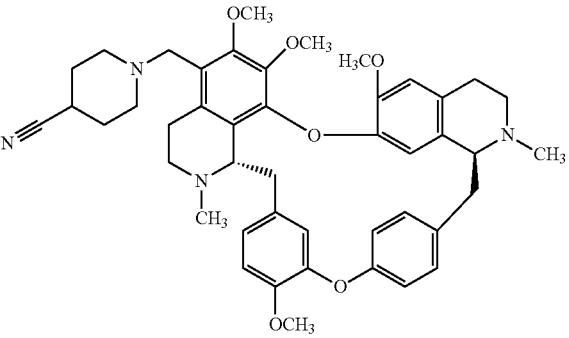
BS-TE-320
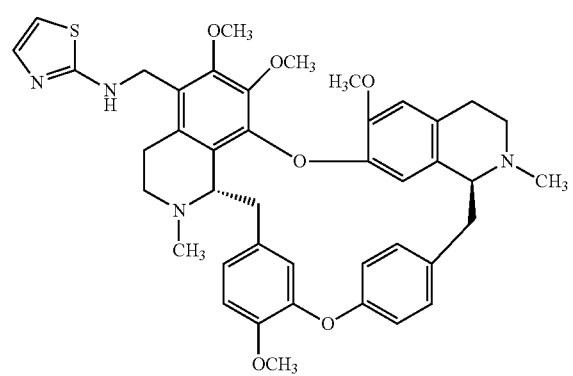
BS-TE-326
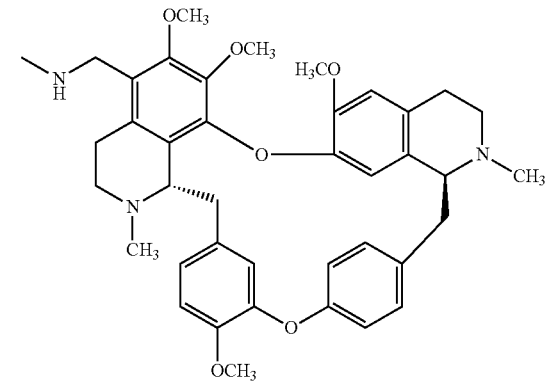
BS-TE-321
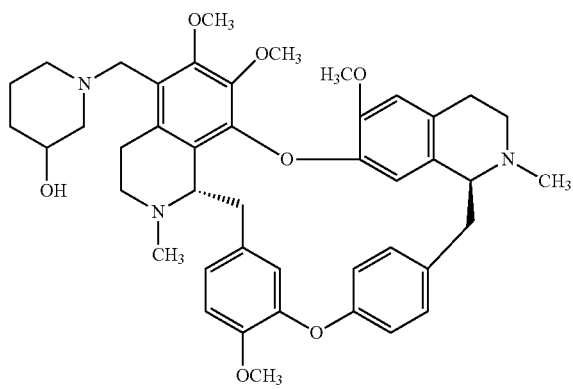
BS-TE-328
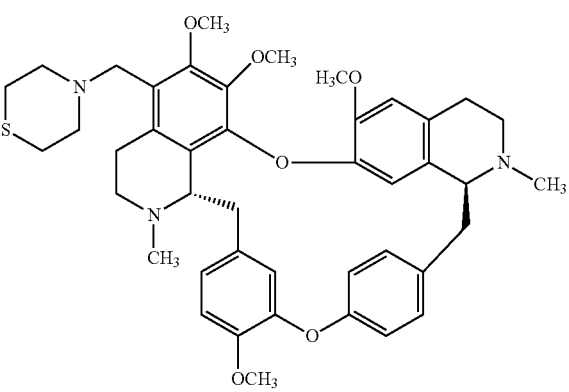
BS-TE-322
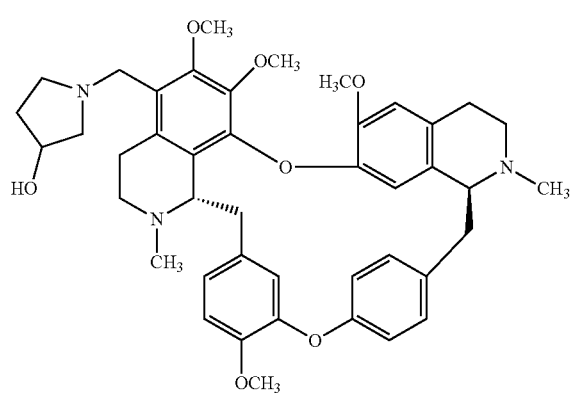
BS-TE-329

BS-TE-330
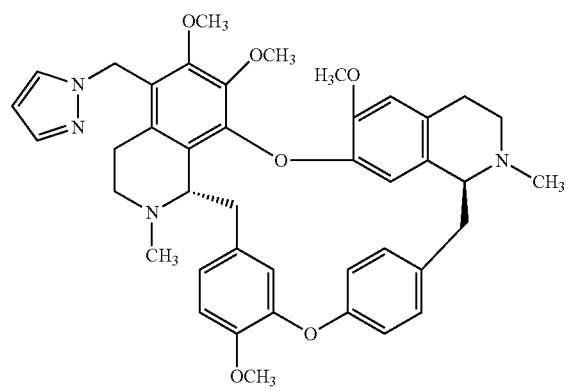
BS-TE-333
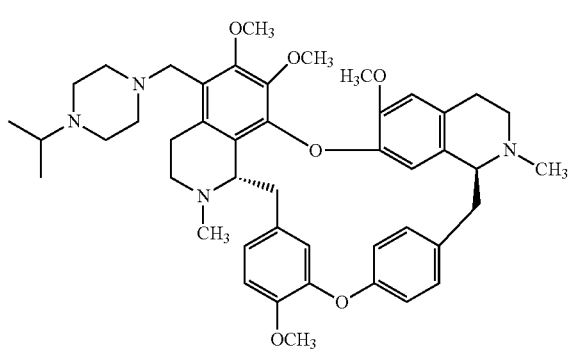
BS-TE-334
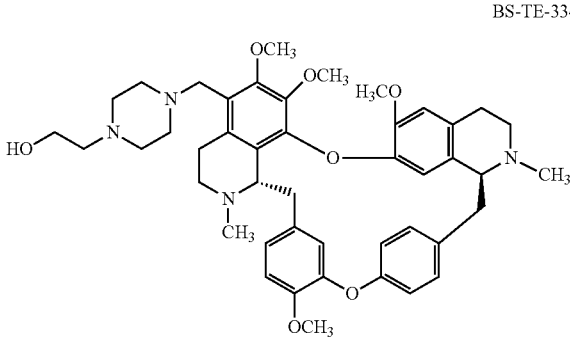
BS-TE-340
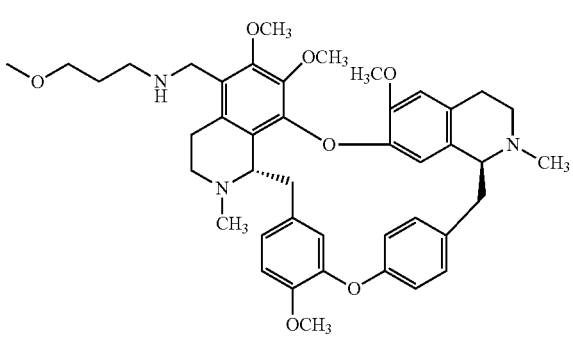
BS-TE-341
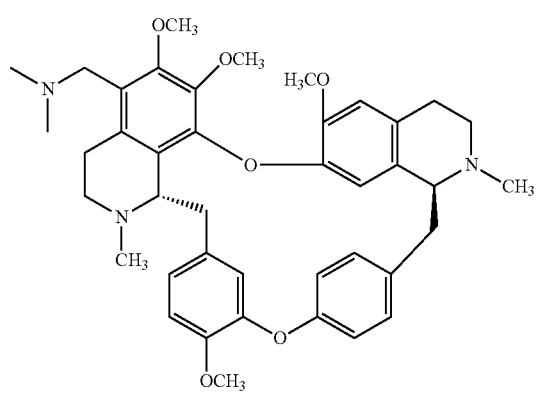
BS-TE-342
BS-TE-343
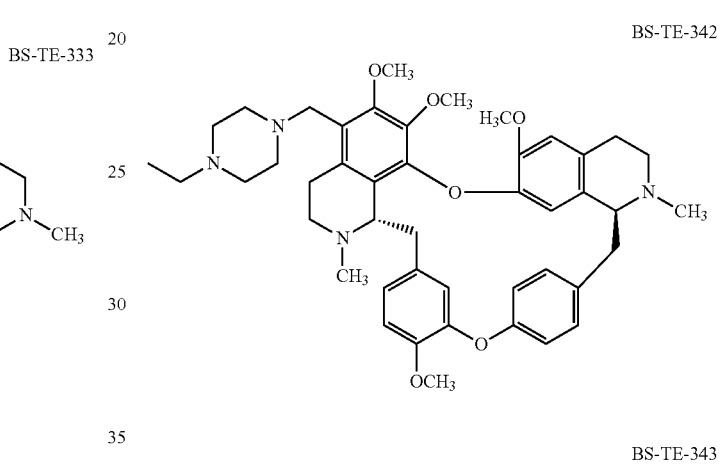
BS-TE-346
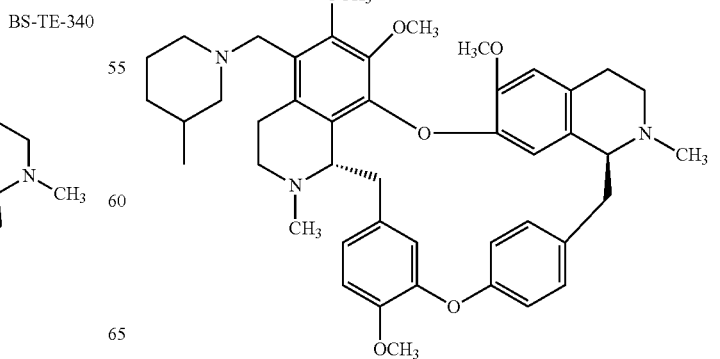

BS-TE-348
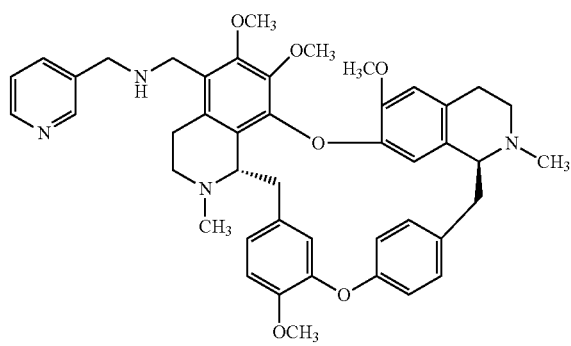
BS-TE-350
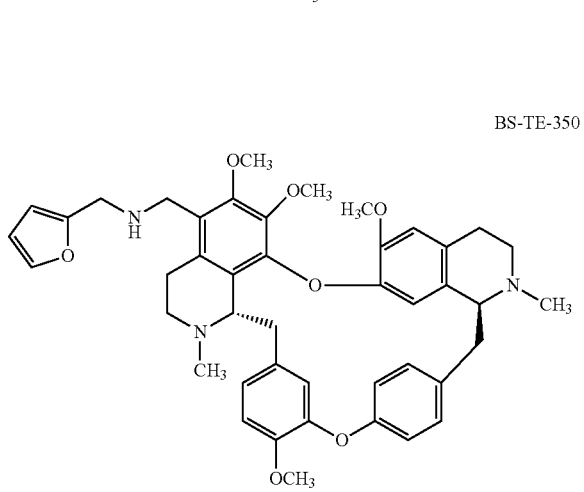
BS-TE-351
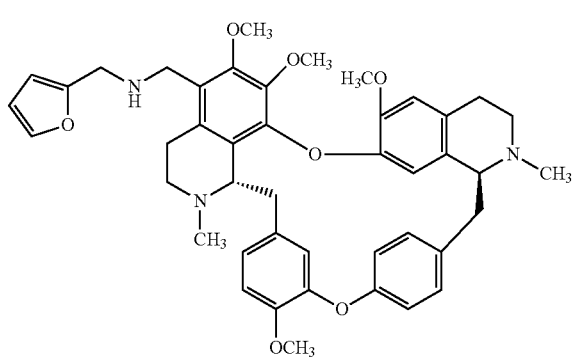
BS-TE-352
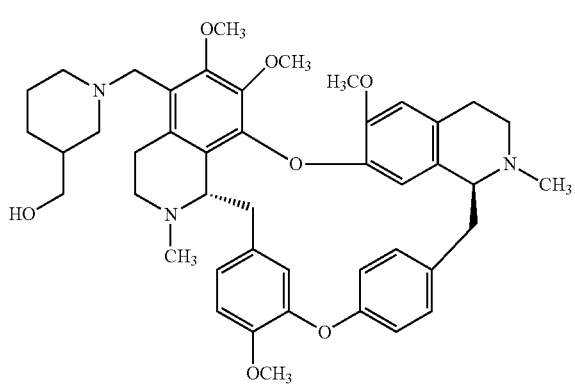
BS-TE-354
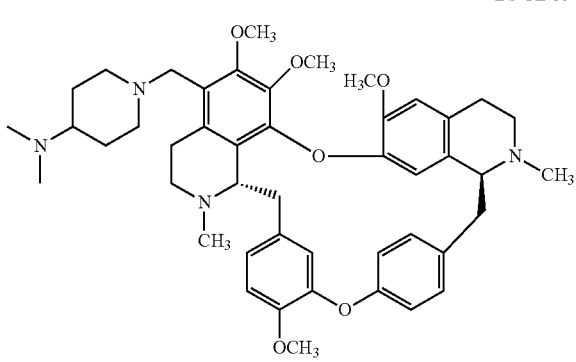
BS-TE-355
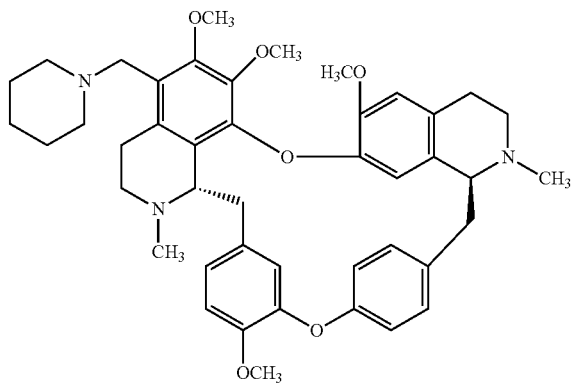
BS-TE-356
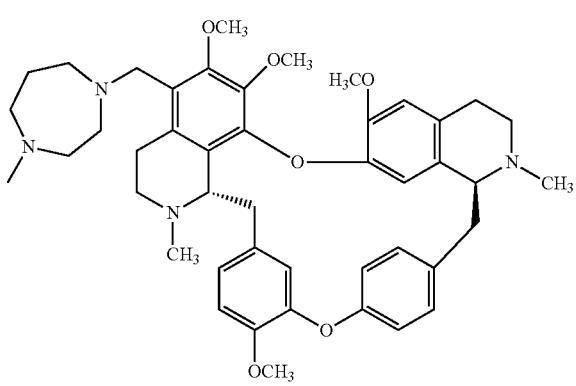
BS-TE-358
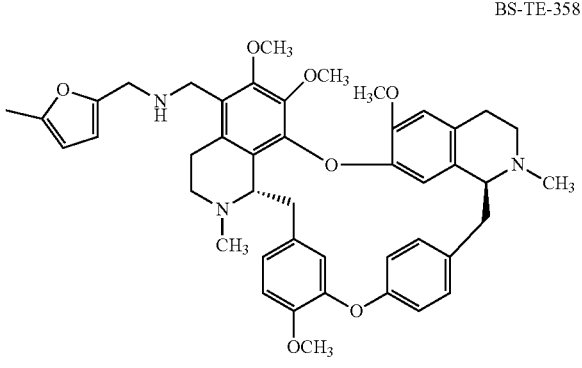

BS-TE-359
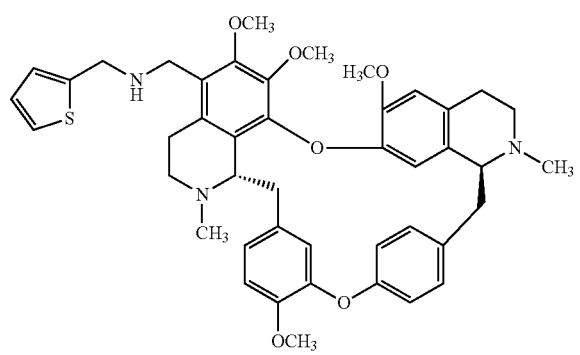
BS-TE-403
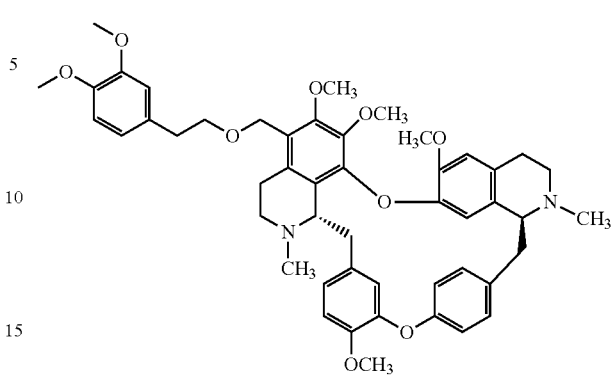
BS-TE-360
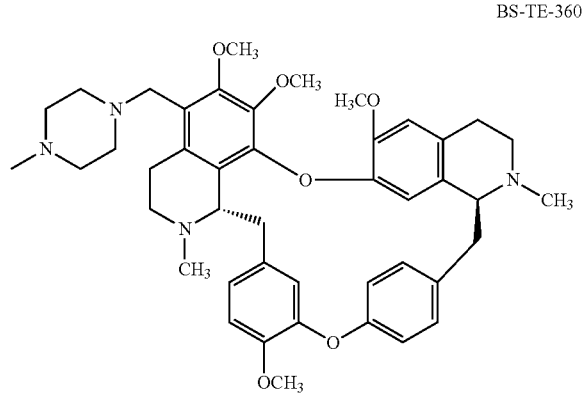
BS-TE-406
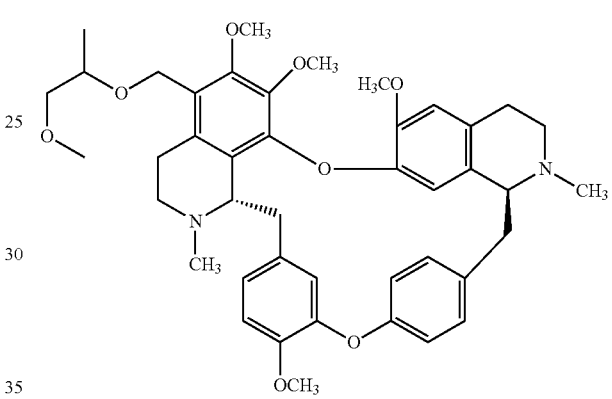
BS-TE-361
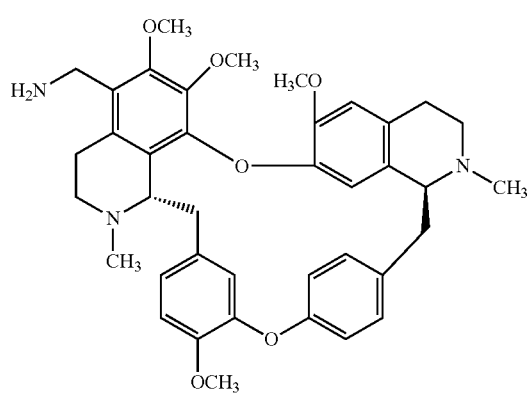
BS-TE-408
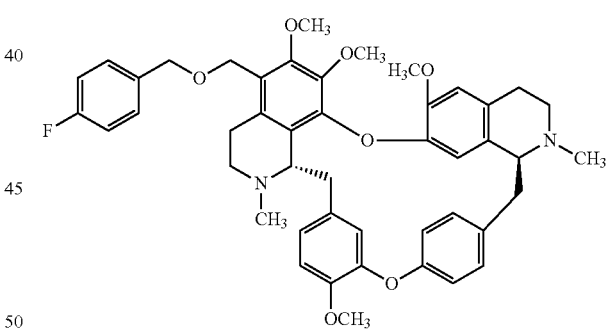
BS-TE-402
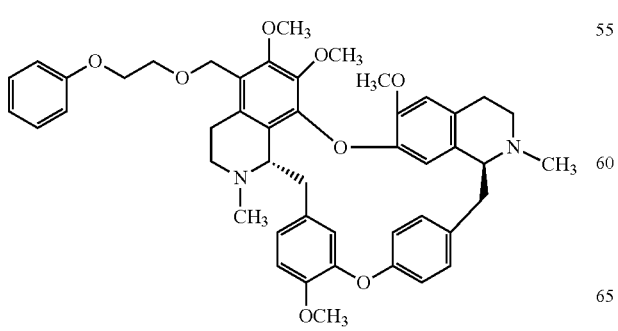
BS-TE-411
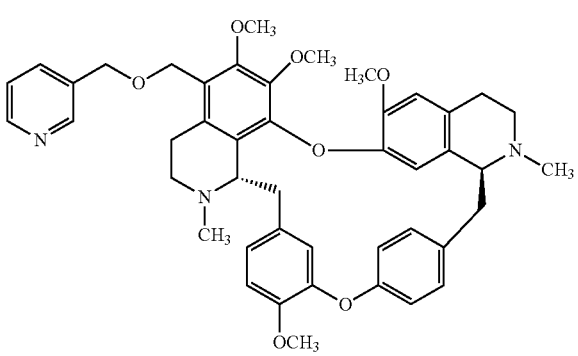

BS-TE-417
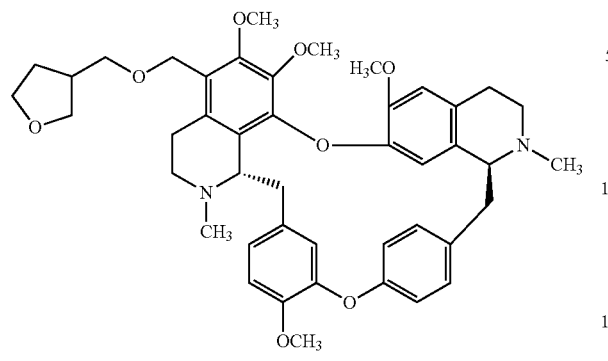
BS-TE-403
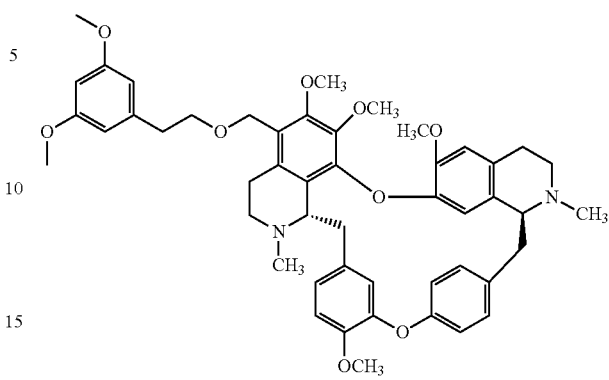
BS-TE-415
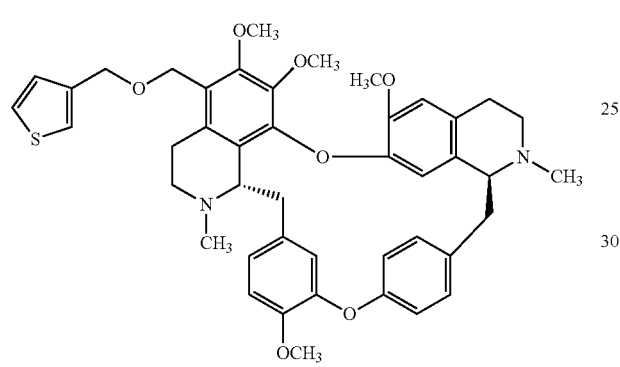
BS-TE-419
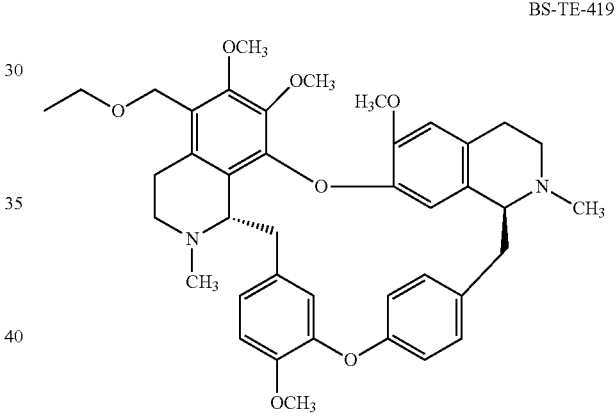
BS-TE-416
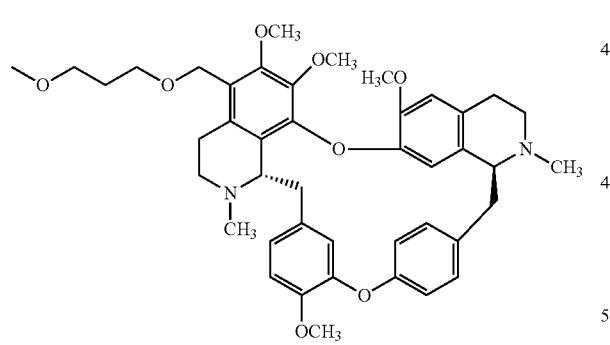
BS-TE-420
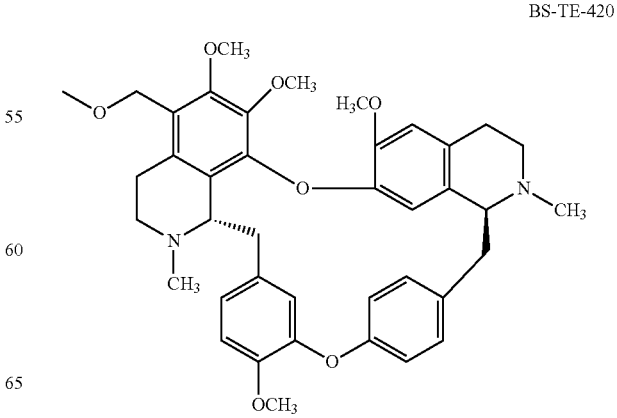
BS-TE-418
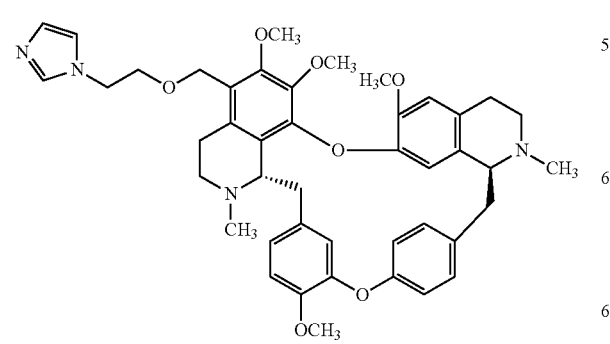

-continued

BS-TE-421

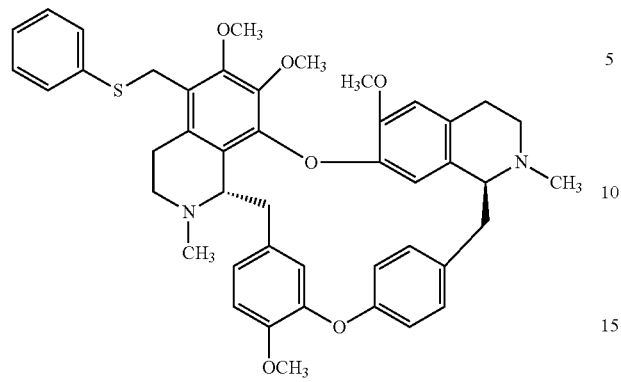

Some of the characterization data for the compounds listed above are shown in the following table:

| Compound ID | Molecular formula | Molecular weight | Appearance | State | Yield from two-step reaction (%) |
|---|---|---|---|---|---|
| BS-TE-204 | $C_{48}H_{53}N_3O_8$ | 799.95 | Dark yellow | Powdery solid | 18 |
| BS-TE-213 | $C_{39}H_{44}N_2O_7$ | 652.776 | Light yellow | Oil | 22 |
| BS-TE-215 | $C_{44}H_{46}N_2O_8S$ | 762.91 | Yellow | Powdery solid | 32 |
| BS-TE-216 | $C_{44}H_{46}N_2O_9$ | 746.32 | White | Powdery solid | 4 |
| BS-TE-223 | $C_{41}H_{46}N_2O_8$ | 694.33 | White | Powdery solid | 13 |
| BS-TE-224 | $C_{46}H_{48}N_2O_8$ | 756.882 | Light yellow | Bulk solid | 8 |
| BS-TE-301 | $C_{42}H_{49}N_3O_6$ | 691.36 | White | Powdery solid | 4 |
| BS-TE-305 | $C_{43}H_{51}N_3O_6$ | 705.38 | White | Powdery solid | 22 |
| BS-TE-307 | $C_{43}H_{51}N_3O_7$ | 721.88 | Light red | Powdery solid | 42 |
| BS-TE-308 | $C_{44}H_{53}N_3O_7$ | 735.91 | Yellow | Powdery solid | 52 |
| BS-TE-311 | $C_{42}H_{51}N_3O_6$ | 693.87 | Light yellow | Powdery solid | 23 |
| BS-TE-315 | $C_{42}H_{51}N_3O_7$ | 709.87 | Light yellow | Powdery solid | 55 |
| BS-TE-317 | $C_{48}H_{55}N_3O_6$ | 769.97 | Orange red | Powdery solid | 10 |
| BS-TE-320 | $C_{42}H_{46}N_4O_6S$ | 734.903 | Orange yellow | Powdery solid | 8 |
| BS-TE-321 | $C_{44}H_{53}N_3O_7$ | 735.91 | Brown yellow | Powdery solid | 4 |
| BS-TE-322 | $C_{43}H_{51}N_3O_7$ | 721.88 | Orange yellow | Powdery solid | 10 |
| BS-TE-323 | $C_{45}H_{52}N_4O_6$ | 744.92 | White | Powdery solid | 23 |
| BS-TE-326 | $C_{40}H_{47}N_3O_6$ | 665.818 | Light yellow | Powdery solid | 5 |
| BS-TE-328 | $C_{43}H_{51}N_3O_6S$ | 737.95 | Yellow | Powdery solid | 5 |
| BS-TE-329 | $C_{43}H_{49}N_3O_6$ | 703.866 | White | Powdery solid | 9 |
| BS-TE-330 | $C_{42}H_{46}N_4O_6$ | 702.34 | White | Powdery solid | 12 |
| BS-TE-333 | $C_{46}H_{58}N_4O_6$ | 762.44 | White | Powdery solid | 34 |
| BS-TE-334 | $C_{45}H_{56}N_4O_7$ | 764.41 | White | Powdery solid | 19 |
| BS-TE-340 | $C_{43}H_{53}N_3O_7$ | 723.39 | White | Powdery solid | 6 |
| BS-TE-341 | $C_{41}H_{49}N_3O_6$ | 679.844 | White | Powdery solid | 30 |
| BS-TE-342 | $C_{45}H_{56}N_4O_6$ | 748.95 | Yellow brown | Powdery solid | 22 |
| BS-TE-343 | $C_{49}H_{56}N_4O_6$ | 796.99 | Light pink | Powdery solid | 22 |
| BS-TE-346 | $C_{45}H_{55}N_3O_6$ | 733.94 | White | Powdery solid | 24 |
| BS-TE-348 | $C_{45}H_{50}N_4O_6$ | 742.9 | Yellow | Powdery solid | 18 |
| BS-TE-350 | $C_{44}H_{49}N_3O_7$ | 731.88 | Orange yellow | Powdery solid | 18 |
| BS-TE-351 | $C_{45}H_{55}N_3O_7$ | 749.93 | Yellow | Powdery solid | 32 |
| BS-TE-352 | $C_{45}H_{50}N_4O_6$ | 742.9 | Brown | Powdery solid | 32 |
| BS-TE-354 | $C_{46}H_{58}N_4O_6$ | 762.976 | White | Powdery solid | 12 |
| BS-TE-355 | $C_{44}H_{53}N_3O_6$ | 719.91 | White | Powdery solid | 29 |
| BS-TE-356 | $C_{45}H_{56}N_4O_6$ | 748.949 | White | Powdery solid | 35 |
| BS-TE-358 | $C_{45}H_{51}N_3O_7$ | 745.902 | White | Powdery solid | 18 |
| BS-TE-359 | $C_{44}H_{49}N_3O_6S$ | 747.941 | White | Powdery solid | 15 |
| BS-TE-360 | $C_{44}H_{54}N_4O_6$ | 734.92 | Yellow | Powdery solid | 25 |
| BS-TE-361 | $C_{39}H_{45}N_3O_6$ | 651.33 | White | Powdery solid | 7 |
| BS-TE-402 | $C_{47}H_{52}N_2O_8$ | 772.92 | Yellow | Powdery solid | 1 |
| BS-TE-403 | $C_{49}H_{56}N_2O_9$ | 816.4 | White | Powdery solid | 14 |
| BS-TE-406 | $C_{43}H_{52}N_2O_8$ | 724.88 | White | Powdery solid | 6 |
| BS-TE-408 | $C_{46}H_{49}FN_2O_7$ | 760.35 | White | Powdery solid | 17 |
| BS-TE-411 | $C_{45}H_{49}N_3O_7$ | 743.36 | White | Powdery solid | 11 |
| BS-TE-415 | $C_{44}H_{48}N_2O_7S$ | 748.32 | White | Powdery solid | 10 |
| BS-TE-416 | $C_{43}H_{52}N_2O_8$ | 724.88 | Light yellow | Powdery solid | 9 |
| BS-TE-417 | $C_{44}H_{52}N_2O_8$ | 736.37 | White | Powdery solid | 12 |
| BS-TE-418 | $C_{44}H_{50}N_4O_7$ | 746.37 | White | Powdery solid | 17 |
| BS-TE-419 | $C_{41}H_{48}N_2O_7$ | 680.83 | Light yellow | Powdery solid | 30 |
| BS-TE-420 | $C_{40}H_{46}N_2O_7$ | 666.8 | Light yellow | Powdery solid | 11 |
| BS-TE-421 | $C_{45}H_{48}N_2O_6S$ | 744.94 | Light yellow | Powdery solid | 35 |

In another embodiment, the compounds of formula (I) as follows are particularly preferred according to the present invention:

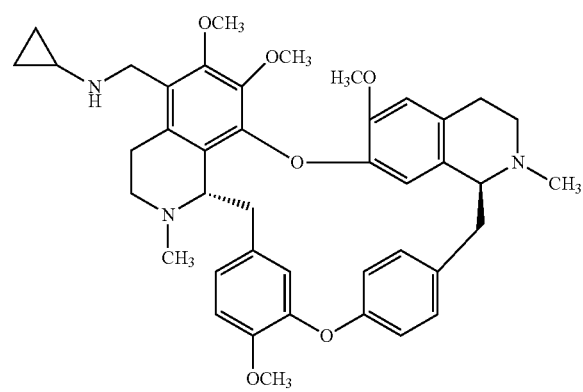

5-(cyclopropyl-amino-methyl)-tetrandrine
BS-TE-301

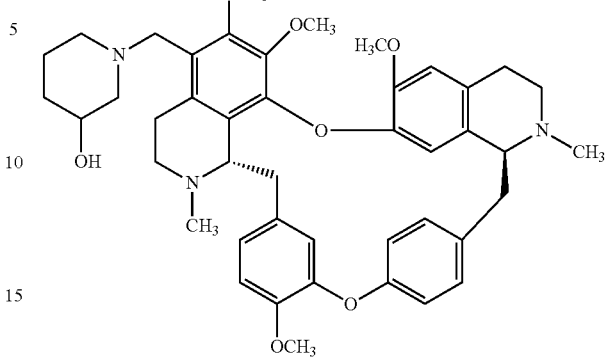

5-(m-hydroxypiperidinyl-methyl)-tetrandrine
BS-TE-321

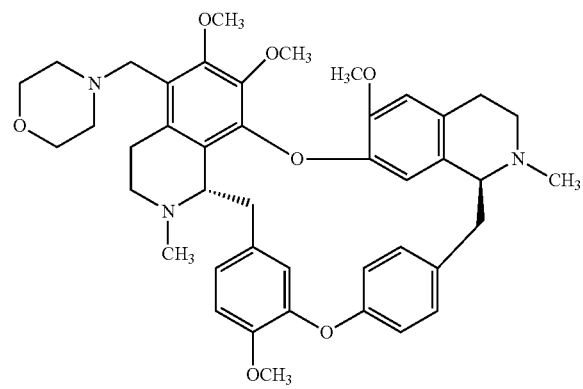

5-(morpholinyl-methyl)-tetrandrine
BS-TE-307

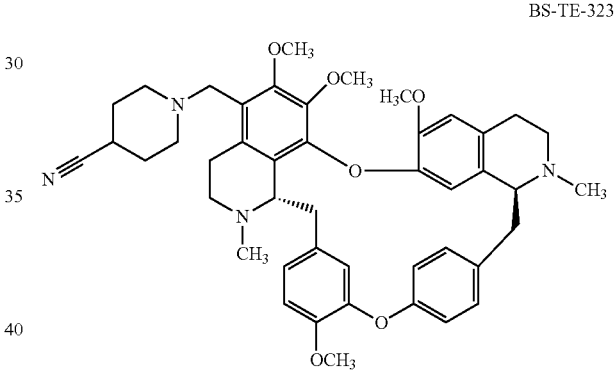

5-(p-cyanopiperidinylmethyl)-tetrandrine
BS-TE-323

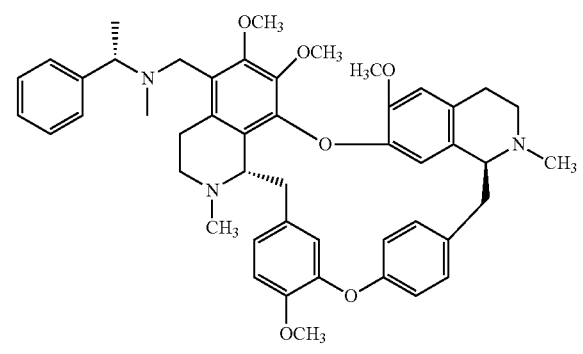

5-[(R)-N-methyl-phenylethyl-aminomethyl]-tetrandrine
BS-TE-317

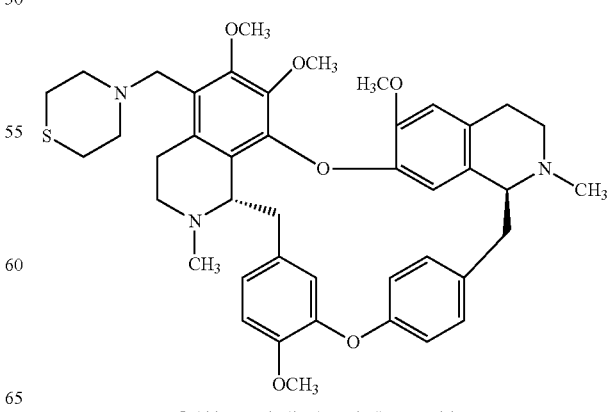

5-(thiomorpholinyl-methyl)-tetrandrine
BS-TE-328

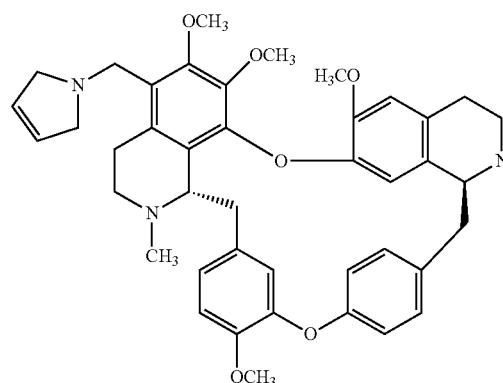
5-(2,5-dihydropyrrolyl-methyl)-tetrandrine
BS-TE-329
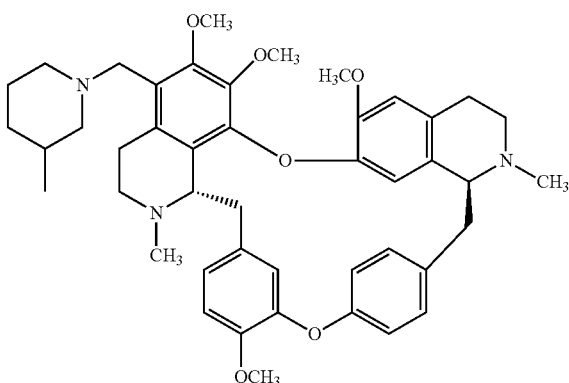
5-(m-methylpiperidinyl-methyl)-tetrandrine
BS-TE-346
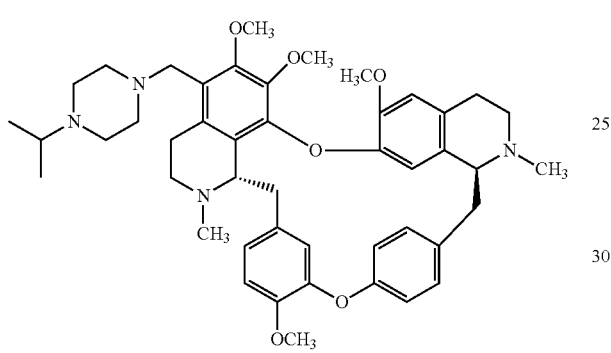
5-(N-isopropylpiperazinyl-methyl)-tetrandrine
BS-TE-333
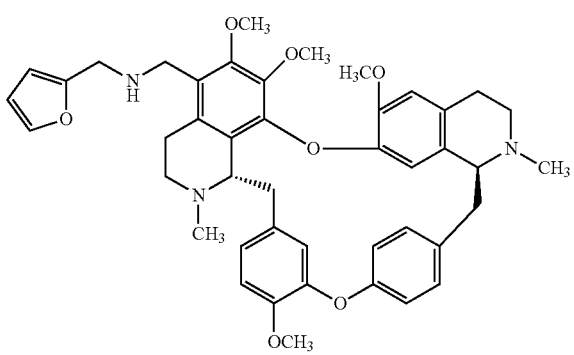
5-(furan-methylamino-methyl)-tetrandrine
BS-TE-350
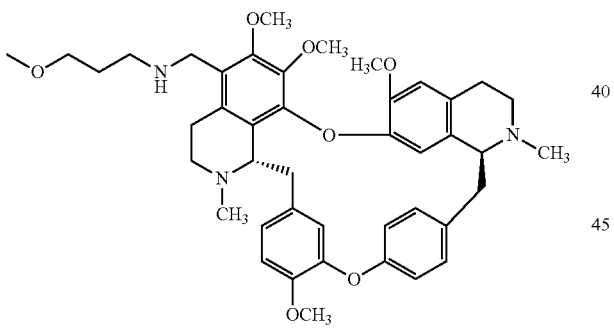
5-(methoxy-propylamino-methyl)-tetrandrine)
BS-TE-340
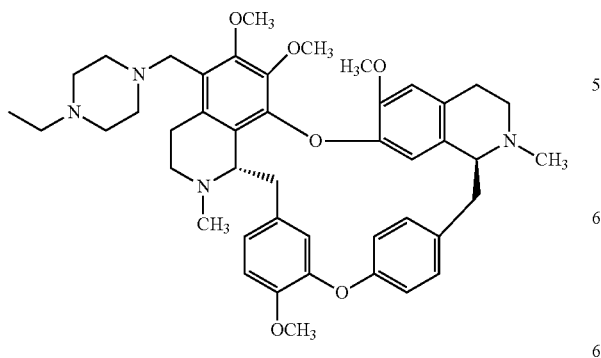
5-(N-ethylpiperazinyl-methyl)-tetrandrine
BS-TE-342
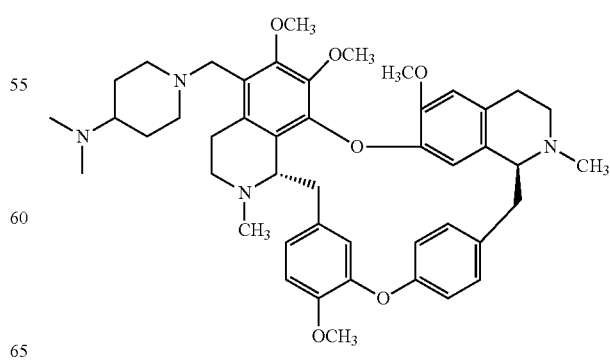
5-(4-dimethylaminopiperidinyl-methyl)-tetrandrine
BS-TE-354

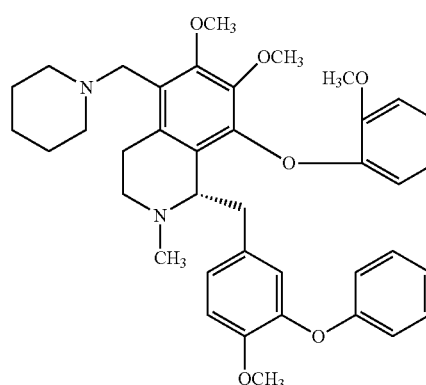
5-(piperidyl-methyl)-tetrandrine
BS-TE-355

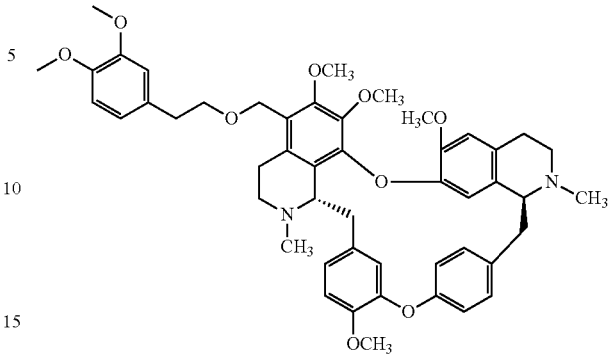
5-(3,4-dimethoxy-phenylethoxy-methyl)-tetrandrine
BS-TE-403

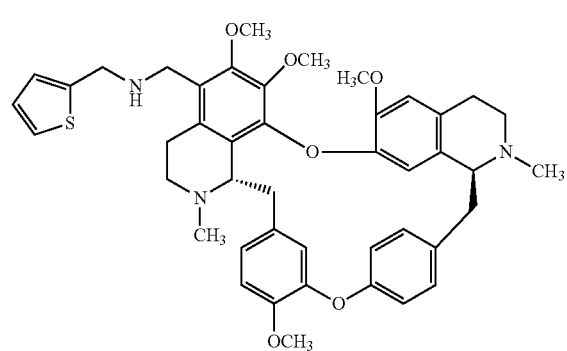
5-(N-methylpiperazinyl-methyl)-tetrandrine
BS-TE-359

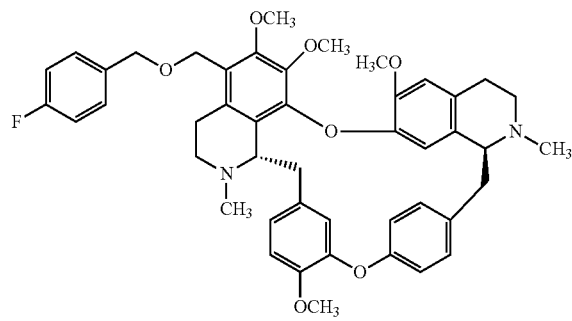
5-(p-fluoro-benzyloxy-methyl)-tetrandrine
BS-TE-408

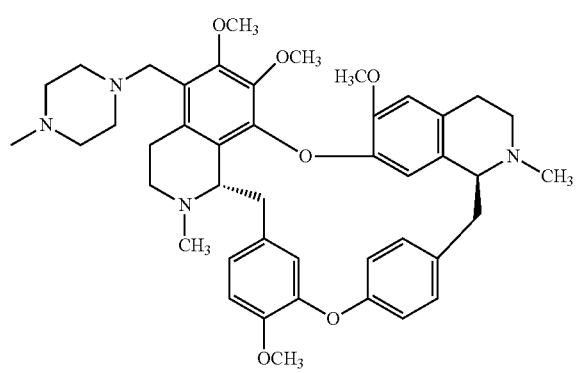
5-(N-methylpiperazinyl-methyl)-tetrandrine
BS-TE-360

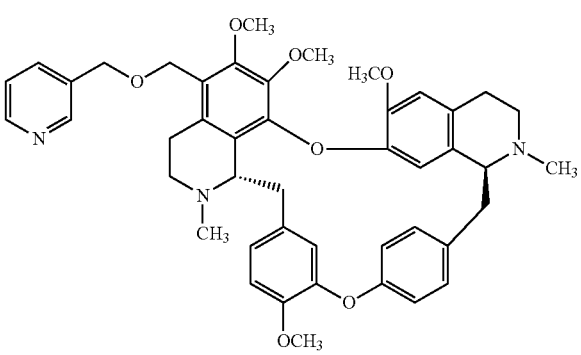
5-(m-pyridinylmethoxy-methyl)-tetrandrine
BS-TE-411

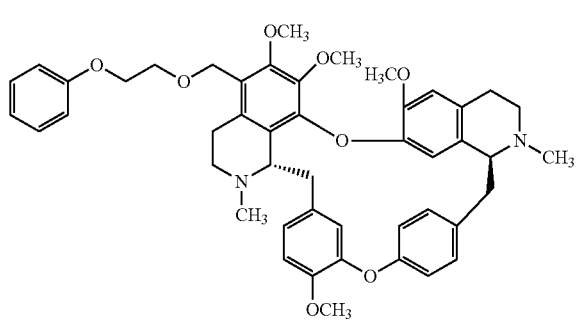
5-(phenoxy-ethoxy-methyl)-tetrandrine
BS-TE-402

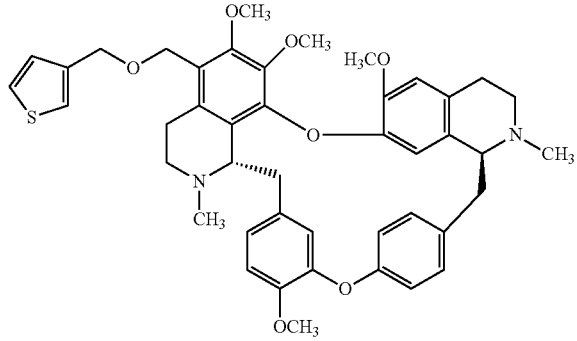
5-(m-thiophenylmethoxy-methyl)-tetrandrine
BS-TE-415

It has been proved that the compounds of the present invention possess antitumor activity and that the preferred compounds of the present invention possess distinctly superior antitumor activity to that of tetrandrine TTD.

The present invention relates to salts, solvates, hydrates, adducts, complexes, polymorphs and prodrugs of the compounds of formula (I) of the present invention.

As used herein, the term "alkyl" refers to a straight or branched hydrocarbon radical containing designated number of carbon atoms, such as $C_1$-$C_6$ alkyl, $C_1$-$C_5$ alkyl, $C_1$-$C_4$ alkyl, $C_1$-$C_3$ alkyl, etc. Examples of alkyl include, but not limited to, methyl, ethyl, n-propyl, isopropyl, tert-butyl, n-pentyl, n-hexyl, etc.

The term "$C_3$-$C_7$ cycloalkyl or cycloalkenyl" refers to a 3-7 membered monocyclic hydrocarbon radical which can be saturated (cycloalkyl) or unsaturated (cycloalkenyl), including 3-4 membered ring, 3-5 membered ring and 3-6 membered ring. Representative examples of $C_3$-$C_7$ cycloalkyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 carbon atoms. In the case of polycyclic aryl, at least one ring is aromatic. Aryl can also be fused with a heterocyclyl. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring atom(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other ring(s) can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc. "Nitrogen-containing heteroaryl" refers to a "heteroaryl" as defined above that comprises at least one nitrogen atom as a ring member.

"Heterocyclyl" refers to a non-aromatic cyclic group containing 1-4 heteroatoms (e.g. 1, 2, 3 or 4 heteroatoms) as ring members. A heteroatom refers to nitrogen, oxygen or sulfur. A heterocyclyl can be a monocyclic heterocyclyl having 4-8 ring atoms (such as 4-7 membered ring, 5-7 membered ring and 5-6 membered ring) or a bicyclic heterocyclyl having 7-11 ring atoms. A heterocyclyl can be saturated, or can be unsaturated and in the meantime non-aromatic. Examples of heterocyclyls include azacyclobutyl, pyrrolidinyl, pyrrolinyl, tetrahydrofuryl, dihydrofuryl, piperazinyl, piperidyl, morpholinyl, thiomorpholinyl, tetrahydropyranyl, tetrahydrothienyl, etc.

"Nitrogen-containing heterocyclyl" refers to a "heterocyclyl" as defined above that comprises at least one nitrogen atom as a ring member.

The term "halogen" refers to fluorine, chlorine, bromine or iodine.

The term "alkylamino" refers to an amino group substituted with one or two alkyl (including cycloalkyl) having designated number of carbon atoms.

The term "alkoxy" includes alkoxy and cycloalkyloxy.

The term "alkylthio" includes alkylthio and cycloalkylthio.

The term "pharmaceutically acceptable adducts and complexes of the compounds of formula (I)" refers to the product formed by a compound of the present invention with further combined small molecule or biological macromolecule via a non-chemical bond or non-covalent intermolecular force.

As used herein, examples of the term "pharmaceutically acceptable salts of the compounds of formula (I)" is exemplified by the organic acid salts formed by an organic acid bearing a pharmaceutically acceptable anion. These organic acid salts include, but not limited to, tosylate, methanesulfonate, malate, acetate, citrate, malonate, tartrate, succinate, benzoate, ascorbate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate salts and the like.

A pharmaceutically acceptable salt may be obtained using standard procedures well known in the art, for example by reacting a sufficient amount of alkaline compound with a suitable acid that provides a pharmaceutically acceptable anion.

As used herein, the term "polymorph" means a solid crystalline form of the compound of the present invention or a complex thereof. Various polymorphs of one same compound may exhibit different physical, chemical and/or spectroscopic properties. The different physical properties include, but not limited to, stability (e.g., thermal or light stability), compressibility and density (which are important for formulation and manufacture of the product), and dissolution rate (which may affect its bioavailability and absorbability). Differences in stability may result in a change in chemical reactivity (e.g., differential oxidation, such that a dosage form comprised of one polymorph discolors more rapidly than one comprised of another polymorph) or mechanical properties (e.g., in storage, crushed parts of the tablet of a kinetically favored polymorph is converted to a thermodynamically more stable polymorph) or both (e.g., tablets composed of one polymorph are more susceptible to breakdown at high humidity). Different physical properties of various polymorphs may affect their processing. For example, one polymorph may be more likely to form a solvate or may be more difficult to be filtered out or purified by washing than another one due to, for example, their different particle shapes or size distributions.

As used herein, the term "hydrate" means such a compound of the present invention or a salt thereof as further comprising a stoichiometric or non-stoichiometric amount of water bound via non-covalent intermolecular forces.

Unless otherwise indicated, the term "prodrug" used herein means a derivative of an inventive compound that, via hydrolyzation, oxidization, or other reactions under a biological condition (in vitro or in vivo), can provide a compound of this invention. A prodrug may only become active upon such a reaction under a biological condition, or may have activities in its unreacted form. Typically, a prodrug can be prepared using known methods, such as those described in *Burger's Medicinal Chemistry and Drug Discovery* (1995) 172-178, 949-982 (Manfred E. Wolff, 5$^{th}$ edition), *Prodrugs and Targeted Delivery* by J. Rautio (2011) 31-60 (Wiley-VCH, *Methods and Principles in Medicinal Chemistry*, Vol. 47), and *Fundamentals of Medicinal Chemistry* (2003) by G. Thomas, 195-200 (Wiley).

The two chiral centers of the 5-substituted tetrandrine derivatives in the compounds of the present invention have the stereochemical structure represented by the structural formula (I). The stereochemical definitions and conventions used herein generally follow MCGRAW-HILL DICTIONARY OF CHEMICAL TERMS (S. P. Parker, Ed., McGraw-Hill Book Company, New York, 1984); and ELIEL, E. AND WILEN, S., STEREOCHEMISTRY OF ORGANIC COMPOUNDS (John Wiley & Sons, Inc., New York, 1994). Many organic compounds are present in optically active forms, i.e., they have the ability to rotate a plane of plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention is prepared as follows.

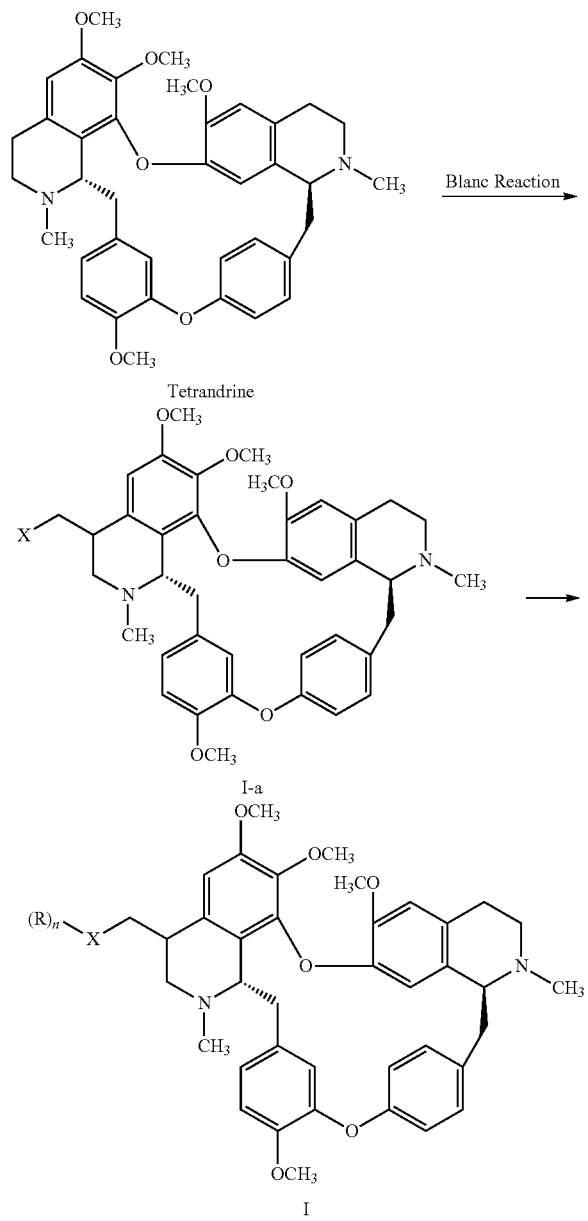

The raw material of formula (I), tetrandrine, can be obtained by extraction and separation from natural products. In the presence of hydrochloric acid and zinc chloride, tetrandrine and formaldehyde are subjected to Blanc Reaction of chloromethylation to produce 5-chloromethyltetrandrine (I-a, X=Cl). Blanc Reaction is typically carried out under low or room temperature. 5-chloromethyltetrandrine (I-a, X=Cl) can react with small molecules such as water, amine or hydroiodic acid to produce corresponding derivatives with substituted methyl groups, for example 5-hydroxymethyltetrandrine (I-a, X=OH), 5-aminomethyltetrandrine (I-a, X=NH2) and 5-iodomethyl-tetrandrine (I-a, X=I). 5-chloromethyltetrandrine (I-a, X=Cl) and corresponding small organic molecules are subjected to substitution reaction or condensation reaction to produce a 5-substituted tetrandrine derivative of formula (I), wherein R and X in formula (I) are as defined in the above formula (I).

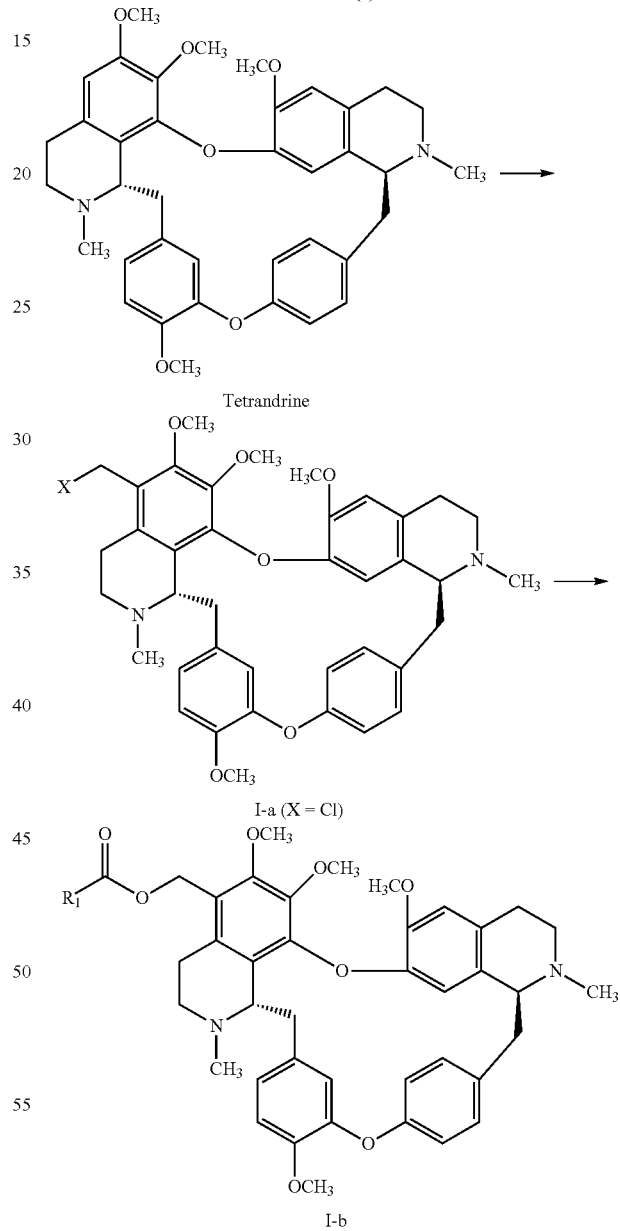

The tetrandrine derivative bearing a 5-esterified methyl of formula (I-b) of the present invention can be prepared according to the reaction shown above. In the reaction, 5-chloromethyltetrandrine (I-a, X=Cl) is produced via Blanc Reaction of chloromethylation, and then, in the presence of an alkali, said 5-chloromethyltetrandrine (I-a, X=Cl) and an appropriate sodium organic salt are heated in an organic solvent to produce the tetrandrine derivative of formula (I-b) via nucleophilic substitution reaction.

The alkali used in the above reaction includes, but not limited to, inorganic alkali, such as sodium hydride, sodium hydroxide, potassium hydroxide and lithium hydroxide. The sodium organic salt is a commercially available raw material, or it can be produced with an organic acid in the reaction system.

The temperature of the above reaction depends on the reactivity of the organic acid radical and it can be 50-80° C.

The above reaction typically takes place in a solvent. The solvents used include, but not limited to, acetonitrile, N,N-dimethylformamide and tetrahydrofuran.

$R_1$ and X in formula (I-b) are identical to those defined in the above formula (I), wherein X (=Cl) acts as a leaving group in the reaction.

The tetrandrine derivative bearing a 5-alkylaminomethyl group of formula (I-c) of the present invention can be prepared according to the reaction shown above. In the action, 5-chloromethyltetrandrine (I-a, X=Cl) is produced via Blanc Reaction, and then in the presence of an alkali, said 5-chloromethyltetrandrine (I-a, X=Cl) and an appropriate organic amine are heated in an organic solvent to produce the tetrandrine derivative of formula (I-c) via nucleophilic substitution reaction.

The alkali used in the above reaction includes, but not limited to, organic alkali such as N,N-diisopropylethylamine (DIPEA), triethylamine (TEA), pyridine and 4-dimethylaminopyridine (DMAP).

The temperature of the above reaction depends on the reactivity of the organic acid amide and it can be 50-80° C.

The above reaction typically takes place in a solvent. The solvents used include, but not limited to, acetonitrile, N,N-dimethylformamide and tetrahydrofuran.

$R_1$, $R_2$ and X in formula (I-c) are identical to those defined in the above formula (I), wherein X (=Cl) acts as a leaving group in the reaction.

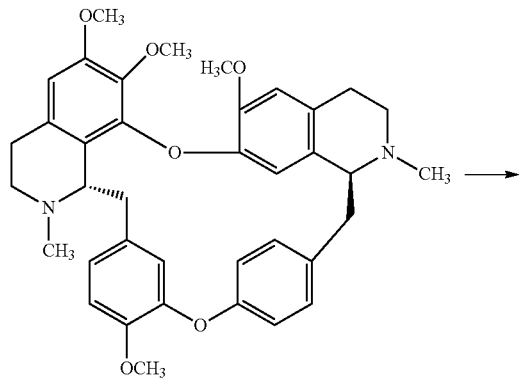
Tetrandrine

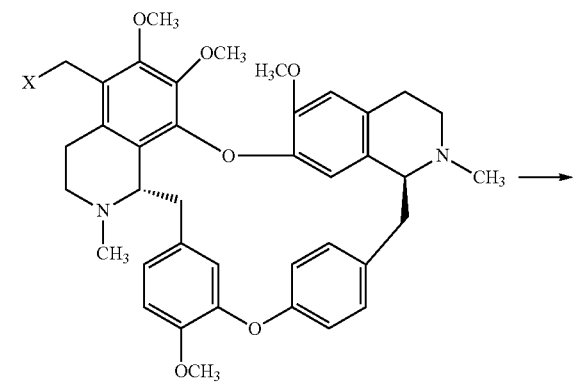
I-a (X = Cl)

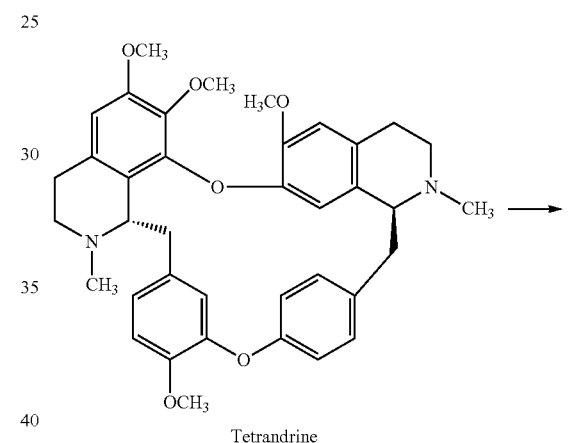
Tetrandrine

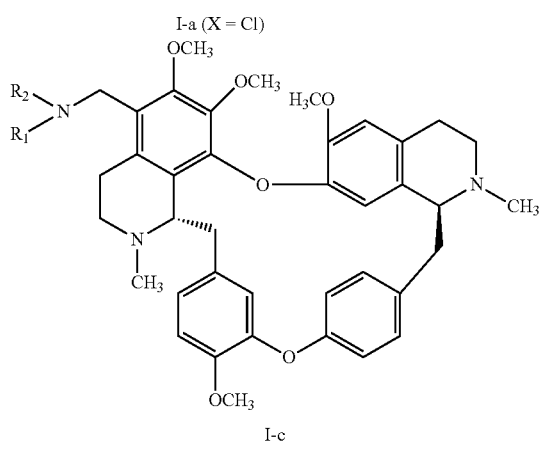
I-c

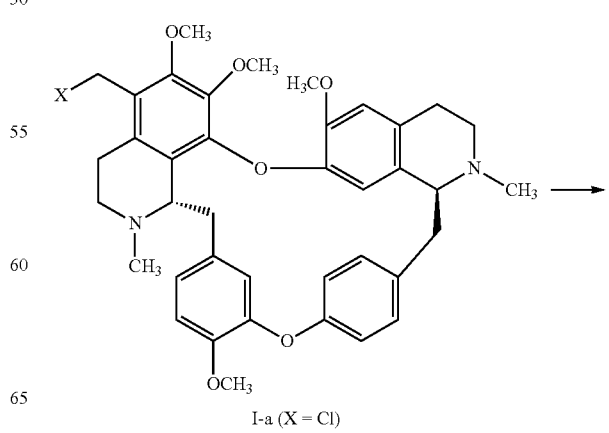
I-a (X = Cl)

-continued

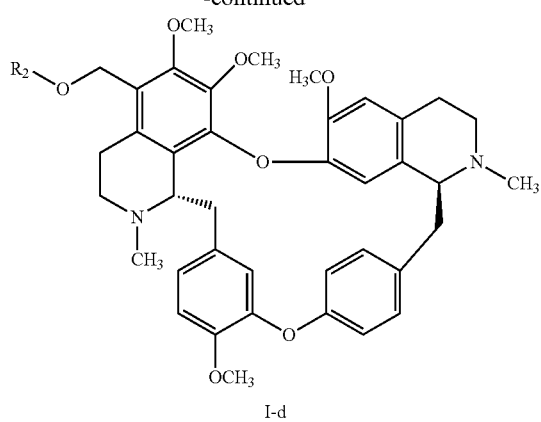

I-d

The tetrandrine derivative bearing a 5-alkoxymethyl of formula (I-d) of the present invention can be prepared according to the reaction shown above. In the reaction, 5-chloromethyltetrandrine (I-a, X═Cl) is produced via Blanc Reaction, and then in the presence of an alkali, said 5-chloromethyltetrandrine (I-a, X═Cl) and an appropriate organic alcohol or organic sodium alkoxide are heated in an organic solvent to produce the tetrandrine derivative of formula (I-d) via nucleophilic substitution reaction.

The alkali used in the above reaction includes, but not limited to, inorganic alkali such as sodium hydride, sodium hydroxide, potassium hydroxide and lithium hydroxide. The organic sodium alkoxide can be a commercially available raw material, or it can be produced from an alcohol in the reaction system.

The temperature of the above reaction depends on the reactivity of the alcohol and it can be 50-80° C.

The above reaction typically takes place in a solvent. The solvents used include, but not limited to, acetonitrile, N,N-dimethylformamide and tetrahydrofuran.

$R_1$ and X in formula (I-d) are as defined in the above formula (I), wherein X (═Cl) acts as a leaving group in the reaction.

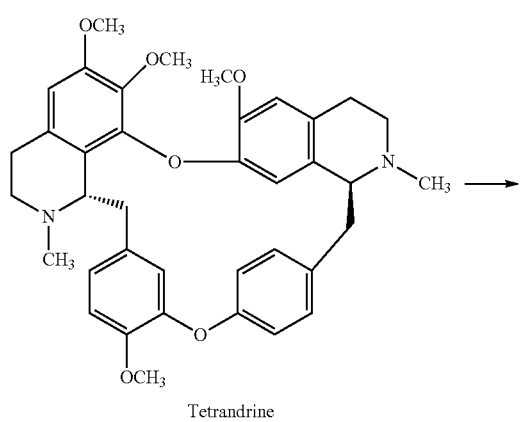

Tetrandrine

-continued

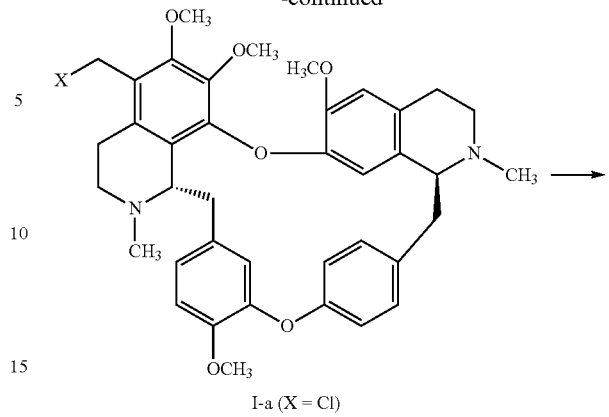

I-a (X = Cl)

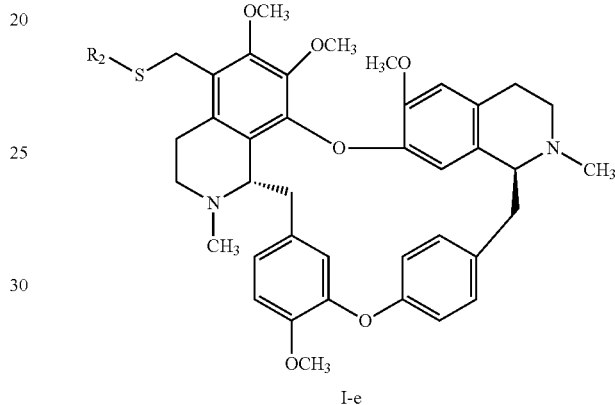

I-e

The tetrandrine derivative bearing a 5-alkylthiomethyl of formula (I-e) of the present invention can be prepared according to the reaction shown above. In the reaction, 5-chloromethyltetrandrine (I-a, X═Cl) is produced via Blanc Reaction, and then in the presence of an alkali, said 5-chloromethyltetrandrine (I-a, X═Cl) and an appropriate organic mercaptan or organic sodium mercaptide are heated in an organic solvent to produce the tetrandrine derivative of formula (I-e) via nucleophilic substitution reaction.

The alkali used in the above reaction includes, but not limited to, inorganic alkali such as sodium hydride, sodium hydroxide, potassium hydroxide and lithium hydroxide. The organic sodium mercaptide can be a commercially available raw material, or it can be produced from an organic mercaptan in the reaction system.

The temperature of the above reaction depends on the reactivity of the organic mercaptan and it can be 50-80° C.

The above reaction typically takes place in a solvent. The solvents used include, but not limited to, acetonitrile, N,N-dimethylformamide and tetrahydrofuran.

$R_1$ and X in formula (I-e) are as defined in the above formula (I), wherein X (═Cl) acts as a leaving group in the reaction.

The present invention also relates to the intermediate compound of formula (I-a), which can be used to prepare the compounds of the present invention, or a salt thereof,

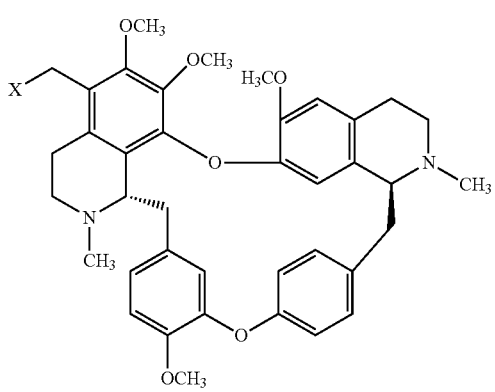

I-a wherein X is selected from hydroxyl, thiol, amino and halogen.

The raw materials for the above reactions, such as organic acids, sodium organic salts, organic anhydrides, organic acyl halides, alcohols, mercaptans, sodium alkoxides, sodium mercaptides, and organic amines, are all commercially available. The raw material tetrandrine is either obtained by the extraction and separation from natural products or is commercially available.

A typical operation of the above reactions can be, but not limited to, adding reactants and an alkali or a condensation agent in a suitable proportion to an acetonitrile solution of 5-chloromethyltetrandrine; allowing reaction for several hours under heating and stirring; extracting then the resulted products with an organic solvent; washing with water and saturated saline solution, drying and concentrating to obtain the crude product; and purifying the crude product with HPLC to obtain the pure product.

Blanc Reaction of chloromethylation (G. Blanc, Bull. Soc. Chim. France 33(4), 313 (1923); R. C. Fuson, C. H. McKeever, Org. React. 1, 63 (1942)) and Friedel-Crafts Reaction are operated under classical and mature conditions (C. C. Price, Org. React. 3, 1 (1946)).

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally or parenterally (for example, by an intravenous, intramuscular, topical or subcutaneous route).

Thus, the present compounds may be systemically administered, e.g., orally administered, in conjugation with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or in a device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredient (optionally encapsulated in liposomes), which are adapted for an extemporaneous preparation of a sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The 5-substituted tetrandrine derivatives of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be obtained by a synthesis method known in the art.

Example 1

The Synthesis of Compound BS-TE-215

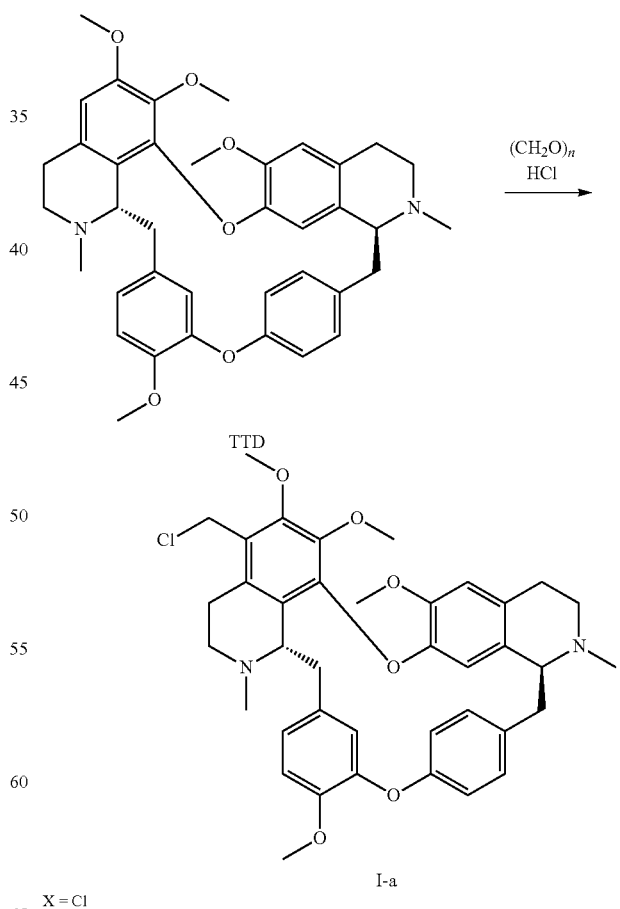

wherein (CH₂O)n: paraformaldehyde.

Tetrandrine (1.0 g, 1.6 mmol) is dissolved in concentrated HCl (5 mL), and paraformaldehyde (50 mg, 1.68 mmol) is added under 0° C. The reaction solution is warmed up to room temperature and stirred for 3 hours. It is then concentrated to give a crude product as a bright yellow solid, which is directly used in the next step of reaction.

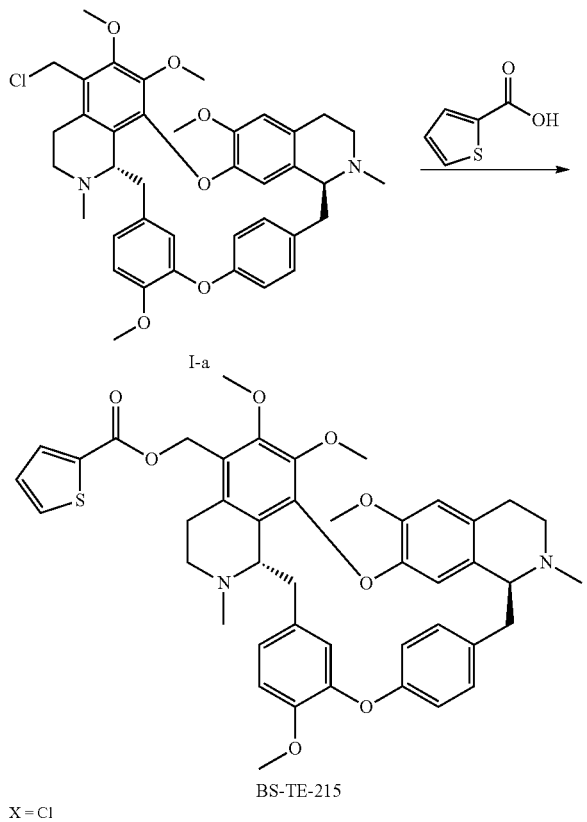

Sodium hydride (15 mg, 0.34 mmol) is added to a solution of 5-chloromethyltetrandrine (120 mg, 0.17 mmol) and thiophene-2-formic acid (44 mg, 0.34 mmol) in acetonitrile (3 mL). The reaction solution is heated up to 75° C. and stirred for 2 hours. The reaction solution is filtered, and the fitrated is concentrated to obtain a crude product, which is then separated and purified with preparative chromatography to give compound BS-TE-215 (36.8 mg, 32%) as a white solid powder.

LC-MS: 1.36 min (97.64%), m/z 382.8 [½ M+H]⁺.

¹H NMR (300 MHz, partial assignment of signals in CD₃OD) δ 7.79 (dd, J=3.6 Hz, 1.2 Hz, 1H), 7.74 (dd, J=4.8 Hz, 1.2 Hz, 1H), 7.55 (d, J=8.1 Hz, 2.8 Hz, 1H), 7.14-7.13 (m, 2H), 6.95 (m, 2H), 6.54-6.48 (m, 2H), 6.14 (s, 1H), 4.50 (m, 1H), 3.90 (s, 3H), 3.75 (s, 3H), 3.42 (s, 3H), 2.97 (s, 3H), 2.65 (s, 3H), 2.43 (s, 3H).

Compound BS-TE-202 is prepared by reacting 5-chloromethyltetrandrine with N,N-dimethylglycine using the same reagents and solvents according to the process for preparing BS-TE-215.

LC-MS 1.04 min (63.88%), 1.13 min (31.41%, isomer); m/z 739.6 [M+H]⁺.

¹H NMR (300 MHz, CD₃OD) δ 7.60 (d, 1H), 7.16 (d, 1H), 7.02 (m, 2H), 6.89 (d, 1H), 6.57-6.52 (m, 2H), 6.19 (s, 1H), 4.25 (m, 1H), 3.91 (s, 3H), 3.76 (s, 3H), 3.49 (s, 3H), 3.33 (s, 3H), 3.14 (s, 3H), 3.08 (s, 3H), 2.50 (s, 3H).

Compound BS-TE-204 is prepared by reacting 5-chloromethyltetrandrine with 4-dimethylaminobenzoic acid using the same reagents and solvents according to the process for preparing BS-TE-215.

LC-MS 1.36 min (90.68%); m/z 800.9 [M+H]⁺, 401.4 [½ M+H]⁺.

¹H NMR (300 MHz, CD₃OD) δ 7.81 (d, J=9 Hz, 2H), 7.50 (d, 1H), 7.11 (d, 1H), 6.93 (m, 2H), 6.77 (m, 2H), 6.67 (d, 2H), 6.55 (s, 1H), 3.89 (s, 3H), 3.73 (s, 3H), 3.41 (s, 3H), 3.34 (s, 3H), 3.01 (s, 6H), 2.85 (s, 3H), 2.36 (s, 3H).

Compound BS-TE-213 is prepared by reacting 5-chloromethyltetrandrine with 4-methylthiazole-5-formic acid using the same reagents and solvents according to the process for preparing BS-TE-215.

LC-MS 1.13 min (42.48%), 1.20 min (57.52%, isomer); m/z 653.8 [M+H]⁺, 327.8 [½ M+H]⁺.

¹H NMR (300 MHz, CD₃OD) δ 7.62 (dd, J=8.4 Hz, 2.8 Hz, 1H), 7.13 (dd, J=8.4 Hz, 2.4 Hz, 1H), 7.03 (d, 2H), 6.88 (s, 1H), 6.86 (d, 1H), 6.55 (d, 1H), 6.53 (s, 1H), 6.20 (s, 1H), 3.91 (s, 3H), 3.74 (s, 3H), 3.47 (s, 3H), 3.34 (s, 3H), 3.08 (s, 3H), 2.73 (s, 3H).

Compound BS-TE-216 is prepared by reacting 5-chloromethyltetrandrine with 2-furancarboxylic acid using the same reagents and solvents according to the process for preparing BS-TE-215.

LC-MS 1.27 min (98.44%). m/z 747.8 [M+H]⁺, 374.9 [½ M+H]⁺.

¹H NMR (300 MHz, CD₃OD) δ 7.71 (dd, J=1.5 Hz, 0.6 Hz, 1H), 7.47 (dd, J=8.4 Hz, 2.4 Hz, 1H), 7.19 (d, 1H), 7.09 (dd, J=8.4 Hz, 2.7 Hz, 1H), 6.90 (d, 1H), 6.86 (dd, J=8.1 Hz, 1.8 Hz, 1H), 6.79 (dd, J=8.4 Hz, 2.4 Hz, 1H), 6.68 (s, 1H), 6.56 (m, 2H), 6.42 (dd, J=8.1 Hz, 2.1 Hz, 1H), 6.03 (s, 1H), 4.03 (m, 1H), 3.88 (s, 3H), 3.72 (s, 3H), 3.37 (s, 3H), 3.24 (s, 3H), 2.65 (s, 3H), 2.25 (s, 3H).

Compound BS-TE-220 is prepared by reacting 5-chloromethyltetrandrine with 5-methylisoxazole-4-formic acid using the same reagents and solvents according to the process for preparing BS-TE-215.

LC-MS 1.27 min (88%). m/z 762.9 [M+H]⁺.

Compound BS-TE-223 is prepared by reacting 5-chloromethyltetrandrine with acetic acid using the same reagents and solvents according to the process for preparing BS-TE-215:

LC-MS 1.19 min (91.97%). m/z 695.8 [M+H]⁺, 348.8 [½ M+H]⁺.

¹H NMR (300 MHz, CD₃OD) δ 7.52 (dd, J=8.1 Hz, 1.8 Hz, 1H), 7.47 (dd, J=8.1 Hz, 2.4 Hz, 1H), 6.94 (d, 1H), 6.89 (dd, J=7.8 Hz, 2.1 Hz, 1H), 6.82 (dd, J=8.1 Hz, 2.4 Hz, 1H), 6.76 (s, 1H), 6.53 (d, 1H), 6.47 (dd, J=8.1 Hz, 2.1 Hz, 1H), 6.09 (s, 1H), 4.32 (m, 1H), 3.97 (d, 1H), 3.89 (s, 3H), 3.70 (s, 3H), 3.41 (s, 3H), 3.25 (s, 3H), 2.84 (s, 3H), 2.72-2.55 (m, 4H), 2.35 (s, 3H), 2.03 (s, 3H).

Compound BS-TE-224 is prepared by reacting 5-chloromethyltetrandrine with benzoic acid using the same reagents and solvents according to the process for preparing BS-TE-215.

LC-MS 1.38 min (85.3%). m/z 757.8 [M+H]⁺, 379.9 [½ M+H]⁺.

¹H NMR (300 MHz, CD₃OD) δ 7.98 (m, 2H), 7.58-7.42 (m, 4H), 7.10 (dd, J=8.4 Hz, 2.4 Hz, 1H), 6.95-6.87 (m, 2H), 6.82 (dd, J=8.4 Hz, 2.4 Hz, 1H), 6.76 (s, 1H), 6.54 (d, 1H), 6.47 (dd, J=8.4 Hz, 1.8 Hz, 1H), 6.09 (s, 1H), 4.30 (m, 1H), 4.01 (d, 1H), 3.88 (s, 3H), 3.73 (s, 3H), 3.40 (s, 3H), 3.26 (s, 3H), 2.83 (s, 3H), 2.34 (s, 3H).

Example 2

The Synthesis of Compound BS-TE-305

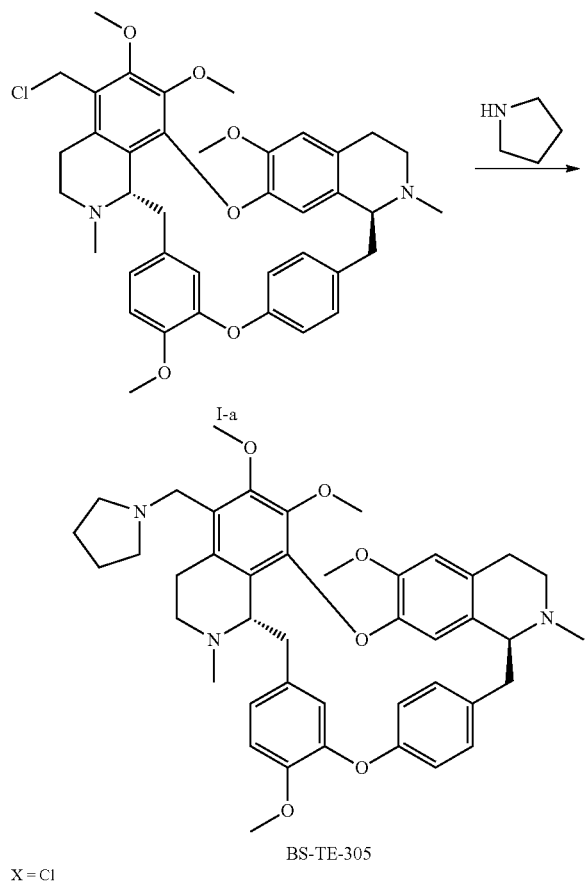

Sodium hydride (15 mg, 0.34 mmol) is added to a solution of 5-chloromethyltetrandrine (120 mg, 0.17 mmol), N,N-diisopropylethylamine (60 uL, 0.34 mmol) and pyrrolidine (24 mg, 0.34 mmol) in acetonitrile (3 mL). The reaction solution is heated up to 75° C. and stirred for 2 hours.

Afterwards, the reaction solution is filtered, and the fitrate is concentrated to obtain a crude product, which is then separated and purified with preparative chromatography to give compound BS-TE-305 (30.5 mg, 22%) as a white solid powder.

LC-MS: 1.05 min (91.95%), m/z 706.9 [M+H]$^+$, 354.4 [½ M+H]$^+$.

$^1$H NMR (300 MHz, CD$_3$OD) δ 7.54 (dd, J=8.4 Hz, 2.4 Hz, 1H), 7.14 (dd, J=8.4 Hz, 2.4 Hz, 1H), 6.95 (d, 1H), 6.91 (dd, J=8.1 Hz, 1.8 Hz, 1H), 6.85-6.81 (m, 2H), 6.51-6.48 (m, 2H), 6.14 (s, 1H), 4.49 (m, 1H), 3.90 (s, 3H), 3.80 (s, 3H), 3.44 (s, 3H), 3.31 (s, 3H), 2.95 (s, 3H), 2.35 (s, 3H).

Compound BS-TE-301 is prepared by reacting 5-chloromethyltetrandrine with cyclopropylamine using the same alkaline reagents and solvents according to the process for preparing BS-TE-305:

LC-MS 1.06 min (74.25%). m/z 692.9 [M+H]$^+$, 347.3 [½ M+H]$^+$.

$^1$H NMR (300 MHz, CD$_3$OD) δ 7.46 (dd, J=8.1 Hz, 2.4 Hz, 1H), 7.07 (dd, J=8.1 Hz, 2.4 Hz, 1H), 6.90 (d, 1H), 6.86 (dd, J=8.1 Hz, 1.8 Hz, 1H), 6.75 (dd, J=8.1 Hz, 2.7 Hz, 1H), 6.66 (s, 1H), 6.54 (d, 1H), 6.41 (dd, J=8.1 Hz, 2.1 Hz, 1H), 6.01 (s, 1H), 4.01 (m, 1H), 3.88 (s, 3H), 3.80 (d, 1H), 3.73 (s, 3H), 3.35 (s, 3H), 3.23 (s, 3H), 2.63 (s, 3H), 2.25 (s, 3H).

Compound BS-TE-307 is prepared by reacting 5-chloromethyltetrandrine with morpholine using the same alkaline reagents and solvents according to the process for preparing BS-TE-305.

LC-MS 1.01 min (91.41%). m/z 722.8 [M+H]$^+$, 362.4 [½ M+H]$^+$.

$^1$H NMR (300 MHz, CD$_3$OD) δ 7.53 (dd, J=8.1 Hz, 2.1 Hz, 1H), 7.11 (dd, J=8.1 Hz, 2.4 Hz, 1H), 6.96 (d, 1H), 6.93 (dd, J=7.8 Hz, 2.1 Hz, 1H), 6.81 (dd, J=8.4 Hz, 2.7 Hz, 1H), 6.76 (s, 1H), 6.54 (d, 1H), 6.48 (dd, J=8.1 Hz, 2.1 Hz, 1H), 6.10 (s, 1H), 4.34 (m, 1H), 4.13 (d, 1H), 3.90 (s, 3H), 3.38 (s, 3H), 3.26 (s, 3H), 2.85 (s, 3H), 2.69 (d, 1H), 2.45 (s, 3H).

Compound BS-TE-308 is prepared by reacting 5-chloromethyltetrandrine with 4-hydroxypiperidine using the same alkaline reagents and solvents according to the process for preparing BS-TE-305.

LC-MS 1.00 min (80.99%). m/z 736.9 [M+H]$^+$, 369.3 [½ M+H]$^+$.

$^1$H NMR (300 MHz, CD$_3$OD) δ 7.65 (d, J=9.0 Hz, 1H), 7.15 (dd, J=8.4 Hz, 1.8 Hz, 1H), 7.07 (s, 2H), 6.90 (m, 2H), 6.59 (dd, J=8.4 Hz, 2.1 Hz, 1H), 6.52 (s, 1H), 6.23 (s, 1H), 3.92 (s, 3H), 3.83 (s, 3H), 3.51 (s, 3H), 3.34 (s, 3H), 3.11 (s, 3H), 2.79 (s, 3H).

Compound BS-TE-311 is prepared by reacting 5-chloromethyltetrandrine with isopropylamine using the same alkaline reagents and solvents according to the process for preparing BS-TE-305.

LC-MS 1.08 min (69.65%). m/z 694.9 [M+H]$^+$, 348.4 [½ M+H]$^+$.

$^1$H NMR (300 MHz, CD$_3$OD) δ 7.64 (d, J=6.0 Hz, 1H), 7.14 (dd, J=7.8 Hz, 2.1 Hz, 1H), 7.04 (s, 2H), 6.90 (m, 2H), 6.57 (dd, J=8.1 Hz, 1.8 Hz, 1H), 6.51 (s, 1H), 6.23 (s, 1H), 3.92 (s, 3H), 3.86 (s, 3H), 3.50 (s, 3H), 3.34 (s, 3H), 3.11 (s, 3H), 2.75 (s, 3H).

Compound BS-TE-313 is prepared by reacting 5-chloromethyltetrandrine with 4-amino-1-methylpiperidine using the same alkaline reagents and solvents according to the process for preparing BS-TE-305.

LC-MS 1.01 min (58.11%), 1.12 min (29.03%, isomer). m/z 750.9 [M+H]$^+$.

$^1$H NMR (300 MHz, CD$_3$OD) δ 7.64 (d, 1H), 7.15 (dd, 1H), 7.04 (s, 2H), 6.90 (s, 2H), 6.51 (m, 2H), 6.24 (s, 1H), 3.92 (s, 3H), 3.87 (s, 3H), 3.51 (s, 3H), 3.35 (s, 3H), 3.11 (s, 3H), 2.79 (s, 3H).

Compound BS-TE-315 is prepared by reacting 5-chloromethyltetrandrine with 1-amino-2-propanol using the same alkaline reagents and solvents according to the process for preparing BS-TE-305.

LC-MS 1.04 min (94.45%). m/z 710.9 [M+H]$^+$, 356.4 [½ M+H]$^+$.

$^1$H NMR (300 MHz, CD$_3$OD) δ 7.47 (d, J=9.0 Hz, 1H), 7.08 (dd, J=8.1 Hz, 2.4 Hz, 1H), 6.93 (d, 1H), 6.85 (dd, J=8.4 Hz, 1.8 Hz, 1H), 6.78 (d, 1H), 6.66 (s, 1H), 6.54 (s, 1H), 6.38 (dd, J=8.4 Hz, 1.5 Hz), 6.01 (s, 1H), 3.88 (s, 3H), 3.74 (s, 3H), 3.36 (s, 3H), 3.23 (s, 3H), 2.62 (s, 3H), 2.24 (s, 3H), 1.29 (s, 3H).

Compound BS-TE-317 is prepared by reacting 5-chloromethyltetrandrine with (S)—N-methyl-1-phenylethylamine using the same alkaline reagents and solvents according to the process for preparing BS-TE-305.

LC-MS 1.11 min (97.03%). m/z 770.9 [M+H]$^+$, 386.5 [½ M+H]$^+$.

$^1$H NMR (300 MHz, CD$_3$OD) δ 7.65 (d, J=9.0 Hz, 1H), 7.15 (dd, J=8.4 Hz, 1.8 Hz, 1H), 7.07 (s, 2H), 6.90 (s, 2H), 6.59 (dd, J=8.4 Hz, 2.1 Hz, 1H), 6.52 (s, 1H), 6.23 (s, 1H), 3.92 (s, 3H), 3.83 (s, 3H), 3.51 (s, 3H), 3.34 (s, 3H), 3.11 (s, 3H), 2.79 (s, 3H).

Compound BS-TE-320 is prepared by reacting 5-chloromethyltetrandrine with 2-aminothiazole using the same alkaline reagents and solvents according to the process for preparing BS-TE-305.

LC-MS 1.10 min (55.04%), 1.20 min (13.08%, isomer). m/z 735.8 [M+H]$^+$, 368.8 [½ M+H]$^+$.

$^1$H NMR (300 MHz, CD$_3$OD) δ 7.50 (dd, J=8.1 Hz, 2.1 Hz, 1H), 7.09 (dd, J=8.1 Hz, 2.14 Hz, 1H), 6.93 (d, 1H), 6.85 (dd, J=8.1 Hz, 1.8 Hz, 1H), 6.75 (dd, J=8.1 Hz, 2.1 Hz, 1H), 6.68 (s, 1H), 6.55 (d, 1H), 6.42 (dd, J=8.1 Hz, 2.1 Hz, 1H), 6.20 (m, 2H), 6.03 (s, 1H), 3.96 (m, 1H), 3.90 (s, 3H), 3.68 (s, 3H), 3.38 (s, 3H), 3.26 (s, 3H), 2.74 (s, 3H), 2.22 (s, 3H).

Compound BS-TE-321 is prepared by reacting 5-chloromethyltetrandrine with 3-hydroxypiperidine using the same alkaline reagents and solvents according to the process for preparing BS-TE-305.

LC-MS 1.01 min (95.15%). m/z 736.9 [M+H]$^+$, 369.4 [½ M+H]$^+$.

$^1$H NMR (300 MHz, CD$_3$OD) δ 7.45 (dd, J=8.1 Hz, 2.1 Hz, 1H), 7.06 (dd, J=8.1 Hz, 2.4 Hz, 1H), 6.91 (d, 1H), 6.87 (dd, J=7.8 Hz, 1.8 Hz, 1H), 6.77 (dd, J=8.1 Hz, 2.4 Hz, 1H), 6.67 (s, 1H), 6.56 (d, 1H), 6.42 (dd, J=8.1 Hz, 2.4 Hz, 1H), 6.02 (s, 1H), 4.04 (m, 1H), 3.88 (s, 3H), 3.68 (s, 3H), 3.35 (d, 3H), 3.24 (d, 3H), 2.66 (s, 3H), 2.55 (d, 1H), 2.27 (s, 3H).

Compound BS-TE-322 is prepared by reacting 5-chloromethyltetrandrine with 3-hydroxypyrrolidine using the same alkaline reagents and solvents according to the process for preparing BS-TE-305.

LC-MS 1.03 min (59.49%), 1.11 min (31.36%, isomer). m/z 722.9 [M+H]$^+$, 362.3 [½ M+H]$^+$.

$^1$H NMR (300 MHz, CD$_3$OD) δ 7.47 (dd, J=8.1 Hz, 1.8 Hz, 1H), 7.07 (dd, J=8.1 Hz, 2.7 Hz, 1H), 6.90 (d, 1H), 6.85 (dd, J=8.1 Hz, 1.8 Hz, 1H), 6.77 (dd, J=8.1 Hz, 2.4 Hz, 1H), 6.65 (s, 1H), 6.55 (d, 1H), 6.41 (dd, J=8.1 Hz, 2.1 Hz, 1H), 6.00 (s, 1H), 4.29 (s, 1H), 3.99 (m, 1H), 3.88 (s, 3H), 3.67 (s, 3H), 3.35 (s, 3H), 3.23 (s, 3H), 2.62 (s, 3H), 2.23 (s, 3H).

Compound BS-TE-323 is prepared by reacting 5-chloromethyltetrandrine with 4-cyanopiperidine using the same alkaline reagents and solvents according to the process for preparing BS-TE-305.

LC-MS 1.11 min (81.69%). m/z 745.9 [M+H]$^+$, 373.8 (½ M+H).

$^1$H NMR (300 MHz, CD$_3$OD) δ 7.47 (dd, J=8.4 Hz, 2.1 Hz, 1H), 7.07 (dd, J=8.1 Hz, 2.7 Hz, 1H), 6.91 (d, 1H), 6.83 (dd, J=7.8 Hz, 1.8 Hz, 1H), 6.78 (dd, J=8.4 Hz, 2.7 Hz, 1H), 6.66 (s, 1H), 6.56 (d, 1H), 6.41 (dd, J=8.1 Hz, 1.8 Hz, 1H), 6.01 (s, 1H), 4.57 (s, 1H), 4.01 (m, 1H), 3.88 (s, 3H), 3.73 (s, 1H), 3.66 (s, 3H), 3.33 (s, 3H), 3.23 (s, 3H), 2.63 (s, 3H), 2.24 (s, 3H).

Compound BS-TE-326 is prepared by reacting 5-chloromethyltetrandrine with methylamine using the same alkaline reagents and solvents according to the process for preparing BS-TE-305.

LC-MS 1.16 min (83.64%). m/z 666.8 [M+H]$^+$.

$^1$H NMR (300 MHz, CD$_3$OD) δ 7.49 (dd, J=8.1 Hz, 2.1 Hz, 1H), 7.09 (dd, J=8.1 Hz, 2.4 Hz, 1H), 6.92 (d, 1H), 6.88 (dd, J=8.1 Hz, 1.8 Hz, 1H), 6.78 (dd, J=8.1 Hz, 2.7 Hz, 1H), 6.70 (s, 1H), 6.53 (d, 1H), 6.41 (dd, J=8.4 Hz, 2.1 Hz, 1H), 6.04 (s, 1H), 4.56 (s, 1H), 4.12 (m, 1H), 3.89 (s, 3H), 3.69 (s, 3H), 3.37 (s, 3H), 3.27 (s, 3H), 2.71 (s, 3H), 2.55 (d, 1H), 2.26 (s, 3H).

Compound BS-TE-328 is prepared by reacting 5-chloromethyltetrandrine with thiomorpholine using the same alkaline reagents and solvents according to the process for preparing BS-TE-305.

LC-MS 1.11 min (88.79%), 1.25 min (10.42%, isomer), 1.41 min (0.79%). m/z 738.8 [M+H]$^+$, 370.3 [½ M+H]$^+$.

$^1$H NMR (300 MHz, CD$_3$OD) δ 7.46 (dd, J=8.1 Hz, 2.1 Hz, 1H), 7.07 (dd, J=8.1 Hz, 2.4 Hz, 1H), 6.90 (d, 1H), 6.86 (dd, J=8.1 Hz, 1.8 Hz, 1H), 6.78 (dd, J=8.1 Hz, 2.4 Hz, 1H), 6.65 (s, 1H), 6.55 (d, 1H), 6.41 (dd, J=8.4 Hz, 2.1 Hz, 1H), 6.00 (s, 1H), 4.29 (s, 1H), 4.00 (m, 1H), 3.88 (s, 3H), 3.66 (s, 3H), 3.32 (s, 3H), 3.22 (s, 3H), 2.63 (s, 3H), 2.23 (s, 3H).

Compound BS-TE-329 is prepared by reacting 5-chloromethyltetrandrine with 2,5-dihydropyrrole using the same alkaline reagents and solvents according to the process for preparing BS-TE-305.

LC-MS 1.10 min (45.45%), 1.34 min (31.32%, isomer). m/z 704.9 [M+H]$^+$, 353.3 [½ M+H]$^+$.

$^1$H NMR (300 MHz, CD$_3$OD) δ 7.44 (dd, J=8.41 Hz, 1.8 Hz, 1H), 7.08 (dd, J=8.1 Hz, 2.7 Hz, 1H), 6.90 (d, 1H), 6.85 (dd, J=8.1 Hz, 1.8 Hz, 1H), 6.77 (dd, J=8.1 Hz, 2.7 Hz, 1H), 6.66 (s, 1H), 6.55 (d, 1H), 6.41 (dd, J=8.4 Hz, 2.1 Hz, 1H), 6.01 (m, 2H), 6.00-5.78 (s, 1H), 4.00 (m, 1H), 3.88 (s, 3H), 3.67 (s, 3H), 3.35 (s, 3H), 3.24 (s, 3H), 2.63 (s, 3H), 2.51 (d, 1H), 2.25 (s, 3H).

Compound BS-TE-330 is prepared by reacting 5-chloromethyltetrandrine with pyrazole using the same alkaline reagents and solvents according to the process for preparing BS-TE-305.

LC-MS 1.20 min (58.93%), 1.22 min (39.49%, isomer). m/z 703.8 [M+H]$^+$, 352.9 [½ M+H]$^+$.

$^1$H NMR (300 MHz, CD$_3$OD) δ 7.44 (m, 2H), 7.28 (d, 1H), 7.07 (dd, J=8.1 Hz, 2.7 Hz, 1H), 6.89 (d, 1H), 6.85 (dd, J=8.1 Hz, 2.1 Hz, 1H), 6.77 (dd, J=8.1 Hz, 2.4 Hz, 1H), 6.67 (s, 1H), 6.54 (d, 1H), 6.41 (dd, J=8.1 Hz, 2.1 Hz, 1H), 6.23 (t, 1H), 6.02 (s, 1H), 4.00 (m, 1H), 3.87 (s, 3H), 3.61 (s, 3H), 3.36 (s, 3H), 3.25 (s, 3H), 2.62 (s, 3H), 2.20 (s, 3H).

Compound BS-TE-333 is prepared by reacting 5-chloromethyltetrandrine with 1-isopropylpiperazine using the same alkaline reagents and solvents according to the process for preparing BS-TE-305.

LC-MS 1.06 min (97.06%). m/z 763.9 [M+H]$^+$, 383.0 [½ M+H]$^+$.

$^1$H NMR (300 MHz, CD$_3$OD) δ 7.47 (dd, J=8.4 Hz, 2.1 Hz, 1H), 7.08 (dd, J=8.4 Hz, 2.4 Hz, 1H), 6.91 (d, 1H), 6.86 (dd, J=8.1 Hz, 1.8 Hz, 1H), 6.79 (dd, J=8.1 Hz, 2.4 Hz, 1H), 6.66 (s, 1H), 6.56 (d, 1H), 6.43 (dd, J=8.1 Hz, 2.1 Hz, 1H), 6.00 (s, 1H), 4.29 (s, 1H), 3.99 (m, 1H), 3.89 (s, 3H), 3.67 (s, 3H), 3.34 (s, 3H), 3.24 (s, 3H), 2.63 (s, 3H), 2.24 (s, 3H).

Compound BS-TE-334 is prepared by reacting 5-chloromethyltetrandrine with N-hydroxyethylpiperazine using the same alkaline reagents and solvents according to the process for preparing BS-TE-305.

LC-MS 1.02 min (98.72%). m/z 765.9 [M+H]$^+$, 384.0 [½ M+H]$^+$.

¹H NMR (300 MHz, CD₃OD) δ 7.47 (dd, J=8.1 Hz, 1.8 Hz, 1H), 7.07 (dd, J=8.1 Hz, 2.4 Hz, 1H), 6.91 (d, 1H), 6.86 (dd, J=8.1 Hz, 1.8 Hz, 1H), 6.77 (dd, J=8.4 Hz, 2.7 Hz, 1H), 6.66 (s, 1H), 6.56 (d, 1H), 6.41 (dd, J=8.1 Hz, 1.8 Hz, 1H), 6.00 (s, 1H), 4.29 (s, 1H), 3.99 (m, 1H), 3.89 (s, 3H), 3.66 (s, 3H), 3.33 (s, 3H), 3.23 (s, 3H), 2.63 (s, 3H), 2.24 (s, 3H).

Compound BS-TE-340 is prepared by reacting 5-chloromethyltetrandrine with 3-methoxypropylamine using the same alkaline reagents and solvents according to the process for preparing BS-TE-305.

LC-MS 1.07 min (73.86%), 1.12 min (14.47%, isomer). m/z 724.9 [M+H]⁺, 363.4 [½ M+H]⁺.

¹H NMR (300 MHz, CD₃OD) δ 7.47 (dd, J=8.4 Hz, 2.4 Hz, 1H), 7.07 (dd, J=8.1 Hz, 2.4 Hz, 1H), 6.91 (d, 1H), 6.85 (dd, J=8.4 Hz, 1.8 Hz, 1H), 6.77 (dd, J=8.4 Hz, 2.7 Hz, 1H), 6.67 (s, 1H), 6.54 (d, 1H), 6.41 (dd, J=8.4 Hz, 1.8 Hz, 1H), 6.02 (s, 1H), 3.99 (m, 1H), 3.88 (s, 3H), 3.75 (s, 3H), 3.36 (s, 3H), 3.24 (s, 3H), 2.62 (s, 3H), 2.49 (d, 1H), 2.24 (s, 3H).

Compound BS-TE-341 is prepared by reacting 5-chloromethyltetrandrine with dimethylamine using the same alkaline reagents and solvents according to the process for preparing BS-TE-305.

LC-MS 1.07 min (71.60%), 1.17 min (16.12%, isomer). m/z 680.9 [M+H]⁺, 341.3 [½ M+H]⁺.

¹H NMR (300 MHz, CD₃OD) δ 7.65 (dd, J=8.1 Hz, 2.1 Hz, 1H), 7.20 (dd, J=8.4 Hz, 2.4 Hz, 1H), 6.91 (d, 1H), 6.88 (m, 1H), 6.59 (dd, J=8.1 Hz, 2.1 Hz, 1H), 6.52 (s, 1H), 6.24 (s, 1H), 4.35 (d, 1H), 3.92 (s, 3H), 3.86 (s, 3H), 3.51 (s, 3H), 3.34 (s, 3H), 3.11 (s, 3H), 2.89 (s, 6H), 2.74 (s, 3H).

Compound BS-TE-342 is prepared by reacting 5-chloromethyltetrandrine with N-ethylpiperazine using the same alkaline reagents and solvents according to the process for preparing BS-TE-305.

LC-MS 1.09 min (77.97%), 1.17 min (20.17%, isomer). m/z 749.9 [M+H]⁺, 375.9 [½ M+H]⁺.

¹H NMR (300 MHz, CD₃OD) δ 7.47 (dd, J=8.1 Hz, 2.1 Hz, 1H), 7.07 (dd, J=8.1 Hz, 2.7 Hz, 1H), 6.91 (d, 1H), 6.86 (dd, J=8.1 Hz, 1.8 Hz, 1H), 6.79 (dd, J=8.4 Hz, 2.4 Hz, 1H), 6.66 (s, 1H), 6.56 (d, 1H), 6.41 (dd, J=8.1 Hz, 2.1 Hz, 1H), 6.00 (s, 1H), 4.29 (s, 1H), 3.99 (m, 1H), 3.88 (s, 3H), 3.66 (s, 3H), 3.33 (s, 3H), 3.23 (s, 3H), 2.62 (s, 3H), 2.24 (s, 3H), 1.28 (s, 3H).

Compound BS-TE-343 is prepared by reacting 5-chloromethyltetrandrine with N-phenylpiperazine using the same alkaline reagents and solvents according to the process for preparing BS-TE-305.

LC-MS 1.44 min (79.45%), 1.63 min (9.06%). m/z 797.9 [M+H]⁺, 400.0 [½ M+H]⁺.

¹H NMR (300 MHz, CD₃OD) δ 7.47 (dd, J=8.1 Hz, 2.1 Hz, 1H), 7.256-7.173 (m, 2H), 7.08 (dd, J=8.1 Hz, 2.4 Hz, 1H), 7.00-6.92 (m, 3H), 6.87 (dd, J=8.1 Hz, 1.8 Hz, 1H), 6.83-6.76 (m, 2H), 6.69 (s, 1H), 6.56 (d, 1H), 6.43 (dd, J=8.1 Hz, 2.1 Hz, 1H), 6.04 (s, 1H), 4.29 (s, 1H), 4.10 (m, 1H), 3.97 (d, 1H), 3.89 (s, 3H), 3.69 (s, 3H), 3.36 (s, 3H), 3.26 (s, 3H), 2.69 (s, 3H), 2.30 (s, 3H).

Compound BS-TE-346 is prepared by reacting 5-chloromethyltetrandrine with 3-methylpiperidine using the same alkaline reagents and solvents according to the process for preparing BS-TE-305.

LC-MS 1.35 min (90.37%). m/z 734.9 [M+H]⁺, 368.4 [½ M+H]⁺.

¹H NMR (300 MHz, CD₃OD) δ 7.47 (dd, J=8.1 Hz, 2.1 Hz, 1H), 7.07 (dd, J=8.4 Hz, 2.7 Hz, 1H), 6.91 (d, 1H), 6.85 (dd, J=8.1 Hz, 1.8 Hz, 1H), 6.78 (dd, J=8.1 Hz, 2.7 Hz, 1H), 6.67 (s, 1H), 6.55 (d, 1H), 6.41 (dd, J=8.1 Hz, 2.1 Hz, 1H), 6.02 (s, 1H), 4.01 (m, 1H), 3.89 (s, 3H), 3.69 (s, 3H), 3.36 (s, 3H), 3.25 (s, 3H), 2.64 (s, 3H), 2.25 (s, 3H).

Compound BS-TE-348 is prepared by reacting 5-chloromethyltetrandrine with 3-pyridylmethylamine using the same alkaline reagents and solvents according to the process for preparing BS-TE-305.

LC-MS 1.24 min (21.76%, isomer), 1.32 (69.43%). m/z 743.9 [M+H]⁺, 372.9 [½ M+H]⁺.

¹H NMR (300 MHz, CD₃OD) δ 8.56 (d, 1H), 8.45 (dd, J=4.8 Hz, 1.5 Hz, 1H), 7.90 (d, 1H), 7.50 (dd, J=8.1 Hz, 2.1 Hz, 1H), 7.45-7.40 (m, 2H), 7.10 (dd, J=8.1 Hz, 2.4 Hz, 1H), 6.92 (d, 1H), 6.88 (dd, J=7.8 Hz, 2.1 Hz, 1H), 6.80 (dd, J=8.4 Hz, 2.4 Hz, 1H), 6.71 (s, 1H), 6.52 (d, 1H), 6.45 (dd, J=8.7 Hz, 2.4 Hz, 1H), 6.05 (s, 1H), 4.20 (m, 1H), 3.89 (s, 3H), 3.66 (s, 3H), 3.37 (s, 3H), 3.25 (s, 3H), 2.74 (s, 3H), 2.54 (d, 1H), 2.31 (s, 3H).

Compound BS-TE-350 is prepared by reacting 5-chloromethyltetrandrine with 3-furylmethylamine using the same alkaline reagents and solvents according to the process for preparing BS-TE-305.

LC-MS 1.13 min (99.16%). m/z 732.5 [M+H]⁺, 366.7 [M+H]⁺.

¹H NMR (300 MHz, CD₃OD) δ 7.52 (d, 1H), 7.49 (dd, J=7.8 Hz, 2.1 Hz, 1H), 7.09 (dd, J=8.7 Hz, 2.1 Hz, 1H), 6.94 (d, 1H), 6.86 (dd, J=8.4 Hz, 1.8 Hz, 1H), 6.76 (dd, J=8.1 Hz, 2.7 Hz, 1H), 6.70 (s, 1H), 6.52 (d, 1H), 6.41 (m, 3H), 6.04 (s, 1H), 4.11 (m, 1H), 3.89 (s, 3H), 3.70 (s, 3H), 3.37 (s, 3H), 3.25 (s, 3H), 2.7 (s, 3H) 2.28 (s, 3H).

Compound BS-TE-351 is prepared by reacting 5-chloromethyltetrandrine with 3-hydroxymethylpiperidine using the same alkaline reagents and solvents according to the process for preparing BS-TE-305.

LC-MS 1.28 min (83.02%), 1.42 min (16.98%, isomer). m/z 750.9 [M+H]⁺, 376.4 [½ M+H]⁺.

¹H NMR (300 MHz, CD₃OD) δ 7.47 (dd, J=8.4 Hz, 2.1 Hz, 1H), 7.07 (dd, J=8.1 Hz, 2.4 Hz, 1H), 6.91 (d, 1H), 6.87 (dd, J=8.1 Hz, 1.8 Hz, 1H), 6.77 (dd, J=8.4 Hz, 2.4 Hz, 1H), 6.66 (s, 1H), 6.55 (d, 1H), 6.41 (dd, J=8.1 Hz, 1.8 Hz, 1H), 6.01 (s, 1H), 4.00 (m, 1H), 3.88 (s, 3H), 3.68 (s, 3H), 3.34 (s, 3H), 3.24 (s, 3H), 2.63 (s, 3H), 2.53 (d, 1H), 2.24 (s, 3H).

Compound BS-TE-352 is prepared by reacting 5-chloromethyltetrandrine with 2-methylaminopyridine using the same alkaline reagents and solvents according to the process for preparing BS-TE-305.

LC-MS 1.33 min (54.28%), 1.74 min (0.28%, isomer). m/z 743.9 [M+H]⁺, 372.9 [½ M+H]⁺.

¹H NMR (300 MHz, CD₃OD) δ 8.49 (d, 1H), 7.79 (td, 1H), 7.45 (m, 2H), 7.30 (m, 1H), 7.05 (dd, J=8.4 Hz, 2.4 Hz, 1H), 6.90 (d, 1H), 6.85 (dd, J=8.1 Hz, 1.8 Hz, 1H), 6.77 (dd, J=8.1 Hz, 2.1 Hz, 1H), 6.65 (s, 1H), 6.53 (d, 1H), 6.40 (dd, J=8.4 Hz, 2.1 Hz, 1H), 6.00 (s, 1H), 4.01 (m, 1H), 3.88 (s, 3H), 3.67 (s, 3H), 3.33 (s, 3H), 3.23 (s, 3H), 2.63 (s, 3H), 2.24 (s, 3H).

Compound BS-TE-354 is prepared by reacting 5-chloromethyltetrandrine with 4-dimethylaminopiperidine using the same alkaline reagents and solvents according to the process for preparing BS-TE-305.

LC-MS 1.21 min (91.1%). m/z 763.9 [M+H]⁺, 383.0 [½ M+H]⁺.

¹H NMR (300 MHz, CD₃OD) δ 7.47 (dd, J=8.4 Hz, 2.1 Hz, 1H), 7.07 (dd, J=8.1 Hz, 2.4 Hz, 1H), 6.91 (d, 1H), 6.85 (dd, J=7.8 Hz, 1.8 Hz, 1H), 6.79 (dd, J=8.1 Hz, 2.4 Hz, 1H), 6.66 (s, 1H), 6.56 (d, 1H), 6.41 (dd, J=8.1 Hz, 2.1 Hz, 1H), 6.00 (s, 1H), 3.99 (m, 1H), 3.88 (s, 3H), 3.66 (s, 3H), 3.33 (s, 3H), 3.23 (s, 3H), 2.63 (s, 3H), 2.35 (s, 6H), 2.23 (s, 3H).

Compound BS-TE-355 is prepared by reacting 5-chloromethyltetrandrine with piperidine using the same alkaline reagents and solvents according to the process for preparing BS-TE-305.

LC-MS 1.31 min (89.22%). m/z 720.9 [M+H]⁺, 361.4 [½ M+H]⁺.

¹H NMR (300 MHz, CD₃OD) δ 7.45 (dd, J=8.1 Hz, 2.1 Hz, 1H), 7.06 (dd, J=8.4 Hz, 2.7 Hz, 1H), 6.91 (d, 1H), 6.84 (dd, J=8.4 Hz, 1.8 Hz, 1H), 6.76 (dd, J=8.4 Hz, 2.7 Hz, 1H), 6.66 (s, 1H), 6.56 (d, 1H), 6.39 (dd, J=8.1 Hz, 2.1 Hz, 1H), 5.96 (s, 1H), 3.98 (m, 1H), 3.89 (s, 3H), 3.67 (s, 3H), 3.34 (s, 3H), 3.24 (s, 3H), 2.62 (s, 3H), 2.23 (s, 3H).

Compound BS-TE-356 is prepared by reacting 5-chloromethyltetrandrine with N-methylhomopiperazine using the same alkaline reagents and solvents according to the process for preparing BS-TE-305.

LC-MS 1.24 min (84.77%). m/z 750.0 [M+H]⁺, 375.9 [½ M+H]⁺.

¹H NMR (300 MHz, CD₃OD) δ 7.47 (dd, J=8.1 Hz, 2.1 Hz, 1H), 7.07 (dd, J=8.1 Hz, 2.7 Hz, 1H), 6.91 (d, 1H), 6.86 (dd, J=8.4 Hz, 2.1 Hz, 1H), 6.79 (dd, J=8.4 Hz, 2.7 Hz, 1H), 6.66 (s, 1H), 6.56 (d, 1H), 6.42 (dd, J=8.1 Hz, 2.1 Hz, 1H), 6.01 (s, 1H), 3.99 (m, 1H), 3.89 (s, 3H), 3.66 (s, 3H), 3.33 (s, 3H), 3.23 (s, 3H), 2.63 (s, 3H), 2.64 (s, 3H), 2.24 (s, 3H).

Compound BS-TE-358 is prepared by reacting 5-chloromethyltetrandrine with 5-methyl-2-furylmethylamine using the same alkaline reagents and solvents according to the process for preparing BS-TE-305.

LC-MS 1.42 min (98.01%). m/z 747.0 [M+H]⁺, 374.4 [½ M+H]⁺.

¹H NMR (300 MHz, CD₃OD) δ 7.52 (dd, J=8.4 Hz, 2.1 Hz, 1H), 7.10 (dd, J=8.1 Hz, 2.7 Hz, 1H), 6.92 (d, 1H), 6.87 (dd, J=8.1 Hz, 1.8 Hz, 1H), 6.82 (dd, J=8.1 Hz, 2.4 Hz, 1H), 6.74 (s, 1H), 6.51 (d, 1H), 6.46 (dd, J=8.1 Hz, 2.1 Hz, 1H), 6.41 (d, 1H), 6.07 (s, 1H), 6.05 (dd, J=3.3 Hz, 1.2 Hz, 1H), 4.24 (m, 1H), 3.89 (s, 3H), 3.72 (s, 3H), 3.39 (s, 3H), 3.27 (s, 3H), 2.79 (s, 3H), 2.30 (s, 3H).

Compound BS-TE-359 is prepared by reacting 5-chloromethyltetrandrine with 2-thienylmethylamine using the same alkaline reagents and solvents according to the process for preparing BS-TE-305.

LC-MS 1.37 min (99.05%). m/z 748.8 [M+H]⁺, 375.4 [½ M+H]⁺.

¹H NMR (300 MHz, CD₃OD) δ 7.46 (dd, J=8.4 Hz, 2.4 Hz, 1H), 7.32 (dd, J=5.1 Hz, 1.2 Hz, 1H), 7.07 (dd, J=8.1 Hz, 2.4 Hz, 1H), 7.01 (d, 1H), 6.98-6.95 (m, 2H), 6.90 (d, 1H), 6.85 (dd, J=8.1 Hz, 1.8 Hz, 1H), 6.77 (dd, J=8.1 Hz, 2.4 Hz, 1H), 6.66 (s, 1H), 6.54 (d, 1H), 6.40 (dd, J=8.1 Hz, 2.1 Hz, 1H), 6.00 (s, 1H), 3.88 (s, 3H), 3.70 (d, 1H), 3.67 (s, 3H), 3.35 (s, 3H), 3.23 (s, 3H), 2.62 (s, 3H), 2.23 (s, 3H).

Compound BS-TE-360 is prepared by reacting 5-chloromethyltetrandrine with N-methylpiperazine using the same alkaline reagents and solvents according to the process for preparing BS-TE-305.

LC-MS 1.26 min (81.86%), 1.41 min (14.19%, isomer). m/z 735.9 [M+H]⁺, 368.9 [½ M+H]⁺.

¹H NMR (300 MHz, CD₃OD) δ 7.47 (dd, J=7.5 Hz, 2.4 Hz, 1H), 7.07 (dd, J=8.1 Hz, 2.7 Hz, 1H), 6.91 (d, 1H), 6.86 (dd, J=8.1 Hz, 1.8 Hz, 1H), 6.79 (dd, J=8.4 Hz, 2.1 Hz, 1H), 6.66 (s, 1H), 6.55 (d, 1H), 6.42 (dd, J=8.1 Hz, 1.5 Hz, 1H), 6.01 (s, 1H), 4.01 (m, 1H), 3.89 (s, 3H), 3.66 (s, 3H), 3.33 (s, 3H), 3.23 (s, 3H), 2.64 (s, 3H), 2.24 (d, 6H).

Compound BS-TE-361 is prepared by reacting 5-chloromethyltetrandrine with ammonia water using the same alkaline reagents and solvents according to the process for preparing BS-TE-305.

LC-MS 0.72 min (89.40%). m/z 651.0 [M+H]⁺, 326.6 [½ M+H]⁺.

Example 3

The Synthesis of Compound BS-TE-418

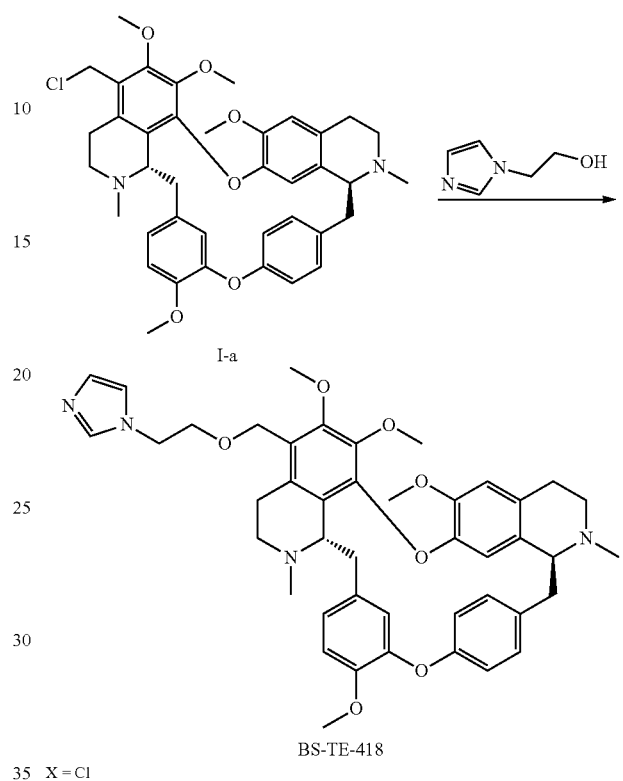

X = Cl

Sodium hydride (15 mg, 0.34 mmol) is added to a solution of 5-chloromethyltetrandrine (120 mg, 0.17 mmol) and 1-(2-hydroxyethyl)imidazole (20 mg, 0.25 mmol) in acetonitrile (3 mL). The reaction solution is heated up to 75° C. and stirred for 2 hours. Afterwards, the reaction solution is filtered, and the filtrate is concentrated to obtain a crude product, which is then separated and purified with preparative chromatography to give compound BS-TE-418 (20 mg, 18%) as a white solid powder.

LC-MS: 1.07 min (95.52%), m/z 747 [M+H]⁺, 374 [½ M+H]⁺.

¹H NMR (300 MHz, CD₃OD) δ 7.60 (s, 1H), 7.45 (dd, J=8.4 Hz, 1.8 Hz, 1H), 7.10 (s, 1H), 7.07 (dd, J=8.4 Hz, 2.7 Hz, 1H), 6.94-6.91 (m, 2H), 6.86 (dd, J=8.1 Hz, 1.8 Hz, 1H), 6.77 (d, J=8.4 Hz, 2.4 Hz, 1H), 6.67 (s, 1H), 6.53 (d, 1H), 6.41 (dd, J=8.1 Hz, 2.1 Hz, 1H), 4.02 (m, 1H), 3.88 (s, 3H), 3.61 (s, 3H), 3.34 (s, 3H), 3.21 (s, 3H), 2.65 (s, 3H), 2.22 (s, 3H).

Compound BS-TE-402 is prepared by reacting 5-chloromethyltetrandrine with 2-phenoxyethanol using the same alkaline reagents and solvents according to the process for preparing BS-TE-418.

LC-MS 1.67 min (91.83%). m/z 773.9 [M+H]⁺, 387.9 [½ M+H]⁺.

¹H NMR (300 MHz, CD₃OD) δ 7.44 (dd, J=8.1 Hz, 2.1 Hz, 1H), 7.23 (m, 2H), 7.06 (dd, J=8.1 Hz, 2.4 Hz, 1H), 6.92-6.87 (m, 4H), 6.84 (dd, J=8.1 Hz, 1.8 Hz, 1H), 6.76 (dd, J=8.4 Hz, 2.4 Hz, 1H), 6.65 (s, 1H), 6.54 (d, 1H), 6.38 (dd, J=8.1 Hz, 2.1 Hz, 1H), 6.00 (s, 1H), 4.59 (s, 1H), 4.11 (m, 2H), 3.99 (m, 1H), 3.88 (s, 3H), 3.82 (m, 2H), 3.68 (s, 3H), 3.34 (s, 3H), 3.20 (s, 3H), 2.62 (s, 3H), 2.48 (d, 1H), 2.22 (s, 3H).

Compound BS-TE-403 is prepared by reacting 5-chloromethyltetrandrine with 3,5-dimethoxyphenylethanol using the same alkaline reagents and solvents according to the process for preparing BS-TE-418.

LC-MS 1.32 min (95.19%). m/z 817.9 [M+H]⁺, 410.0 [½ M+H]⁺.

¹H NMR (300 MHz, CD₃OD) δ 7.44 (dd, J=8.4 Hz, 2.4 Hz, 1H), 7.05 (dd, J=8.1 Hz, 2.4 Hz, 1H), 6.90 (d, 1H), 6.90-6.85 (m, 3H), 6.76-6.71 (m, 2H), 6.64 (s, 1H), 6.52 (d, 1H), 6.38 (dd, J=8.1 Hz, 2.1 Hz, 1H), 5.99 (s, 1H), 4.48 (m, 2H), 3.99 (m, 1H), 3.88 (s, 3H), 3.78 (s, 3H), 3.76 (s, 3H), 3.62 (s, 3H), 3.19 (s, 3H), 2.62 (s, 3H), 2.17 (s, 3H).

Compound BS-TE-406 is prepared by reacting 5-chloromethyltetrandrine with 1-methoxy-2-propanol using the same alkaline reagents and solvents according to the process for preparing BS-TE-418.

LC-MS 1.22 min (85.14%). m/z 725.8 [M+H]⁺, 363.8 [½ M+H]⁺.

¹H NMR (300 MHz, CD₃OD) δ 7.44 (dd, J=8.4 Hz, 2.1 Hz, 1H), 7.08 (dd, J=8.1 Hz, 2.4 Hz, 1H), 6.93-6.86 (m, 2H), 6.75 (dd, J=8.4 Hz, 2.7 Hz, 1H), 6.67 (s, 1H), 6.54 (d, 1H), 6.38 (dd, J=8.4 Hz, 2.4 Hz, 1H), 6.01 (s, 1H), 3.99 (m, 1H), 3.88 (s, 3H), 3.69 (s, 3H), 3.36 (s, 3H), 3.33 (s, 3H), 3.32 (s, 3H), 2.63 (s, 3H), 2.22 (s, 3H), 1.28 (s, 3H).

Compound BS-TE-408 is prepared by reacting 5-chloromethyltetrandrine with 4-fluorobenzyl alcohol using the same alkaline reagents and solvents according to the process for preparing BS-TE-418.

LC-MS 1.36 min (83.62%). m/z 761.9 [M+H]⁺, 382.0 [½ M+H]⁺.

¹H NMR (300 MHz, CD₃OD) δ 7.44 (dd, J=8.1 Hz, 2.1 Hz, 1H), 7.38-7.33 (m, 2H), 7.08-7.02 (m, 3H), 6.92 (m, 1H), 6.85 (dd, J=8.1 Hz, 2.1 Hz, 1H), 6.75 (dd, J=8.4 Hz, 2.4 Hz, 1H), 6.66 (s, 1H), 6.54 (d, 1H), 6.38 (dd, J=8.4 Hz, 2.4 Hz, 1H), 6.01 (s, 1H), 4.52 (m, 4H), 3.96 (m, 1H), 3.88 (s, 3H), 3.65 (s, 3H), 3.35 (s, 3H), 3.21 (s, 3H), 2.62 (s, 3H), 2.49 (d, 1H), 2.24 (s, 3H).

Compound BS-TE-411 is prepared by reacting 5-chloromethyltetrandrine with 3-pyridinemethanol using the same alkaline reagents and solvents according to the process for preparing BS-TE-418.

LC-MS 1.08 min (85.44%). m/z 744.9 [M+H]⁺, 373.4 [½ M+H]⁺.

¹H NMR (300 MHz, CD₃OD) δ 8.51 (d, 2H), 8.22 (dd, J=8.1 Hz, 1.8 Hz, 1H), 7.81 (d, 1H), 7.46 (m, 2H), 7.08 (dd, J=8.1 Hz, 2.4 Hz, 1H), 6.92 (m, 1H), 6.85 (dd, J=8.4 Hz, 2.1 Hz, 1H), 6.76 (dd, J=8.4 Hz, 2.4 Hz, 1H), 6.66 (s, 1H), 6.54 (d, 1H), 6.38 (dd, J=8.4 Hz, 2.1 Hz, 1H), 6.01 (s, 1H), 4.59 (d, 2H), 3.99 (m, 1H), 3.88 (s, 3H), 3.66 (s, 3H), 3.35 (s, 3H), 3.22 (s, 3H), 2.62 (s, 3H), 2.49 (d, 1H), 2.24 (s, 3H).

Compound BS-TE-415 is prepared by reacting 5-chloromethyltetrandrine with 3-thiophenemethanol using the same alkaline reagents and solvents according to the process for preparing BS-TE-418.

LC-MS 1.31 min (95.23%). m/z 749.8 [M+H]⁺, 375.9 [½ M+H]⁺.

¹H NMR (300 MHz, CD₃OD) δ 7.46 (dd, J=8.4 Hz, 2.4 Hz, 1H), 7.38 (m, 1H), 7.33 (m, 1H), 7.09-7.04 (m, 2H), 6.92 (m, 1H), 6.85 (dd, J=8.4 Hz, 1.8 Hz, 1H), 6.76 (dd, J=7.8 Hz, 1.8 Hz, 1H), 6.68 (s, 1H), 6.54 (d, 1H), 6.39 (dd, J=8.4 Hz, 2.1 Hz, 1H), 6.03 (s, 1H), 4.55 (m, 3H), 3.99 (m, 1H), 3.89 (s, 3H), 3.66 (s, 3H), 3.36 (s, 3H), 3.22 (s, 3H), 2.66 (s, 3H), 2.50 (d, 1H), 2.26 (s, 3H).

Compound BS-TE-416 is prepared by reacting 5-chloromethyltetrandrine with 3-methoxypropanol using the same alkaline reagents and solvents according to the process for preparing BS-TE-418.

LC-MS 1.22 min (92.15%). m/z 725.9 [M+H]⁺, 363.8 [½ M+H]⁺.

¹H NMR (300 MHz, CD₃OD) δ 7.44 (dd, J=8.1 Hz, 2.4 Hz, 1H), 7.07 (dd, J=8.4 Hz, 2.4 Hz, 1H), 6.90 (d, 1H), 6.85 (dd, J=8.1 Hz, 1.8 Hz, 1H), 6.75 (dd, J=8.1 Hz, 2.4 Hz, 1H), 6.67 (s, 1H), 6.54 (d, 1H), 6.40 (dd, J=8.1 Hz, 2.1 Hz, 1H), 6.01 (s, 1H), 4.55 (m, 3H), 3.99 (m, 1H), 3.88 (s, 3H), 3.68 (s, 3H), 3.54 (t, 2H), 3.44 (t, 2H), 3.36 (s, 3H), 3.21 (s, 3H), 2.63 (s, 3H), 2.50 (d, 1H), 2.26 (s, 3H).

Compound BS-TE-417 is prepared by reacting 5-chloromethyltetrandrine with 3-tetrahydrofuranmethanol using the same alkaline reagents and solvents according to the process for preparing BS-TE-418.

LC-MS 1.20 min (99.34%). m/z 737.9 [M+H]⁺, 369.8 [½ M+H]⁺.

¹H NMR (300 MHz, CD₃OD) δ 7.46 (dd, J=7.8 Hz, 2.1 Hz, 1H), 7.07 (dd, J=8.1 Hz, 2.7 Hz, 1H), 6.90 (d, 1H), 6.85 (dd, J=7.8 Hz, 1.8 Hz, 1H), 6.75 (dd, J=8.1 Hz, 2.4 Hz, 1H), 6.66 (s, 1H), 6.55 (d, 1H), 6.40 (dd, J=8.1 Hz, 2.1 Hz, 1H), 6.01 (s, 1H), 4.50 (m, 2H), 3.99 (m, 1H), 3.88 (s, 3H), 3.68 (s, 3H), 3.36 (s, 3H), 3.21 (s, 3H), 2.62 (s, 3H), 2.50 (d, 1H), 2.24 (s, 3H).

Compound BS-TE-419 is prepared by reacting 5-chloromethyltetrandrine with ethanol using the same alkaline reagents and solvents according to the process for preparing BS-TE-418.

LC-MS 1.22 min (96.86%). m/z 681.9 [M+H]⁺, 341.8 [½ M+H]⁺.

¹H NMR (300 MHz, CD₃OD) δ 7.50 (dd, J=8.4 Hz, 2.1 Hz, 1H), 7.09 (dd, J=8.1 Hz, 2.7 Hz, 1H), 6.96 (d, 1H), 6.90 (dd, J=8.1 Hz, 1.8 Hz, 1H), 6.84 (dd, J=8.1 Hz, 2.4 Hz, 1H), 6.79 (s, 1H), 6.53 (d, 1H), 6.40 (dd, J=8.1 Hz, 2.1 Hz, 1H), 6.11 (s, 1H), 4.61 (s, 2H), 4.41 (m, 1H), 4.10 (d, 1H), 3.90 (s, 3H), 3.70 (s, 3H), 3.58 (t, 2H), 3.42 (s, 3H), 3.26 (s, 3H), 2.89 (s, 3H), 2.68 (d, 1H), 2.47 (s, 3H).

Compound BS-TE-420 is prepared by reacting 5-chloromethyltetrandrine with cyclopropylamine using the same alkaline reagents and solvents according to the process for preparing BS-TE-418.

LC-MS 1.21 min (100%). m/z 667.8 [M+H]⁺, 334.8 [½ M+H]⁺.

¹H NMR (300 MHz, CD₃OD) δ 7.50 (dd, J=8.1 Hz, 2.1 Hz, 1H), 7.08 (dd, J=8.1 Hz, 2.4 Hz, 1H), 6.94 (d, 1H), 6.85 (dd, J=8.1 Hz, 1.8 Hz, 1H), 6.75 (dd, J=8.4 Hz, 2.7 Hz, 1H), 6.74 (s, 1H), 6.54 (d, 1H), 6.45 (dd, J=8.4 Hz, 2.1 Hz, 1H), 6.07 (s, 1H), 4.50 (s, 2H), 4.24 (q, 1H), 3.89 (s, 3H), 3.70 (s, 3H), 3.40 (s, 3H), 3.36 (s, 3H), 3.24 (s, 3H), 2.80 (s, 3H), 2.60 (d, 1H), 2.37 (s, 3H).

Compound BS-TE-421 is prepared by reacting 5-chloromethyltetrandrine with thiophenol using the same alkaline reagents and solvents according to the process for preparing BS-TE-418.

LC-MS 1.41 min (97.69%). m/z 746.5[M+H]⁺, 373.8 [½ M+H]⁺.

Example 5

Evaluation of the 5-Substituted Tetrandrine Derivatives of the Present Invention for their Anti-Leukemia Activities (1) Experimental Materials Leukemia cell lines: leukemia cell lines: K562/adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which are donated by Cancer Research Institute of Zhejiang University, China; and H9 (acute lymphoblastic leukemia, ALL), which is purchased from China Center for Type Culture Collection.

Reagents: The standard sample of tetrandrine (TTD) is purchased from Ci Yuan Biotechnology Co., Ltd., Shaanxi, China; and the 5-substituted tetrandrine derivatives of the present invention.

Main apparatuses: a Thermo Scientific 3111 incubator and a Bio-Rad iMark microplate reader.

(2) Experimental Method

Obtaining 6000 well-growing leukemia cells and inoculating them into wells of a 96-well cell culture plate. The culture medium is a 1640 cell culture medium containing 10% fetal bovine serum. After adding the tetrandrine derivatives of different concentrations and mixing uniformly, placing the plate in a carbon dioxide cell incubator (5% $CO_2$) at 37° C. and incubating for 72 hours. Then the viable cell concentration is determined by the MTT method. In this experiment, the cell viability in control group (not treated with any compound) is set as 100%, and the cell viability (%) after treatment and the half maximal inhibitory concentration of the compound for the leukemia cell growth at 72 hours ($IC_{50}$ value and $IC_{90}$ of 72 hours) are calculated.

(3) The Experimental Results

The experimental results are shown in Table 1. Table 1 shows that the 5-substituted tetrandrine derivatives of the present invention can induce the cell death of human chronic myeloid leukemia cells, acute myeloid leukemia cells and acute lymphocytic leukemia cells and inhibit the growth of these leukemia cells. Compared with tetrandrine itself, the 5-substituted tetrandrine derivatives of the present invention exhibit significantly enhanced anti-leukemia cell activities, wherein the anti-K562/adr (drug-resistant, chronic myeloid leukemia, CML) activity of the 5-substituted tetrandrine derivative BS-TE-329 of the present invention increases by almost 4-fold; the anti-Kasumi-1 (acute myeloid leukemia M2 type, AML-M2) activity of BS-TE-305, BS-TE-321, BS-TE-329, BS-TE-346, BS-TE-350, BS-TE-354, BS-TE-355, BS-TE-359 and BS-TE-360 increases 3- to 4-fold over tetrandrine; the anti-Jurkat (acute lymphoblastic leukemia, ALL) activity of BS-TE-346, BS-TE-350, BS-TE-354, BS-TE-355, BS-TE-358 and BS-TE-360 increases almost 4-fold over tetrandrine; the anti-NB4 (acute promyelocytic leukemia, AML) activity of BS-TE-402 increases by almost 8-fold; and the anti-H9 (acute lymphoblastic leukemia, ALL) activity of BS-TE-360 and BS-TE-402 increases by almost 12-fold over tetrandrine.

TABLE 1

Determination of the inhibiting concentrations of the 5-substituted tetrandrine derivatives on leukemia, human multiple myeloma and lymphoma cell growth (72 h, $IC_{50}$ (μg/mL) value and $IC_{90}$ (μg/mL) value).

| Compound ID | K562/ADR | | Kasumi-1 | | Jurkat | |
|---|---|---|---|---|---|---|
| | $IC_{50}$ | $IC_{90}$ | $IC_{50}$ | $IC_{90}$ | $IC_{50}$ | $IC_{90}$ |
| TTD | 0.44 | 2.14 | 1.69 | 8.24 | 2.09 | 9.85 |
| BS-TE-204 | 1.47 | 14.50 | 2.32 | 7.50 | 2.66 | 9.06 |
| BS-TE-213 | 3.70 | 11.11 | 7.74 | >16 | >16 | >16 |
| BS-TE-215 | 2.18 | 8.89 | 4.92 | 15.51 | 4.64 | 10.92 |
| BS-TE-216 | 3.06 | 16.00 | 3.15 | 8.98 | 2.52 | 8.03 |
| BS-TE-223 | 0.50 | 9.91 | 2.00 | 8.00 | 3.42 | 11.26 |
| BS-TE-224 | 0.67 | 4.65 | 3.19 | 7.36 | 3.39 | 7.65 |
| BS-TE-301 | 0.49 | 2.81 | 1.67 | 5.53 | 1.09 | 6.61 |
| BS-TE-305 | 0.44 | 7.20 | 0.52 | 3.11 | 1.35 | 4.96 |
| BS-TE-307 | 0.25 | 7.80 | 1.00 | 4.79 | 3.08 | 13.25 |
| BS-TE-308 | 3.54 | 12.36 | 1.76 | 8.69 | 3.91 | 12.74 |
| BS-TE-311 | 1.97 | 12.00 | 1.33 | 5.63 | 3.15 | 9.19 |
| BS-TE-315 | 4.78 | 10.42 | 1.99 | 7.72 | 4.53 | 11.04 |
| BS-TE-317 | 0.36 | 1.58 | 0.88 | 3.57 | 1.13 | 4.75 |
| BS-TE-320 | 0.84 | 3.36 | 0.78 | 3.65 | 2.00 | 6.19 |
| BS-TE-321 | 0.49 | 3.02 | 0.48 | 2.55 | 0.94 | 5.75 |
| BS-TE-322 | 1.10 | 3.24 | 1.22 | 3.83 | 1.67 | 3.97 |
| BS-TE-323 | 0.21 | 2.16 | 1.23 | 4.60 | 1.28 | 9.00 |
| BS-TE-326 | 0.89 | 2.14 | 0.96 | 2.37 | 1.41 | 3.98 |
| BS-TE-328 | 1.46 | 5.12 | 0.84 | 3.76 | 2.09 | 8.00 |
| BS-TE-329 | 0.10 | 1.33 | 0.50 | 3.40 | 0.91 | 3.31 |
| BS-TE-330 | 0.56 | 2.83 | 1.45 | 6.95 | 2.37 | 5.51 |
| BS-TE-333 | 0.43 | 1.91 | 0.77 | 3.29 | 0.81 | 4.18 |
| BS-TE-334 | 1.49 | 5.99 | 1.06 | 3.64 | 1.88 | 7.85 |
| BS-TE-340 | 0.98 | 2.39 | 0.66 | 1.80 | 2.24 | 4.00 |
| BS-TE-341 | 1.80 | 16.00 | 5.64 | 16.00 | 9.14 | >16 |
| BS-TE-342 | 0.55 | 2.15 | 0.75 | 3.10 | 0.80 | 4.05 |
| BS-TE-343 | 0.68 | 2.38 | 2.24 | 6.95 | 1.90 | 5.27 |
| BS-TE-346 | 0.31 | 2.05 | 0.50 | 2.68 | 0.58 | 3.79 |
| BS-TE-348 | 1.45 | 5.70 | 1.96 | 7.37 | 1.82 | 9.94 |
| BS-TE-350 | 0.33 | 1.60 | 0.54 | 2.52 | 0.59 | 2.97 |
| BS-TE-351 | 0.82 | 3.11 | 0.76 | 3.59 | 1.00 | 5.02 |
| BS-TE-352 | 0.63 | 3.00 | 1.10 | 4.84 | 1.38 | 4.74 |
| BS-TE-354 | 0.99 | 2.65 | 0.37 | 1.97 | 0.50 | 2.23 |
| BS-TE-355 | 0.44 | 8.50 | 0.46 | 2.55 | 0.48 | 4.52 |
| BS-TE-356 | 0.79 | 2.40 | 1.24 | 3.20 | 1.41 | 5.41 |
| BS-TE-358 | 0.63 | 3.15 | 1.10 | 3.71 | 0.55 | 4.00 |
| BS-TE-359 | 0.36 | 2.18 | 0.42 | 1.83 | 0.65 | 5.00 |
| BS-TE-360 | 0.33 | 2.40 | 0.41 | 2.28 | 0.50 | 4.50 |
| BS-TE-361 | 1.64 | 4.00 | 0.80 | 2.78 | | |
| BS-TE-402 | 0.83 | 2.55 | 1.29 | 4.77 | 2.34 | 5.60 |
| BS-TE-403 | 0.72 | 3.07 | 0.78 | 3.42 | 1.29 | 5.68 |
| BS-TE-406 | 1.44 | 5.38 | 1.33 | 6.67 | 1.57 | 9.90 |
| BS-TE-408 | 0.87 | 2.78 | 2.52 | 8.00 | 2.94 | 6.94 |
| BS-TE-411 | 0.79 | 3.59 | 0.75 | 3.58 | 1.00 | 8.50 |
| BS-TE-415 | 0.57 | 2.06 | 1.95 | 6.41 | 2.22 | 5.71 |
| BS-TE-416 | 0.98 | 5.59 | 2.11 | 8.17 | 3.45 | 11.68 |
| BS-TE-417 | 0.88 | 4.63 | 1.80 | 9.69 | 3.64 | 12.13 |
| BS-TE-418 | 1.53 | 3.91 | 1.46 | 7.46 | 2.98 | 13.81 |
| BS-TE-419 | 1.42 | 5.71 | 3.62 | 11.82 | 4.18 | 10.34 |
| BS-TE-420 | 0.82 | 3.85 | 2.16 | 9.83 | 5.21 | 15.99 |
| BS-TE-421 | 0.90 | 7.91 | 3.02 | 7.51 | | |

| Compound ID | NB4 | | H9 | |
|---|---|---|---|---|
| | $IC_{50}$ | $IC_{90}$ | $IC_{50}$ | $IC_{90}$ |
| TTD | 1.60 | 4.10 | 2.69 | 6.40 |
| BS-TE-204 | | | 2.88 | 5.84 |
| BS-TE-213 | | | >16 | >16 |
| BS-TE-215 | 2.60 | 4.00 | 4.86 | 7.60 |
| BS-TE-216 | 1.40 | 2.00 | 2.53 | 7.29 |
| BS-TE-223 | 2.57 | 7.42 | 4.19 | 8.89 |
| BS-TE-224 | | | 2.99 | 4.75 |
| BS-TE-301 | 0.80 | 2.00 | 1.02 | 2.12 |
| BS-TE-305 | 0.29 | 2.00 | 0.70 | 1.44 |
| BS-TE-307 | 0.73 | 4.35 | 0.87 | 1.99 |
| BS-TE-308 | 1.43 | 6.61 | 1.70 | 4.68 |
| BS-TE-311 | 0.83 | 4.00 | 2.29 | 3.99 |
| BS-TE-315 | 1.63 | 5.66 | 2.60 | 4.83 |
| BS-TE-317 | 0.90 | 2.10 | 0.70 | 1.11 |
| BS-TE-320 | | | 1.98 | 3.36 |
| BS-TE-321 | 0.80 | 1.90 | 0.91 | 1.78 |
| BS-TE-322 | 0.83 | 3.48 | 1.08 | 2.19 |
| BS-TE-323 | 1.50 | 4.50 | 0.95 | 2.13 |
| BS-TE-326 | 1.20 | 1.80 | 0.88 | 1.35 |
| BS-TE-328 | 1.80 | 4.40 | 1.54 | 3.15 |
| BS-TE-329 | 2.05 | 3.90 | 1.19 | 2.00 |
| BS-TE-330 | | | 2.03 | 4.03 |
| BS-TE-333 | 0.48 | 1.00 | 1.14 | 1.84 |
| BS-TE-334 | >16 | >16 | 1.30 | 2.40 |
| BS-TE-340 | 1.07 | 2.87 | 1.93 | 3.23 |
| BS-TE-341 | | | 6.87 | 22.12 |
| BS-TE-342 | 0.60 | 1.60 | 1.11 | 2.32 |
| BS-TE-343 | 1.18 | 3.06 | 1.62 | 2.75 |
| BS-TE-346 | 0.54 | 1.50 | 1.01 | 2.30 |

TABLE 1-continued

Determination of the inhibiting concentrations of the 5-substituted tetrandrine derivatives on leukemia, human multiple myeloma and lymphoma cell growth (72 h, $IC_{50}$ (μg/mL) value and $IC_{90}$ (μg/mL) value).

| | | | | |
|---|---|---|---|---|
| BS-TE-348 | 1.14 | 4.78 | 1.33 | 2.97 |
| BS-TE-350 | 0.30 | 1.00 | 1.11 | 1.92 |
| BS-TE-351 | 0.70 | 1.90 | 0.72 | 1.58 |
| BS-TE-352 | 1.05 | 3.88 | 1.31 | 4.50 |
| BS-TE-354 | 0.40 | 1.00 | 0.78 | 1.25 |
| BS-TE-355 | 0.40 | 1.40 | 0.63 | 1.96 |
| BS-TE-356 | 0.63 | 2.17 | 1.54 | 2.21 |
| BS-TE-358 | 0.80 | 2.00 | 1.45 | 2.40 |
| BS-TE-359 | 0.40 | 1.00 | 1.25 | 2.30 |
| BS-TE-360 | 0.50 | 1.40 | 0.22 | 1.71 |
| BS-TE-402 | 0.20 | 1.41 | 0.25 | 1.25 |
| BS-TE-403 | 1.10 | 2.70 | 1.22 | 2.20 |
| BS-TE-406 | 1.70 | 5.50 | 1.38 | 3.41 |
| BS-TE-408 | | | 2.50 | 3.99 |
| BS-TE-411 | 0.70 | 2.60 | 1.23 | 2.50 |
| BS-TE-415 | | | 1.71 | 2.50 |
| BS-TE-416 | | | 2.31 | 4.40 |
| BS-TE-417 | | | 2.03 | 4.37 |
| BS-TE-418 | | | 2.38 | 5.00 |
| BS-TE-419 | | | 4.64 | 7.26 |
| BS-TE-420 | | | 4.40 | 7.68 |

Example 6

Evaluation of the 5-Substituted Tetrandrine Derivatives of the Present Invention for their Anti-Human Multiple Myeloma and Anti-Lymphoma Cell Activities (1) Experimental Materials Multiple myeloma and lymphoma cell lines: RPMI8226 (multiple myeloma), purchased from Fuxiang Bio-tech Co. Ltd., Shanghai, China.

Reagents: the same as in Example 5.

Main apparatuses: a Thermo Scientific 3111 incubator and a Bio-Rad iMark microplate reader.

(2) Experimental Method

Obtaining 6000 well-growing leukemia cells and inoculating them into wells of a 96-well cell culture plate. The culture medium is a 1640 cell culture medium containing 10% fetal bovine serum. After adding the tetrandrine derivatives of different concentrations and mixing uniformly, placing the plate in a carbon dioxide cell incubator (5% $CO_2$) at 37° C. and incubated for 72 hours. Then the viable cell concentration is determined by the MTT method. In this experiment, the cell viability in control group (not treated with any compound) is set as 100% and the cell viability (% after treatment and the half maximal inhibitory concentration of the compound for the leukemia cell growth at 72 hours ($IC_{50}$ and $IC_{90}$ values of 72 hours) are calculated.

(3) The Experimental Results

The experimental results are shown in table 2. Table 2 shows that the 5-substituted tetrandrine derivatives of the present invention can induce the cell death of human myeloma and lymphoma cells and inhibit the growth of these tumor cells, wherein the anti-RPMI8226 (multiple myeloma) activity of the 5-substituted tetrandrine derivatives BS-TE-305 and BS-TE-342 of the present invention increases by more than 60-fold over tetrandrine, and the anti-RPMI8226 (multiple myeloma) activity of BS-TE-329 increases by almost 90-fold.

Example 7

Evaluation of the 5-Substituted Tetrandrine Derivatives of the Present Invention for their Anti-Human Solid Tumor Effect (1) Experimental Materials Human solid tumor cell lines: Hep-2 (laryngeal carcinoma), A549 (human lung cancer), CaES-17 (esophageal cancer cell), PC-3 (prostate cancer), CNE (nasopharyngeal carcinoma cell) and SK-OV-3 (ovarian cancer cell), all of which are purchased from China Center For Type Culture Collection; RKO (human colon adenocarcinoma cell), MGC 803 (human gastric cancer cell), MG63 (osteosarcoma), and U87 MG (malignant glioma cell), all of which are purchased from Fuxiang Bio-tech Co. Ltd., Shanghai, China; PANC-1 (pancreatic cancer), Huh? (human liver cancer cell), Becap37 (human breast cancer cell), and Hela (human cervical cancer cell), all of which are donated by Cancer Research Institute of Zhejiang University, China.

Reagents: the same as in Example 5.

Main apparatuses: a Thermo Scientific 3111 incubator and a Bio-Rad iMark microplate reader.

(2) Experimental Method

Obtaining 4000 well-growing human solid tumor cells and inoculating them into wells of a 96-well cell culture plate. The culture medium is DMEM High Glucose cell culture medium containing 10% fetal bovine serum. The plate is placed in a carbon dioxide cell incubator (5% $CO_2$) at 37° C. and incubated for 24 hours. After been added with tetrandrine derivatives of different concentration and mixing uniformly, the plate is placed in a carbon dioxide cell incubator (5% $CO_2$) at 37° C. and incubated for 72 hours. Then the viable cell concentration is determined by the MTT method and the cell viability (%) after drug treatment is calculated. In this experiment, the cell viability of control group (not treated with any compound) is set as 100%.

(3) The Experimental Results are Shown in Table 2.

The experimental results are shown in table 2. Table 2 shows that the 5-substituted tetrandrine derivatives of the present invention can induce the cell death of human solid tumor cells and inhibit the growth of these tumor cells. In comparison with tetrandrine per se, the 5-substituted tetrandrine derivatives of the present invention exhibit distinctly enhanced anti-human solid tumor cell activity, wherein the anti-A549 (human lung cancer) activity of BS-TE-305 increases by almost 3-fold; the anti-PANC-1 (pancreatic cancer) activity of BS-TE-317 and BS-TE-354 increases by 2-fold; the anti-Huh7 (human liver cancer cell) activity of BS-TE-354 increases by almost 8-fold; the anti-MGC 803 (human gastric cancer cell) activity of BS-TE-317, BS-TE-333, BS-TE-346, BS-TE-350, BS-TE-354, BS-TE-355, BS-TE-359 and BS-TE-360 increases by more than 2-fold; the anti-Becap37 (human breast cancer cell) activity of BS-TE-354 and BS-TE-402 increases by 17-fold and 13-fold, respectively; the anti-PC-3 (prostate cancer) activity of BS-TE-305 and BS-TE-317 increases by almost 4-fold; the anti-RKO (human colon adenocarcinoma cell) activity of BS-TE-360 and BS-TE-402 increases by 22-fold and 16-fold, respectively; the anti-Hep-2 (laryngeal carcinoma), anti-CaES-17 (esophageal cancer cell), anti-MG63 (osteosarcoma) and anti-Hela (human cervical cancer cell) activity of BS-TE-402 increases by 7-fold, 14-fold, 27-fold and 9-fold, respectively; the anti-U87 MG (malignant glioma cell) activity of BS-TE-342, BS-TE-350, BS-TE-351, BS-TE-354, BS-TE-359 and BS-TE-360 increases by more than 2-fold; the anti-CNE (nasopharyngeal carcinoma cell) activity of BS-TE-354 and BS-TE-360 increases by 5- to 6-fold; and the anti-SK-OV-3 (ovarian cancer cell) of BS-TE-354 and BS-TE-402 also increases by more than 6-fold.

TABLE 2

Determination of the inhibitory concentrations of the tetrandrine derivatives on human solid tumor cell growth (72 h, $IC_{50}$ (μg/mL) value and $IC_{90}$ (μg/mL) value)

| Compound ID | RPMI8226 | | A549 | | PANC-1 | | MGC-803 | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TTD | 0.37 | 2.54 | 2.9 | 12.5 | 3.16 | 7.02 | 1.97 | 7.41 |
| BS-TE-204 | 0.47 | 1.92 | 3.12 | 14.18 | 6.47 | 11.08 | 2.57 | 9.00 |
| BS-TE-213 | 1.95 | 8 | >16 | >16 | >10 | >10 | 18.95 | 64.43 |
| BS-TE-215 | 0.87 | 5.13 | 11.90 | >16 | 5.11 | 15.00 | 5.78 | 8.00 |
| BS-TE-216 | 0.54 | 3.14 | 8.60 | >16 | 15.77 | >16 | 2.51 | 4.00 |
| BS-TE-223 | 0.23 | 2.29 | 4.45 | 14.20 | 10.73 | 16.00 | 3.54 | 38.06 |
| BS-TE-224 | 0.27 | 1.44 | >16 | >16 | 5.68 | 8.76 | 2.45 | 3.72 |
| BS-TE-301 | 0.06 | 2.95 | 5.10 | >16 | 2.79 | 7.35 | 1.74 | 7.10 |
| BS-TE-305 | 0.006 | 0.42 | 1.00 | 5.25 | 3.72 | 13.43 | 1.00 | 10.00 |
| BS-TE-307 | 0.07 | 0.42 | 2.30 | 8.00 | 3.47 | 8.88 | 3.74 | 14.14 |
| BS-TE-308 | 0.28 | 0.76 | 2.79 | 11.15 | 6.54 | 14.68 | 4.44 | 23.00 |
| BS-TE-311 | 0.18 | 1.74 | 1.89 | 9.07 | 6.31 | 13.18 | 3.17 | 11.79 |
| BS-TE-315 | 0.30 | 2.07 | 1.96 | 9.36 | 5.89 | 14.68 | 3.63 | 10.46 |
| BS-TE-317 | 0.06 | 1.49 | 2.20 | 5.80 | 1.40 | 4.18 | 0.73 | 1.00 |
| BS-TE-320 | 0.06 | 2 | 2.98 | 7.85 | 3.52 | 9.25 | 1.72 | 2.76 |
| BS-TE-321 | 0.08 | 3.63 | 4.40 | 16.00 | 2.60 | 9.14 | 1.78 | 6.73 |
| BS-TE-322 | 0.14 | 0.7 | 1.83 | 6.34 | 3.29 | 5.41 | 2.29 | >10 |
| BS-TE-323 | 0.12 | 3.88 | 6.20 | 16.00 | 2.46 | 7.10 | 3.04 | 8.00 |
| BS-TE-326 | 0.27 | 0.64 | 1.80 | 4.90 | 1.63 | 5.16 | 1.46 | 5.38 |
| BS-TE-328 | 0.15 | 0.96 | 3.70 | 9.90 | 2.99 | 7.15 | 1.68 | 4.00 |
| BS-TE-329 | 0.004 | 0.29 | 2.36 | 4.77 | >10 | >10 | 1.26 | 1.82 |
| BS-TE-330 | 0.18 | 1.22 | 5.44 | 15.96 | 6.17 | 9.80 | 1.61 | 6.48 |
| BS-TE-333 | 0.06 | 2.34 | 1.50 | 11.00 | 1.69 | 9.93 | 0.84 | 5.30 |
| BS-TE-334 | 0.05 | 1.11 | 4.00 | 14.61 | 3.99 | 11.00 | 2.22 | 10.00 |
| BS-TE-340 | 0.18 | 0.999 | 2.36 | 6.66 | 3.61 | 5.72 | 2.34 | 5.54 |
| BS-TE-341 | 0.35 | 3.31 | >16 | >16 | >10 | >10 | 9.67 | 15.10 |
| BS-TE-342 | 0.006 | 0.45 | 3.20 | 16.00 | 1.92 | 6.84 | 1.38 | 6.55 |
| BS-TE-343 | 0.05 | 0.7 | 3.54 | 11.97 | 2.84 | 4.84 | 1.10 | 2.88 |
| BS-TE-346 | 0.02 | 0.06 | 2.50 | 8.00 | 2.31 | 8.26 | 0.90 | 4.98 |
| BS-TE-348 | 0.09 | 1 | 9.94 | >16 | 4.55 | 13.92 | 1.93 | 5.53 |
| BS-TE-350 | 0.05 | 1.51 | 3.00 | 11.00 | 1.83 | 6.04 | 0.89 | 4.11 |
| BS-TE-351 | 0.09 | 2.43 | 3.90 | 16.00 | 1.87 | 7.79 | 1.49 | 7.42 |
| BS-TE-352 | 0.09 | 0.76 | 1.35 | 4.58 | 5.79 | 9.00 | 4.38 | >10 |
| BS-TE-354 | 0.08 | 1.58 | 1.80 | 9.80 | 1.25 | 6.31 | 0.83 | 3.93 |
| BS-TE-355 | 0.04 | 3.08 | 3.40 | 14.90 | 2.27 | 8.22 | 0.92 | 12.00 |
| BS-TE-356 | 0.11 | 2.43 | 3.50 | 10.52 | 1.62 | 4.58 | 1.26 | 1.88 |
| BS-TE-358 | 0.08 | 3.69 | 4.00 | 16.00 | 2.66 | 9.71 | 1.39 | 7.08 |
| BS-TE-359 | 0.05 | 1.42 | 3.30 | 12.80 | 2.44 | 8.04 | 0.88 | 6.00 |
| BS-TE-360 | 0.05 | 1.5 | 1.70 | 9.20 | 1.88 | 9.54 | 0.80 | 5.17 |
| BS-TE-361 | | | 1.66 | 5.10 | 5.07 | 10.67 | | |
| BS-TE-402 | 0.25 | 1.17 | 1.35 | 4.79 | 1.34 | 4.04 | 1.50 | 3.62 |
| BS-TE-403 | 0.29 | 1.26 | 4.96 | 11.70 | 1.74 | 5.66 | 2.47 | 7.05 |
| BS-TE-406 | 0.52 | 2.81 | 8.40 | >16 | 2.73 | 16.00 | 2.87 | 8.00 |
| BS-TE-408 | 0.23 | 1.13 | 3.10 | 7.05 | 6.00 | 9.90 | 2.59 | 3.97 |
| BS-TE-411 | 0.26 | 1.35 | 5.50 | 15.50 | 2.29 | 8.92 | 2.15 | 9.02 |
| BS-TE-415 | 0.14 | 0.89 | 2.44 | 5.61 | 2.76 | 4.90 | 1.06 | 1.90 |
| BS-TE-416 | 0.29 | 2.76 | 4.05 | 10.96 | 4.63 | 10.00 | 5.17 | 8.33 |
| BS-TE-417 | 0.27 | 2 | 3.88 | 10.11 | 4.66 | 9.50 | 5.09 | 8.27 |
| BS-TE-418 | 0.15 | 2.12 | 4.50 | 11.04 | 4.57 | 9.50 | 4.40 | 6.85 |
| BS-TE-419 | 0.28 | 2.09 | 5.61 | 9.75 | 5.99 | 9.31 | 5.16 | 7.50 |
| BS-TE-420 | 0.29 | 2.25 | 4.41 | 12.17 | >10 | >10 | 5.01 | 7.56 |
| BS-TE-421 | 0.19 | 1.28 | 3.40 | 8.00 | 3.76 | 6.73 | 3.44 | 4.80 |

| Compound ID | Becap-37 | | PC-3 | | Huh-7 | | RKO | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TTD | 6.9 | 15 | 6.01 | 10.78 | 5.05 | 7.81 | 2.72 | 6.3 |
| BS-TE-204 | 3.66 | 6.19 | 6.55 | 9.00 | 2.08 | 3.88 | 3.12 | 4.70 |
| BS-TE-213 | 9.95 | >10 | >10 | >10 | 8.54 | 15.09 | | |
| BS-TE-215 | 8.30 | 15.00 | 7.08 | 9.00 | 3.54 | 9.62 | 6.04 | 9.22 |
| BS-TE-216 | 5.80 | 13.00 | 4.11 | 7.84 | 2.66 | 4.71 | 2.21 | 4.67 |
| BS-TE-223 | 6.77 | 15.00 | 5.60 | 27.97 | 4.14 | 7.97 | 4.23 | 7.50 |
| BS-TE-224 | 2.85 | 4.18 | 6.38 | 9.00 | 2.40 | 3.93 | | |
| BS-TE-301 | 2.30 | 5.60 | 3.02 | 4.68 | 1.27 | 2.40 | 1.22 | 2.94 |
| BS-TE-305 | 1.44 | 6.24 | 1.56 | 4.90 | 1.28 | 2.30 | 0.66 | 1.65 |
| BS-TE-307 | 1.79 | 6.94 | 2.88 | 6.99 | 3.00 | 4.90 | 0.95 | 3.27 |
| BS-TE-308 | 4.76 | 11.49 | 5.39 | 8.99 | 3.10 | 4.95 | 1.77 | 4.03 |
| BS-TE-311 | 2.50 | 7.86 | 6.04 | 8.00 | 3.50 | 4.90 | 1.96 | 4.25 |
| BS-TE-315 | 2.95 | 9.79 | 6.41 | 8.00 | 3.07 | 4.98 | 1.64 | 3.39 |
| BS-TE-317 | 1.30 | 3.20 | 1.59 | 2.14 | 1.55 | 3.72 | 1.15 | 2.49 |
| BS-TE-320 | 1.60 | 2.17 | | | 2.00 | 3.92 | | |

TABLE 2-continued

Determination of the inhibitory concentrations of the tetrandrine derivatives on human solid tumor cell growth (72 h, $IC_{50}$ (μg/mL) value and $IC_{90}$ (μg/mL) value)

| Compound ID | | | | | | | | |
|---|---|---|---|---|---|---|---|---|
| BS-TE-321 | 1.40 | 4.50 | 2.01 | 3.84 | 0.81 | 1.24 | 0.69 | 1.71 |
| BS-TE-322 | 2.31 | 4.00 | 2.26 | 4.06 | 1.42 | 1.94 | 0.90 | 2.40 |
| BS-TE-323 | 3.20 | 8.00 | 1.88 | 3.83 | 1.33 | 3.88 | 1.07 | 2.60 |
| BS-TE-326 | 1.30 | 2.00 | 3.60 | 5.80 | 1.15 | 1.76 | 0.87 | 2.22 |
| BS-TE-328 | 2.00 | 4.00 | 3.07 | 4.98 | 1.52 | 3.70 | 1.76 | 3.00 |
| BS-TE-329 | 1.62 | 2.48 | | | 8.16 | 15.87 | | |
| BS-TE-330 | 6.00 | 12.00 | 3.68 | 7.59 | 2.96 | 4.90 | 2.50 | 4.64 |
| BS-TE-333 | 1.00 | 4.50 | 1.85 | 2.90 | 1.64 | 2.45 | 0.54 | 1.74 |
| BS-TE-334 | 3.09 | 8.39 | 3.35 | 6.05 | 2.55 | 4.38 | 0.82 | 2.04 |
| BS-TE-340 | 1.99 | 4.12 | 3.43 | 4.00 | 2.52 | 4.85 | 1.29 | 2.45 |
| BS-TE-341 | 9.80 | >10 | | | 4.71 | 7.88 | | |
| BS-TE-342 | 1.10 | 4.50 | 1.79 | 2.40 | 1.31 | 2.46 | 0.69 | 1.75 |
| BS-TE-343 | 6.96 | 8.17 | 2.72 | 4.28 | 2.14 | 4.85 | 2.25 | 3.24 |
| BS-TE-346 | 0.80 | 2.30 | 2.92 | 4.90 | 1.63 | 2.49 | 0.73 | 1.90 |
| BS-TE-348 | 3.84 | 13.59 | 4.44 | 8.36 | 3.05 | 8.00 | 1.77 | 3.83 |
| BS-TE-350 | 0.90 | 3.60 | 1.87 | 2.83 | 1.82 | 2.43 | 0.45 | 0.92 |
| BS-TE-351 | 1.08 | 4.50 | 1.82 | 3.32 | 1.30 | 2.41 | 0.45 | 1.25 |
| BS-TE-352 | 1.40 | 4.85 | 4.53 | 7.51 | 3.61 | 4.98 | | |
| BS-TE-354 | 0.40 | 2.40 | 1.90 | 2.50 | 0.65 | 0.98 | 0.25 | 0.51 |
| BS-TE-355 | 0.76 | 2.69 | 1.83 | 3.65 | 1.28 | 2.45 | 0.25 | 1.18 |
| BS-TE-356 | 1.63 | 3.00 | 3.40 | 5.00 | 1.30 | 1.67 | 0.51 | 0.91 |
| BS-TE-358 | 1.96 | 4.50 | 3.70 | 5.90 | 1.35 | 1.92 | 0.60 | 1.67 |
| BS-TE-359 | 1.10 | 2.00 | 3.00 | 4.70 | 1.19 | 1.68 | 0.58 | 1.01 |
| BS-TE-360 | 1.20 | 3.70 | 1.85 | 2.50 | 0.93 | 2.40 | 0.12 | 1.02 |
| BS-TE--361 | | | | | 1.24 | 1.88 | | |
| BS-TE-402 | 0.52 | 2.15 | 2.05 | 4.71 | 1.09 | 4.97 | 0.17 | 0.60 |
| BS-TE-403 | 3.30 | 5.80 | 2.68 | 5.43 | 1.87 | 2.40 | 0.89 | 2.04 |
| BS-TE-406 | 3.50 | 10.80 | 3.32 | 6.95 | 2.31 | 3.43 | 0.89 | 1.99 |
| BS-TE-408 | 4.89 | 36.60 | 5.77 | 9.09 | 1.84 | 3.51 | | |
| BS-TE-411 | 1.90 | 4.90 | 2.41 | 5.56 | 1.13 | 1.66 | 0.26 | 0.60 |
| BS-TE-415 | 1.90 | 3.31 | 3.50 | 5.76 | 1.09 | 1.91 | | |
| BS-TE-416 | 1.80 | 4.31 | 4.19 | 9.49 | 2.93 | 5.07 | | |
| BS-TE-417 | 1.77 | 3.79 | 4.10 | 7.91 | 2.48 | 3.76 | | |
| BS-TE-418 | 1.98 | 4.40 | 4.98 | 9.43 | 3.08 | 5.77 | | |
| BS-TE-419 | 4.22 | 6.88 | 6.67 | 10.51 | 2.54 | 6.16 | | |
| BS-TE-420 | 5.60 | 11.50 | 5.68 | 10.95 | 4.22 | 7.06 | | |
| BS-TE-421 | 3.50 | 4.86 | | | 1.52 | 3.27 | | |

| | MG-63 | | CAES-17 | | Hep 2 | | Hela | |
|---|---|---|---|---|---|---|---|---|
| Compound ID | $IC_{50}$ | $IC_{90}$ | $IC_{50}$ | $IC_{90}$ | $IC_{50}$ | $IC_{90}$ | $IC_{50}$ | $IC_{90}$ |
| TTD | 1.9 | 3.7 | 8.34 | >16 | 3.88 | 11.86 | 4.05 | 9.24 |
| BS-TE-204 | 1.72 | 4.69 | 6.81 | 16.61 | | | | |
| BS-TE-213 | 9.93 | 26.11 | 9.89 | 30.16 | | | | |
| BS-TE-215 | 6.20 | 10.40 | 8.69 | 27.04 | 9.90 | 22.22 | 6.52 | 13.03 |
| BS-TE-216 | 4.50 | 8.80 | 5.36 | 29.91 | 5.42 | 16.00 | 3.82 | 10.79 |
| BS-TE-223 | 5.13 | 7.64 | 9.80 | 37.50 | | | | |
| BS-TE-224 | 2.76 | 4.51 | 2.40 | 7.23 | | | | |
| BS-TE-301 | 2.00 | 3.80 | 2.93 | 22.29 | 3.50 | 12.47 | 1.97 | 3.83 |
| BS-TE-305 | 0.74 | 2.05 | 1.10 | 16.97 | | | | |
| BS-TE-307 | 0.82 | 2.32 | 1.10 | 18.81 | | | | |
| BS-TE-308 | 1.38 | 4.84 | 3.43 | 27.42 | | | | |
| BS-TE-311 | 1.89 | 4.00 | 4.05 | 25.61 | | | | |
| BS-TE-313 | 9.77 | 25.90 | 9.90 | 25.30 | | | | |
| BS-TE-315 | 1.41 | 3.11 | 2.40 | 20.84 | | | | |
| BS-TE-317 | 1.30 | 1.90 | 1.61 | 7.40 | 1.96 | 4.25 | 0.94 | 2.02 |
| BS-TE-320 | 1.10 | 2.18 | 2.11 | 12.18 | | | | |
| BS-TE-321 | 1.10 | 3.20 | 2.25 | 19.08 | 3.51 | 9.80 | 1.48 | 4.31 |
| BS-TE-322 | 1.00 | 2.24 | 1.58 | 9.61 | | | | |
| BS-TE-323 | 2.60 | 5.50 | 3.60 | 23.00 | 2.49 | 5.59 | 1.20 | 3.89 |
| BS-TE-326 | 1.40 | 1.90 | 2.50 | 6.18 | 3.62 | 6.57 | 1.90 | 3.01 |
| BS-TE-328 | 2.10 | 3.90 | 3.13 | 12.18 | 9.63 | 15.90 | 2.49 | 4.91 |
| BS-TE-329 | 6.87 | 35.59 | 7.20 | 26.47 | | | | |
| BS-TE-330 | 1.96 | 4.38 | 2.40 | 7.94 | | | | |
| BS-TE-333 | 0.70 | 1.30 | 2.35 | 17.09 | 1.72 | 9.69 | 1.69 | 5.00 |
| BS-TE-334 | 0.84 | 2.44 | 2.35 | 21.49 | | | | |
| BS-TE-340 | 0.60 | 1.19 | 1.83 | 7.21 | | | | |
| BS-TE-341 | 3.16 | 9.80 | 4.80 | 25.79 | | | | |
| BS-TE-342 | 0.90 | 1.90 | 2.21 | 12.38 | 1.86 | 7.19 | 1.69 | 4.10 |
| BS-TE-343 | 1.15 | 2.47 | 2.09 | 8.09 | | | | |
| BS-TE-346 | 0.80 | 1.50 | 1.29 | 7.23 | 1.79 | 6.83 | 1.83 | 5.00 |
| BS-TE-348 | 1.52 | 4.06 | 2.30 | 14.54 | | | | |
| BS-TE-350 | 0.80 | 1.60 | 1.03 | 5.13 | 1.51 | 4.67 | 0.95 | 2.50 |
| BS-TE-351 | 1.20 | 2.00 | 1.38 | 8.19 | 3.07 | 8.13 | 1.25 | 3.61 |
| BS-TE-352 | 1.26 | 4.35 | 3.06 | 9.92 | | | | |

TABLE 2-continued

Determination of the inhibitory concentrations of the tetrandrine derivatives on human solid tumor cell growth (72 h, $IC_{50}$ (μg/mL) value and $IC_{90}$ (μg/mL) value)

| | | | | | | | | |
|---|---|---|---|---|---|---|---|---|
| BS-TE-354 | 0.68 | 0.90 | 0.91 | 4.89 | 2.05 | 6.19 | 1.07 | 2.81 |
| BS-TE-355 | 0.77 | 1.27 | 1.42 | 10.99 | 3.22 | 8.45 | 2.00 | 6.92 |
| BS-TE-356 | 0.49 | 0.62 | 1.00 | 9.26 | 3.37 | 7.54 | 1.55 | 5.00 |
| BS-TE-358 | 1.50 | 2.80 | 2.69 | 10.06 | 3.37 | 7.54 | 2.12 | 3.97 |
| BS-TE-359 | 1.10 | 1.98 | 1.61 | 7.67 | 4.60 | 8.29 | 1.09 | 2.56 |
| BS-TE-360 | 0.80 | 1.90 | 1.75 | 10.47 | 2.40 | 9.39 | 1.20 | 6.00 |
| BS-TE--361 | | | | | | | | |
| BS-TE-402 | 0.07 | 1.11 | 0.60 | 4.90 | 0.58 | 3.58 | 0.45 | 2.29 |
| BS-TE-403 | 2.03 | 4.00 | 2.97 | 8.86 | 2.81 | 5.90 | 1.19 | 3.04 |
| BS-TE-406 | 2.49 | 6.36 | 3.94 | 16.45 | 2.40 | 6.87 | 1.07 | 2.89 |
| BS-TE-408 | 2.88 | 9.84 | 4.80 | 14.94 | | | | |
| BS-TE-411 | 1.26 | 3.07 | 2.76 | 11.79 | 2.15 | 5.69 | 1.49 | 3.45 |
| BS-TE-415 | 1.31 | 4.75 | 1.74 | 5.98 | | | | |
| BS-TE-416 | 1.08 | 2.49 | 2.30 | 16.59 | | | | |
| BS-TE-417 | 1.06 | 3.66 | 2.04 | 12.03 | | | | |
| BS-TE-418 | 1.48 | 4.45 | 1.71 | 9.90 | | | | |
| BS-TE-419 | 3.07 | 9.69 | 4.98 | 18.42 | | | | |
| BS-TE-420 | 2.72 | 9.89 | 4.72 | 18.93 | | | | |
| BS-TE-421 | 1.08 | 4.46 | | | | | | |

| | U87 | | CNE | | SK-OV-3 | |
|---|---|---|---|---|---|---|
| Compound ID | $IC_{50}$ | $IC_{90}$ | $IC_{50}$ | $IC_{90}$ | $IC_{50}$ | $IC_{90}$ |
| TTD | 0.66 | 3.58 | 3.3 | 6.2 | 9.04 | >16 |
| BS-TE-215 | 3.14 | 8.00 | 6.97 | 12.17 | 7.50 | >16 |
| BS-TE-216 | 1.24 | 3.74 | 3.86 | 13.30 | 7.00 | >16 |
| BS-TE-301 | 0.69 | 3.05 | 3.70 | 6.20 | 3.77 | 24.28 |
| BS-TE-317 | 0.50 | 1.81 | 2.30 | 3.50 | 2.00 | 8.10 |
| BS-TE-321 | 0.57 | 2.51 | 2.80 | 6.60 | 3.50 | >16 |
| BS-TE-323 | 0.98 | 4.02 | 4.80 | 10.40 | 8.00 | >16 |
| BS-TE-326 | 0.75 | 2.40 | 3.20 | 4.95 | 1.91 | 5.21 |
| BS-TE-328 | 1.44 | 5.39 | 6.02 | >16 | 6.80 | >16 |
| BS-TE-333 | 0.50 | 1.51 | 2.60 | 5.60 | 3.04 | >16 |
| BS-TE-342 | 0.30 | 1.16 | 1.60 | 3.70 | 2.00 | >16 |
| BS-TE-346 | 0.19 | 0.57 | 2.50 | 5.40 | 3.90 | >16 |
| BS-TE-350 | 0.30 | 1.13 | 1.30 | 3.30 | 1.80 | 12.90 |
| BS-TE-351 | 0.28 | 0.67 | 1.32 | 3.84 | 3.50 | >16 |
| BS-TE-354 | 0.31 | 1.44 | 0.54 | 1.62 | 1.40 | >16 |
| BS-TE-355 | 0.37 | 1.16 | 1.17 | 3.64 | 3.50 | >16 |
| BS-TE-356 | 1.11 | 2.02 | 0.94 | 2.59 | 2.19 | 4.00 |
| BS-TE-358 | 0.65 | 1.99 | 2.26 | 4.12 | 4.00 | >16 |
| BS-TE-359 | 0.33 | 1.01 | 1.57 | 2.83 | 2.00 | 14.40 |
| BS-TE-360 | 0.33 | 1.55 | 0.64 | 3.55 | 1.62 | 3.22 |
| BS-TE-402 | 0.55 | 1.78 | 1.03 | 2.49 | 1.37 | 3.89 |
| BS-TE-403 | 1.35 | 2.45 | 2.12 | 4.46 | 3.50 | 15.10 |
| BS-TE-406 | 2.86 | 6.66 | 1.60 | 3.49 | 7.10 | >16 |
| BS-TE-411 | 1.09 | 2.55 | 1.32 | 3.33 | 8.00 | >16 |

As can be seen from the in vitro experimental data in Examples 6 and 7, all the evaluated compounds of the present invention possess antitumor activity. In comparison with the compound of formula (I-b), the compounds of formula (I-c), formula (I-d) and formula (I-e) possess stronger antitumor activity. It is noted that, the evaluated compounds of formula (I-c), formula (I-d) and formula (I-e) exhibit an $IC_{50}$ value for at least one tumor cell line lower than or equal to that of the control compound TTD.

Example 8

Evaluation of the In Vivo Anti-Tumor Activity of Some 5-Substituted Tetrandrine Derivatives of the Present Invention and Preliminary Evaluation of their Toxicity

Experiment 8-1

The inhibiting effect of BS-TE-403 and BS-TE-333 on the transplanted tumor of human lung cancer in nude mice (1) Experimental Materials Cell lines: human non-small cell lung cancer cell line A549, from China Center for Type Culture Collection (CCTCC);

Animal: BALB/c nude mice, 8 weeks, female, purchased from Shanghai Laboratory Animal Center of Chinese Academy of Sciences, China.

(2) Reagents:

BS-TE-403 and BS-TE-333 (the present invention), and tetrandrine TTD from Jiangxi Jinfurong Pharmaceutical Co., Ltd. All compounds are administered at the dosage of 50 mg/kg weight each time.

(3) Main Apparatuses:

a cell incubator (Thermo Scientific $CO_2$ incubator, Type 3111), a biosafety cabinet (Heal Force, Hfsafe-1200A2) and a laminar flow rack (Suhang Brand clean animal breeding cabinet, Type DJ-2).

(4) Experimental Method

Under sterile conditions, the above tumor cells in the logarithmic growth phase are collected and injected by subcutaneous injection in an amount of $5 \times 10^6/0.2$ ml/nude mice (cell viability>95%) into the right subaxillary of the nude mice, thus establishing a transplanted tumor model of human non-small cell lung cancer in nude mice.

The experiments are divided into 4 groups: negative control group (solvent group), positive control group (lead compound TTD group), BS-TE-403 group and BS-TE-333 group.

The mice are administered from the third day after the inoculation. Each mouse is intragastrically administered in 0.4 ml each time and 3 times a day, at 8:00, 14:00 and 20:00, with 6-hour intervals. The administrations are successive for 10 days. The day before administration is deemed as Day 0 and the body weight and tumor size of the mice are determined every 5 days to produce a dynamic plot on body weight and tumor growth. On Day 27, the mice are dissected and the tumors are taken out and weighed. The tumor inhibition rate (%) is calculated after the effect of the medicament based on a tumor inhibition rate of the control group being zero.

The values determined are presented as mean±standard error (M±SD).

TABLE 3

The effect of BS-TE-403 and BS-TE-333 on transplanted tumors of human lung cancer in the nude mice

| Group | Dosage (mg/kg weight/time) | Number of animals | | Weight (g) | | Mass of tumor (mg) | Tumor Inhibition rate (%) |
|---|---|---|---|---|---|---|---|
| | | Initial | Final | Initial | Final | | |
| Control | | 4 | 4 | 22.33 ± 0.26 | 20.48 ± 2.29 | 928.50 ± 197.72 | — |
| TTD | 50 | 3 | 3 | 22.40 ± 0.26 | 19.10 ± 2.02 | 799.00 ± 349.09 | 13.95 |
| BS-TE-403 | 50 | 4 | 4 | 24.25 ± 0.19 | 21.70 ± 0.92 | 658.50 ± 532.71 | 29.08 |
| BS-TE-333 | 50 | 4 | 4 | 21.3 ± 0.24 | 16.95 ± 2.30 | 639.25 ± 285.20 | 31.15 |

FIG. 1 shows the dynamic change of the effect of BS-TE-403 and BS-TE-333 on the body weight of nude mice. As is shown in FIG. 1, the weight loss in the BS-TE-403 group is not appreciable as compared with the weight in the control group, indicating that BS-TE-403 has not yet caused any obvious toxic or side effect under such a dosage. The weight loss in the BS-TE-333 group is relatively obvious as compared with the weight in the control group, indicating that BS-TE-333 has caused some toxic and side effect under such a dosage.

Figure 2:
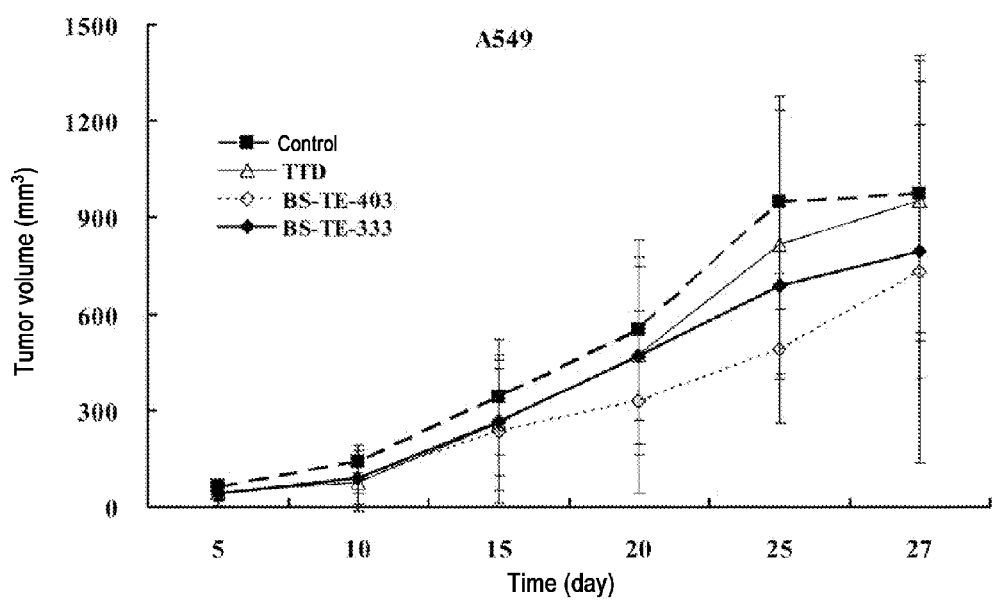
FIG. 2: the dynamic curves showing the effect of BS-TE-403 and BS-TE-333 on transplanted tumors of human lung cancer in nude mice.

FIG. 2 shows the dynamic curves illustrating the effect of BS-TE-403 and BS-TE-333 on transplanted tumor of human lung cancer in nude mice. As is shown in FIG. 2, BS-TE-403 and BS-TE-333 exhibit inhibiting effects on transplanted tumor of human lung cancer in nude mice.

Figure 3:
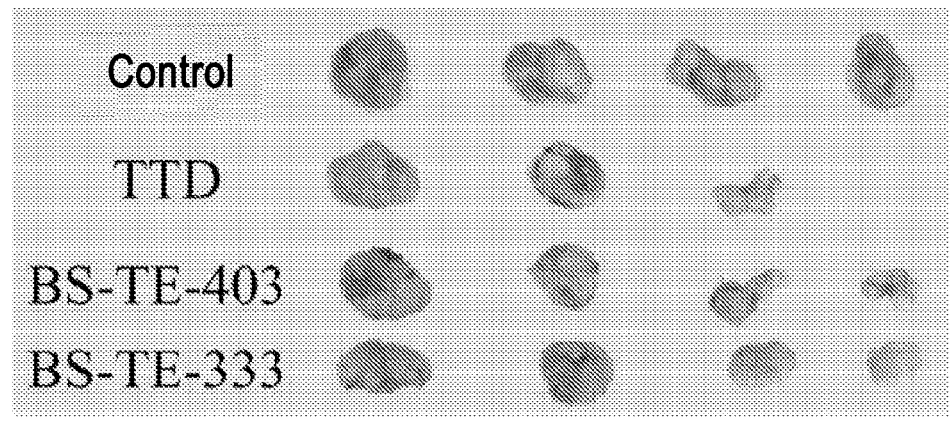
FIG. 3: photos showing the transplanted tumor of human lung cancer in nude mice administered with BS-TE-403 and BS-TE-333.
Figure 4:
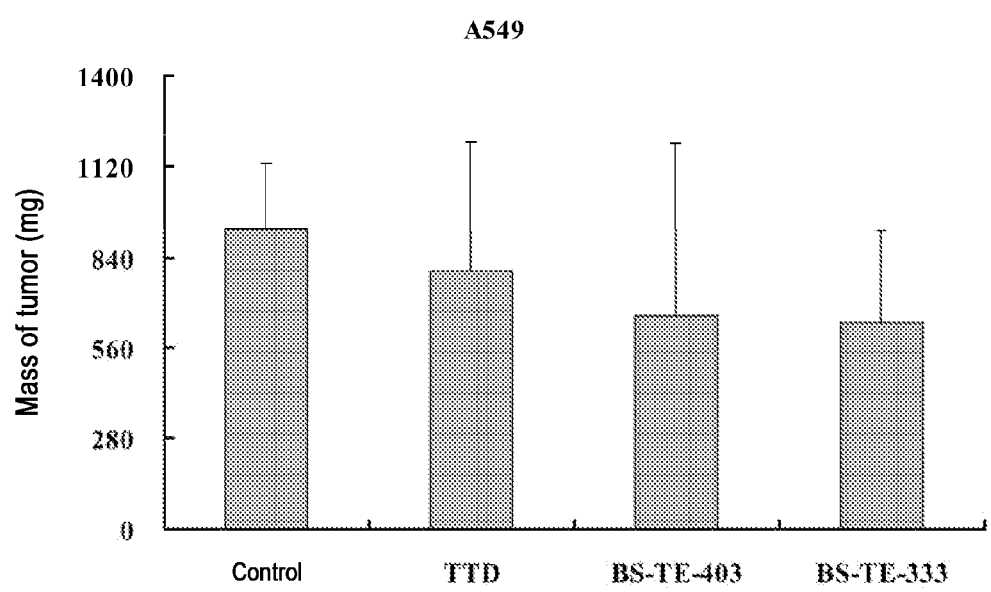
FIG. 4: the effect of BS-TE-403 and BS-TE-333 on the weight of transplanted tumors of human lung cancer in nude mice.
Figure 5:
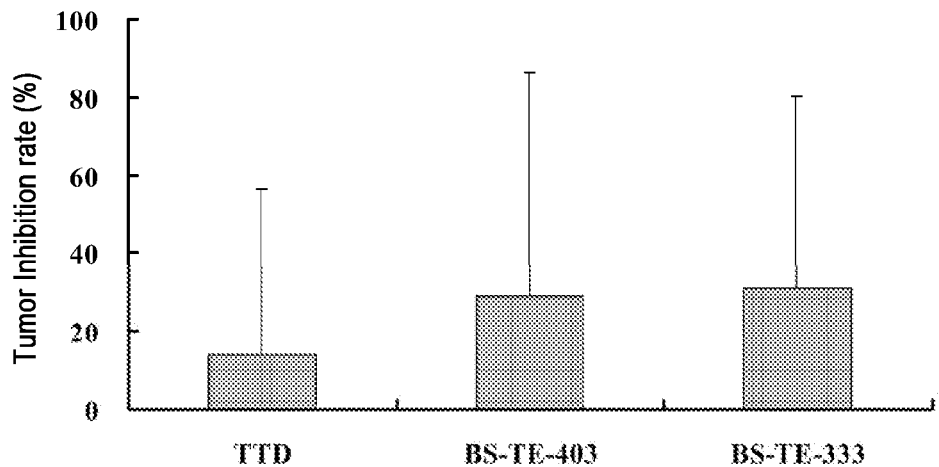
FIG. 5: the inhibiting effect of BS-TE-403 and BS-TE-333 on the transplanted tumors of human lung cancer in nude mice.

FIG. 3 shows pictures of the transplanted tumor of human lung cancer in nude mice. FIG. 4 shows the effect of BS-TE-403 and BS-TE-333 on the weight of the transplanted tumor of human lung cancer in nude mice. FIG. 5 shows the inhibiting effect of BS-TE-403 and BS-TE-333 on the transplanted tumor of human lung cancer in nude mice.

As is shown in the above tables and figures, in the in vivo experiments, the inhibition rate of BS-TE-403 on the transplanted tumor of human lung cancer in nude mice is 29.08%; the inhibition rate of BS-TE-333 on the transplanted tumor of human lung cancer in nude mice is 31.15%; and BS-TE-403 and BS-TE-333 exhibit inhibiting effect on the transplanted tumor of human lung cancer in nude mice.

Experiment 8-2

The inhibiting effect of BS-TE-354 on the transplanted tumor of human lung cancer in nude mice.
(1) Experimental Materials
  Cell lines: human non-small cell lung cancer cell line A549, from China Center for Type Culture Collection (CCTCC);
  Animal: BALB/c nude mice, 8 weeks, female, purchased from Shanghai Laboratory Animal Center of Chinese Academy of Sciences, China.
(2) Reagents:
  BS-TE-354 (the present invention), administered at a dosage of 50 mg/kg weight each time.
(3) Main Apparatuses:
  a cell incubator (Thermo Scientific $CO_2$ incubator, Type 3111), a biosafety cabinet (Heal Force, Hfsafe-1200A2) and a laminar flow rack (Suhang Brand clean animal breeding cabinet, Type DJ-2).

(4) Experimental Method

Under sterile conditions, the above tumor cells in the logarithmic growth phase are collected and injected by subcutaneous injection in an amount of $1.3 \times 10^7/0.2$ ml/nude mice (cell viability>95%) into the right subaxillary of the nude mice, thus establishing a transplanted tumor model of human non-small cell lung in nude mice.

The experiments are divided into 3 groups: negative control group (solvent group), positive control group (gefitinib, Jef) and BS-TE-354 group.

The mice are administered from the third day after the inoculation. Each mouse is intragastrically administered in 0.4 ml each time and 3 times a day, at 8:00, 14:00 and 20:00, with 6-hour intervals. The administrations are successive for 10 days. The day before administration is deemed as Day 0 and the body weight and tumor size are determined every 5 days to produce a dynamic plot on body weight and tumor growth. On Day 29, the mice are dissected and the tumors are taken out and weighted. The tumor inhibition rate (%) is calculated after the effect of the medicament based on the tumor inhibition rate of the control group being zero.

The values determined are presented as mean±standard error (M±SD).

TABLE 4

The effect of BS-TE-354 on transplanted tumors of human lung cancer in the nude mice

| Group | Dosage (mg/kg) weight/time | Number of animals Initial | Number of animals Final | Weight (g) Initial | Weight (g) Final | Mass of tumor (mg) | Tumor Inhibition rate (%) |
|---|---|---|---|---|---|---|---|
| Control | | 4 | 4 | 22.28 ± 0.33 | 20.60 ± 0.88 | 750.50 ± 397.49 | — |
| Jef | 50 | 3 | 3 | 22.1 ± 0.17 | 21.8 ± 0.99 | 883 ± 273.32 | −17.65 |
| BS-TE-354 | 50 | 4 | 4 | 22.25 ± 0.29 | 16.08 ± 1.00 | 423.25 ± 364.28 | 43.60 |

Figure 6:
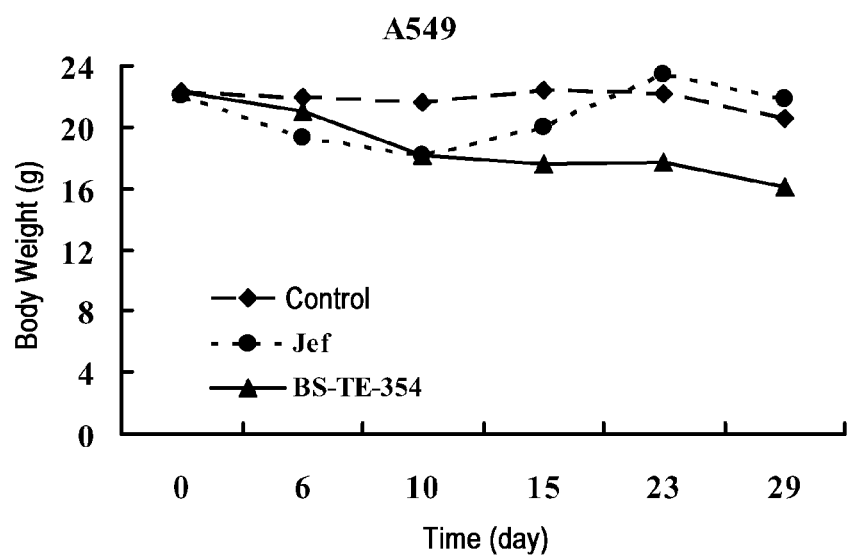
FIG. 6: the dynamic change of the effect of BS-TE-354 on the body weight of nude mice.

FIG. 6 shows the dynamic change of the effect of BS-TE-354 on the body weight of nude mice. As is shown in FIG. 6, the weight loss is relatively remarkable in the BS-TE-354 group as compared with the weight in the control group, indicating that BS-TE-354 has caused some toxic and side effect under such a dosage.

Figure 7:
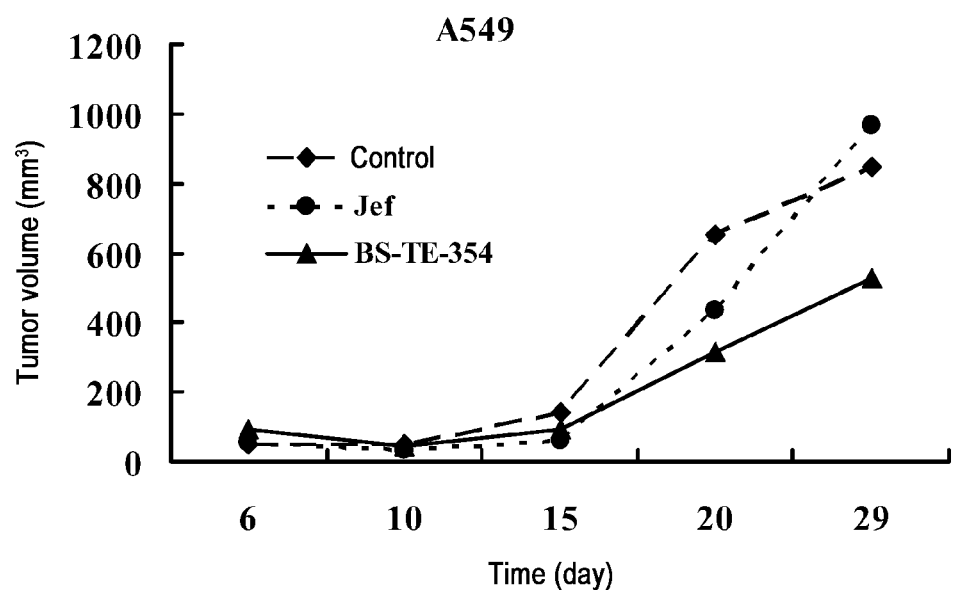
FIG. 7: the dynamic curves of the effect of BS-TE-354 on transplanted tumors of human lung cancer in nude mice.
Figure 8:
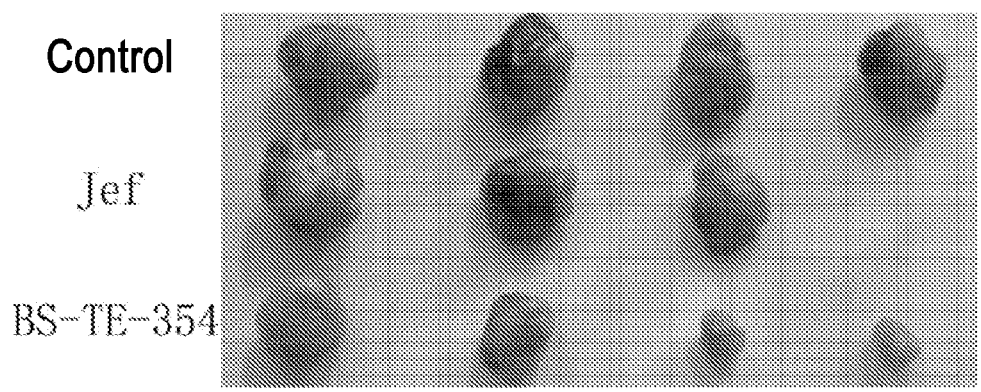
FIG. 8: photos showing the transplanted tumors of human lung cancer in nude mice administered with BS-TE-354.
Figure 9:
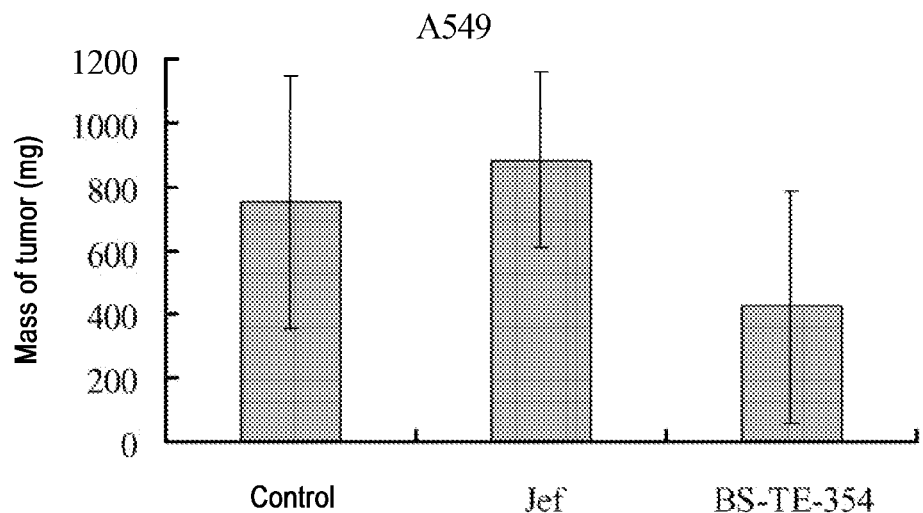
FIG. 9: the effect of BS-TE-354 on the weight of the transplanted tumors of human lung cancer in nude mice.
Figure 10:
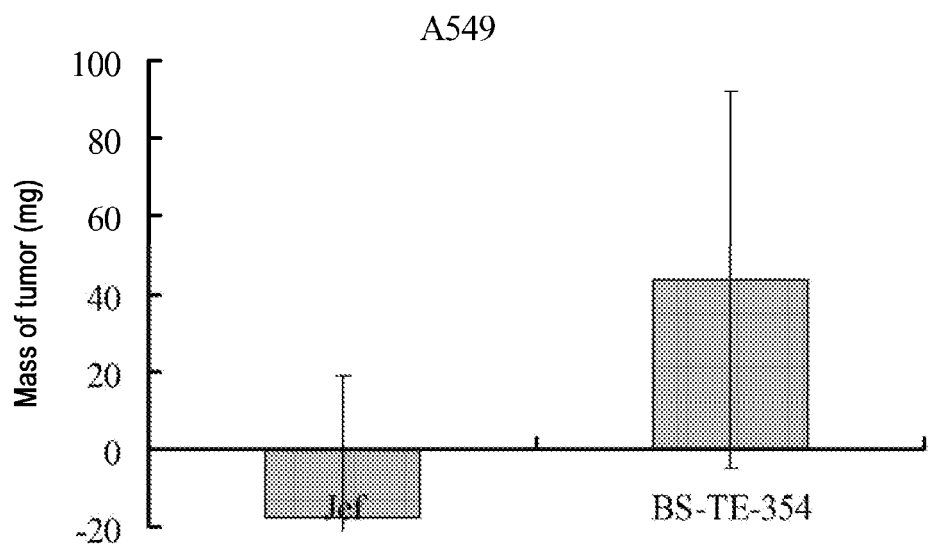
FIG. 10: the inhibiting effect of BS-TE-354 on the transplanted tumors of human lung cancer in nude mice.

FIG. 7 shows the dynamic curves of the effect of BS-TE-354 on transplanted tumor of human lung cancer in nude mice. FIG. 8 shows a picture of the transplanted tumor of human lung cancer in nude mice. FIG. 9 shows the effect of BS-TE-354 on the weight of the transplanted tumor of human lung cancer in nude mice. FIG. 10 shows the inhibiting effect of BS-TE-354 on the transplanted tumors of human lung cancer in nude mice.

As is shown in the above tables and figures, in the in vivo experiments, the inhibition rate of BS-TE-354 on the human lung cancer transplanted tumor in nude mice is 43.60%. BS-TE-354 exhibits inhibiting effect on the transplanted tumor of human lung cancer in nude mice.

The invention claimed is:

1. A compound of formula (I),

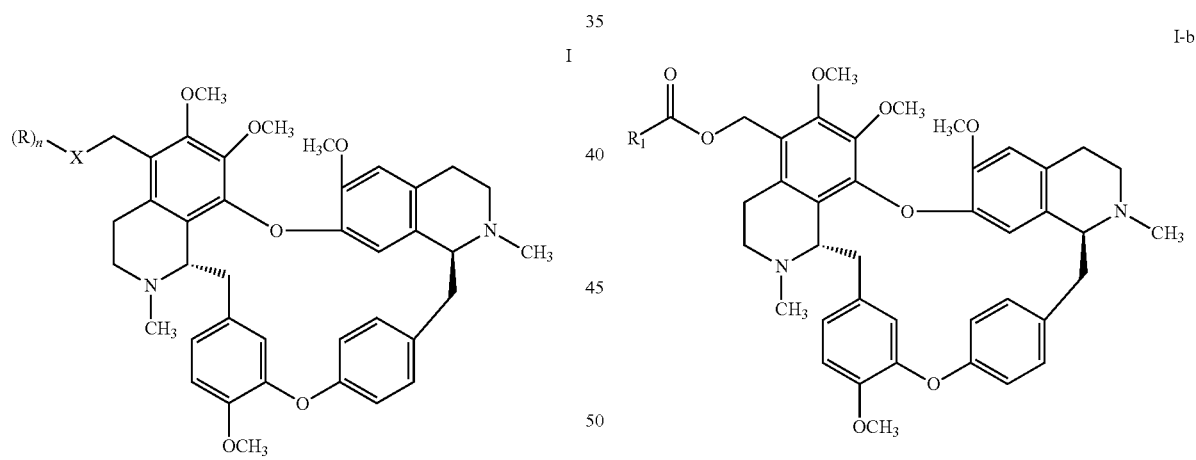

wherein

X is selected from oxygen, sulfur, nitrogen and carbonyloxy;

n is 1 or 2, wherein n=1 when X is oxygen or sulfur, and n=2 when X is nitrogen;

R is independently selected from H, $C_1$-$C_6$ alkyl, $C_3$-$C_7$ cycloalkyl or cycloalkenyl, aryl or $C_3$-$C_{10}$ heteroaryl, aryl-$C_1$-$C_3$ alkyl, $C_3$-$C_{10}$ heteroaryl-$C_1$-$C_3$ alkyl, aryloxy-$C_1$-$C_3$ alkyl and $C_3$-$C_{10}$ heteroaryloxy-$C_1$-$C_3$ alkyl; when X is carbonyloxy, R can also be $C_1$-$C_6$ alkoxy or $C_1$-$C_6$ alkyl-SH; when X is nitrogen, the two R groups together with the nitrogen atom to which they are connected can form non-aromatic nitrogen-containing $C_3$-$C_{10}$ heterocyclyl or nitrogen-containing $C_3$-$C_{10}$ heteroaryl; wherein the R groups, except for H, are optionally substituted with a substituent selected from the group consisting of halogen, amino, $C_1$-$C_6$ alkyl amino, nitro, cyano, hydroxyl, $C_1$-$C_6$ alkoxy, —SH and $C_1$-$C_6$ alkyl-SH; said cycloalkyl, cycloalkenyl, aryl, $C_3$-$C_{10}$ heteroaryl, nitrogen-containing $C_3$-$C_{10}$ heterocyclyl or nitrogen-containing $C_3$-$C_{10}$ heteroaryl are optionally substituted with a substituent selected from $C_1$-$C_6$ alkyl, hydroxyl $C_1$-$C_6$ alkyl, $C_1$-$C_6$ alkyl-SH and phenyl; wherein said $C_3$-$C_{10}$ heteroaryl, $C_3$-$C_{10}$ heteroaryloxy, and $C_3$-$C_{10}$ heterocyclyl rings are monocyclic or bicyclic, and contain 1-4 heteroatoms selected from nitrogen, oxygen, or sulfur;

or a pharmaceutically acceptable salt thereof.

2. The compound or a pharmaceutically acceptable salt thereof according to claim 1, wherein X is carbonyloxy, and the compound of formula (I) is represented by formula (I-b)

wherein $R_1$ is selected from H, $C_1$-$C_6$ alkyl, aryl or $C_3$-$C_{10}$ heteroaryl, $C_1$-$C_6$ alkoxy and $C_1$-$C_6$ alkyl-SH; wherein $R_1$, except for H, is optionally substituted with a substituent selected from the group consisting of halogen, amino, $C_1$-$C_6$ alkyl amino, nitro, cyano, hydroxyl, $C_1$-$C_6$ alkoxy, SH and $C_1$-$C_6$ alkyl-SH; said aryl and $C_3$-$C_{10}$ heteroaryl are optionally substituted with a substituent selected from $C_1$-$C_6$ alkyl, hydroxyl $C_1$-$C_6$ alkyl and $C_1$-$C_6$ alkyl-SH.

3. The compound or a pharmaceutically acceptable salt thereof according to claim 1, wherein X is nitrogen, and the compound of formula (I) is represented by formula (I-c)

I-c

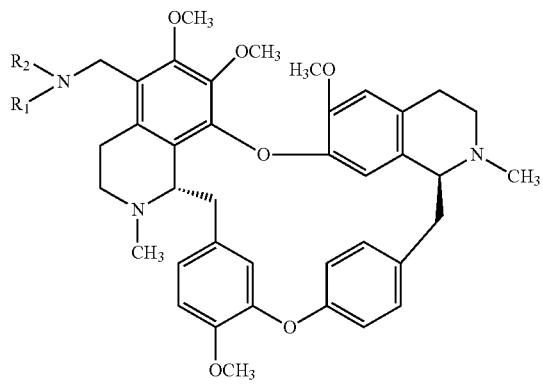

wherein $R_1$ and $R_2$ are independently selected from H, $C_1$-$C_6$ alkyl, $C_3$-$C_7$ cycloalkyl or cycloalkenyl, aryl-$C_1$-$C_3$ alkyl, $C_3$-$C_{10}$ heteroaryl-$C_1$-$C_3$ alkyl, aryloxy-$C_1$-$C_3$ alkyl and $C_3$-$C_{10}$ heteroaryloxy-$C_1$-$C_3$ alkyl, or $R_1$ and $R_2$ together with the nitrogen atom to which they are connected form non-aromatic nitrogen-containing $C_3$-$C_{10}$ heterocyclyl or nitrogen-containing $C_3$-$C_{10}$ heteroaryl; wherein $R_1$, $R_2$, the non-aromatic nitrogen-containing $C_3$-$C_{10}$ heterocyclyl or nitrogen-containing $C_3$-$C_{10}$ heteroaryl, except for H, are optionally substituted with a substituent selected from the group consisting of halogen, amino, $C_1$-$C_6$ alkyl amino, nitro, cyano, hydroxyl, $C_1$-$C_6$ alkoxy, —SH and $C_1$-$C_6$ alkyl-SH; said cycloalkyl, cycloalkenyl, aryl, $C_3$-$C_{10}$ heteroaryl, nitrogen-containing $C_3$-$C_{10}$ heterocyclyl or nitrogen-containing $C_3$-$C_{10}$ heteroaryl are optionally substituted with a substituent selected from $C_1$-$C_6$ alkyl, hydroxyl $C_1$-$C_6$ alkyl, $C_1$-$C_6$ alkyl-SH and phenyl.

4. The compound or a pharmaceutically acceptable salt thereof according to claim 1, wherein X is oxygen or sulfur, and the compound of formula (I) is represented by formula (I-d) or (I-e), I-d

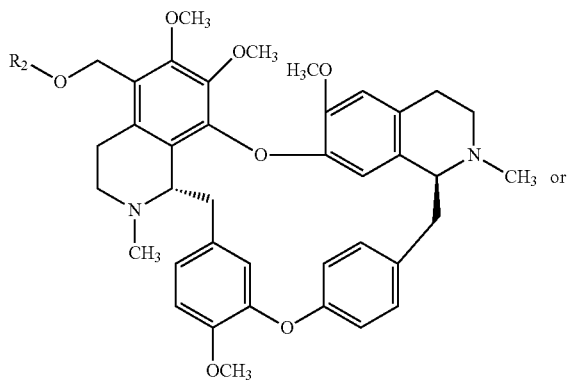

or

I-e

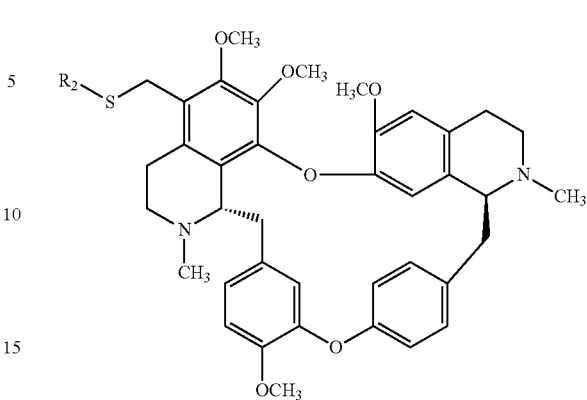

wherein $R_2$ is selected from $C_1$-$C_6$ alkyl, aryl, $C_3$-$C_7$ cycloalkyl or cycloalkenyl, aryl-$C_1$-$C_3$ alkyl, $C_3$-$C_{10}$ heteroaryl-$C_1$-$C_3$ alkyl, heterocyclic-$C_1$-$C_3$ alkyl, aryloxy-$C_1$-$C_3$ alkyl, and $C_3$-$C_{10}$ heteroaryloxy-$C_1$-$C_3$ alkyl, which are optionally substituted with a substituent selected from the group consisting of halogen, amino, $C_1$-$C_6$ alkyl amino, nitro, cyano, hydroxyl, $C_1$-$C_6$ alkoxy, —SH and $C_1$-$C_6$ alkyl-SH; said cycloalkyl, cycloalkenyl, aryl and $C_3$-$C_{10}$ heteroaryl are optionally substituted with substituents selected from $C_1$-$C_6$ alkyl, hydroxyl $C_1$-$C_6$ alkyl and $C_1$-$C_6$ alkyl-SH.

5. The compound or a pharmaceutically acceptable salt thereof according to claim 2, wherein $R_1$ is selected from $C_1$-$C_6$ alkyl, aryl and $C_3$-$C_{10}$ heteroaryl.

6. The compound or a pharmaceutically acceptable salt thereof according to claim 5, wherein $R_1$ is selected from methyl, ethyl, propyl, isopropyl, phenyl, dimethylaminophenyl, furanyl, thienyl and methylthienyl.

7. The compound or a pharmaceutically acceptable salt thereof according to claim 3, wherein $R_1$ and $R_2$ are independently selected from H, $C_1$-$C_6$ alkyl, $C_3$-$C_7$ cycloalkyl, aryl-$C_1$-$C_3$ alkyl and $C_3$-$C_{10}$ heteroaryl-$C_1$-$C_3$ alkyl, or $R_1$ and $R_2$ together with the nitrogen atom to which they are connected form non-aromatic nitrogen-containing $C_3$-$C_{10}$ heterocyclyl or nitrogen-containing $C_3$-$C_{10}$ heteroaryl.

8. The compound or a pharmaceutically acceptable salt thereof according to claim 3, wherein wherein $R_1$, $R_2$, the non-aromatic nitrogen-containing $C_3$-$C_{10}$ heterocyclyl or nitrogen-containing $C_3$-$C_{10}$ heteroaryl, except for H, are substituted with a substituent selected from the group consisting of amino, $C_1$-$C_6$ alkyl amino, nitro, cyano, hydroxyl and $C_1$-$C_6$ alkoxy; said cycloalkyl, cycloalkenyl, aryl, $C_3$-$C_{10}$ heteroaryl, nitrogen-containing $C_3$-$C_{10}$ heterocyclyl or nitrogen-containing $C_3$-$C_{10}$ heteroaryl are substituted with a substituent selected from $C_1$-$C_6$ alkyl, hydroxyl $C_1$-$C_6$ alkyl and phenyl.

9. The compound or a pharmaceutically acceptable salt thereof according to claim 8, wherein $R_1$ and $R_2$ are independently selected from H, $C_1$-$C_6$ alkyl optionally substituted with hydroxyl or $C_1$-$C_6$ alkoxy, $C_3$-$C_7$ cycloalkyl optionally substituted with hydroxyl or $C_1$-$C_6$ alkoxy, aryl-$C_1$-$C_3$ alkyl optionally substituted on the aryl with $C_1$-$C_6$ alkyl, $C_3$-$C_{10}$ heteroaryl-$C_1$-$C_3$ alkyl optionally substituted on the $C_3$-$C_{10}$ heteroaryl with $C_1$-$C_6$ alkyl, or $R_1$ and $R_2$ together with the nitrogen atom to which they are connected form non-aromatic nitrogen-containing $C_3$-$C_{10}$ heterocyclyl or nitrogen-containing $C_3$-$C_{10}$ heteroaryl; said non-aromatic nitrogen-containing $C_3$-$C_{10}$ heterocyclyl is optionally substituted with a substituent selected from hydroxyl, hydroxyl $C_1$-$C_6$ alkyl, amino, $C_1$-$C_6$ alkyl amino, $C_1$-$C_6$ alkyl, cyano, nitro and phenyl.

10. The compound or a pharmaceutically acceptable salt thereof according to claim 9, wherein $R_1$ and $R_2$ are independently selected from H, $C_1$-$C_3$ alkyl substituted with $C_1$-$C_3$ alkoxy, $C_3$-$C_6$ cycloalkyl, arylmethyl, aryl(methyl)methyl and $C_3$-$C_{10}$ heteroarylmethyl, or $R_1$ and $R_2$ together with the nitrogen atom to which they are connected form non-aromatic nitrogen-containing $C_3$-$C_{10}$ heterocyclyl; said non-aromatic nitrogen-containing $C_3$-$C_{10}$ heterocyclyl is optionally substituted with a substituent selected from hydroxyl, hydroxyl $C_1$-$C_6$ alkyl, amino, $C_1$-$C_6$ alkyl amino, $C_1$-$C_6$ alkyl, cyano, nitro and phenyl.

11. The compound or a pharmaceutically acceptable salt thereof according to claim 3, wherein said non-aromatic nitrogen-containing $C_3$-$C_{10}$ heterocyclyl is a 5-7 membered ring, optionally comprising 1-2 heteroatoms selected from nitrogen, oxygen and sulfur in addition to the nitrogen atom connecting to $R_1$ and $R_2$; said non-aromatic nitrogen-containing $C_3$-$C_{10}$ heterocyclyl is preferably pyrrolidinyl, pyrrolinyl, piperidyl, piperazinyl, morpholinyl, thiomorpholinyl or diazacycloheptyl.

12. The compound or a pharmaceutically acceptable salt thereof according to claim 3, wherein the aryl in the said aryl-containing radicals is preferably phenyl; the $C_3$-$C_{10}$ heteroaryl in the said $C_3$-$C_{10}$ heteroaryl-containing radicals is preferably a pyridyl optionally substituted with $C_1$-$C_3$ alkyl, an furyl optionally substituted with $C_1$-$C_3$ alkyl, or a thienyl optionally substituted with $C_1$-$C_3$ alkyl.

13. The compound or a pharmaceutically acceptable salt thereof according to claim 4, wherein $R_2$ is selected from aryl-$C_1$-$C_3$ alkyl, $C_3$-$C_{10}$ heteroaryl-$C_1$-$C_3$ alkyl, aryloxy-$C_1$-$C_3$ alkyl and $C_3$-$C_{10}$ heteroaryloxy-$C_1$-$C_3$ alkyl.

14. The compound or a pharmaceutically acceptable salt thereof according to claim 4, wherein the aryl in the said aryl-containing radicals or the $C_3$-$C_{10}$ heteroaryl in the said $C_3$-$C_{10}$ heteroaryl-containing radicals is substituted with a substituent selected from halogen and $C_1$-$C_6$ alkoxy; the aryl in the said aryl-containing radicals is preferably phenyl; the $C_3$-$C_{10}$ heteroaryl in the said $C_3$-$C_{10}$ heteroaryl-containing radicals is preferably pyridyl, imidazolyl or thienyl.

15. The compound or a pharmaceutically acceptable salt thereof according to claim 1, selected from the following compounds:

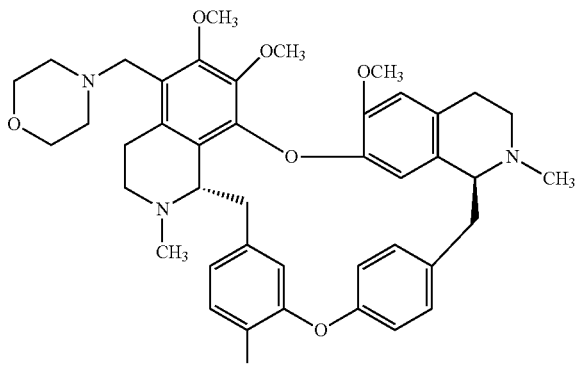

5-(morpholinyl-methyl)-tetrandrine

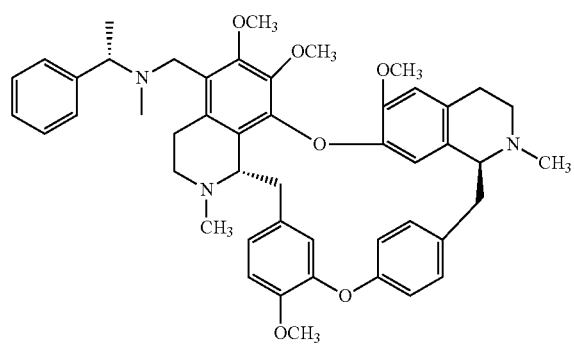

5-[(R)-N-methyl-phenylethyl-aminomethyl]-tetrandrine

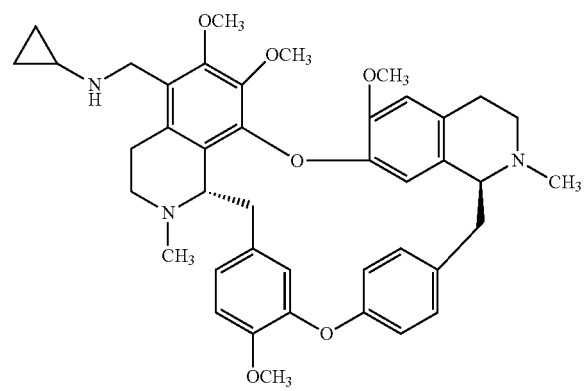

5-(cyclopropyl-amino-methyl)-tetrandrine

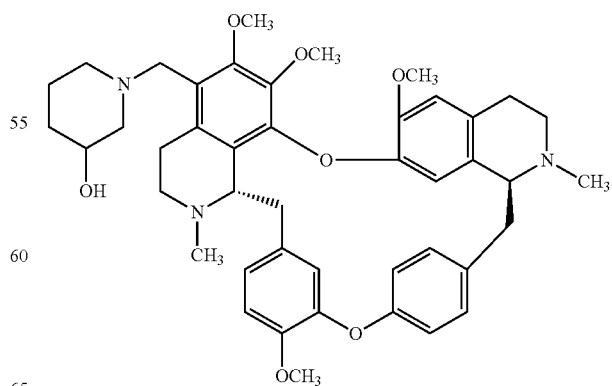

5-(m-hydroxypiperidinyl-methyl)-tetrandrine

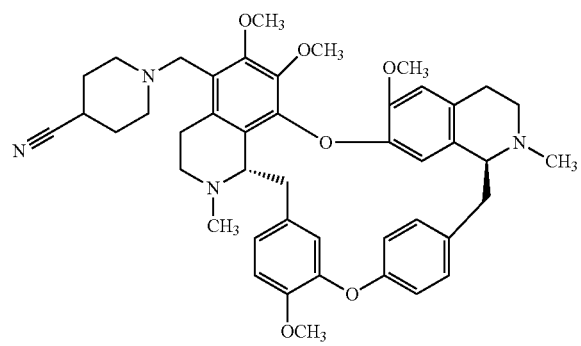
5-(p-cyanopiperidinylmethyl)-tetrandrine
BS-TE-323
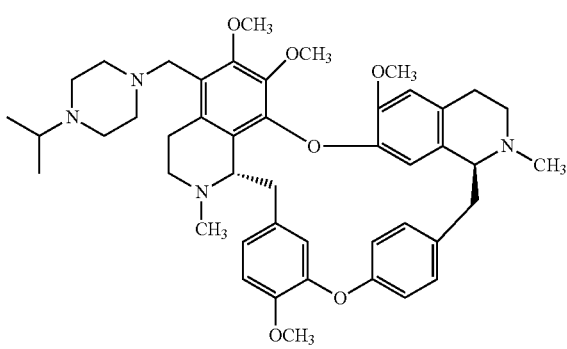
5-(N-isopropylpiperazinyl-methyl)-tetrandrine
BS-TE-333
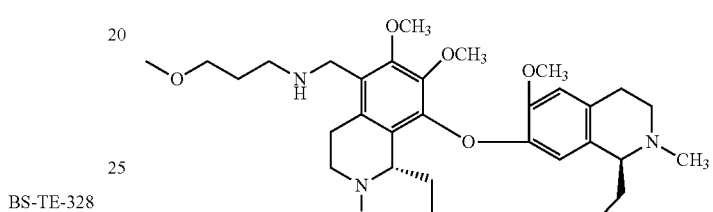
5-(methoxy-propylamino-methyl)-tetrandrine
BS-TE-340
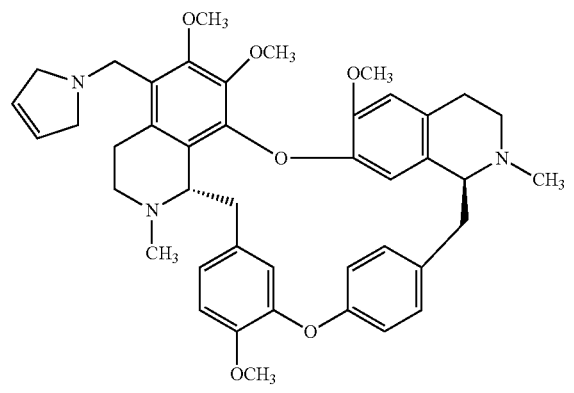
5-(thiomorpholinyl-methyl)-tetrandrine
BS-TE-328
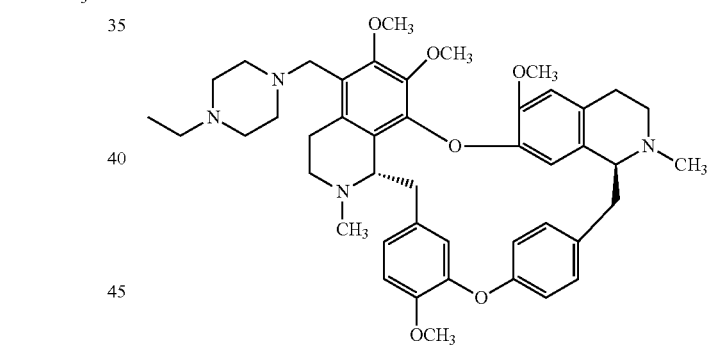
5-(N-ethylpiperazinyl-methyl)-tetrandrine
BS-TE-342
5-(2,5-dihydropyrrolyl-methyl)-tetrandrine
BS-TE-329
5-(m-methylpiperidinyl-methyl)-tetrandrine
BS-TE-346

BS-TE-350

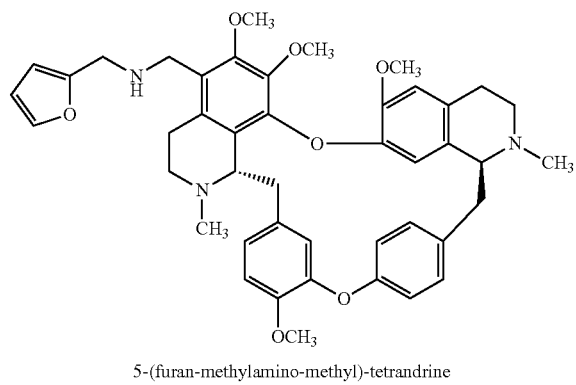

5-(furan-methylamino-methyl)-tetrandrine

BS-TE-354

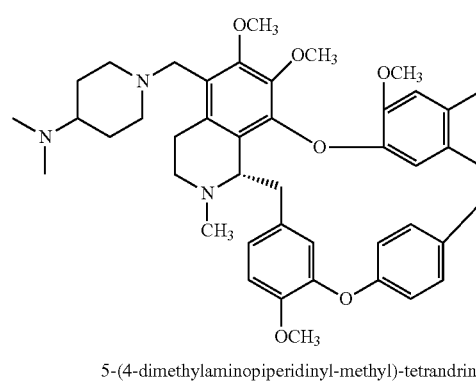

5-(4-dimethylaminopiperidinyl-methyl)-tetrandrine

BS-TE-355

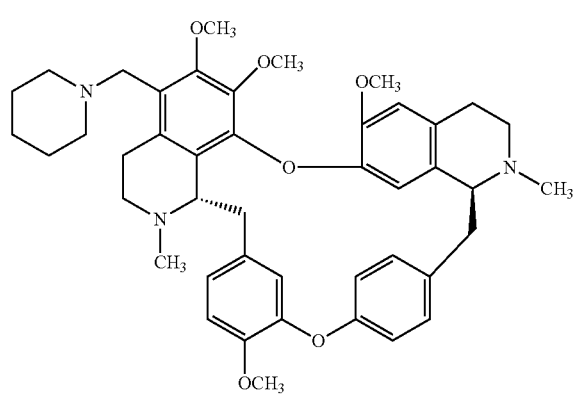

5-(piperidyl-methyl)-tetrandrine

BS-TE-359

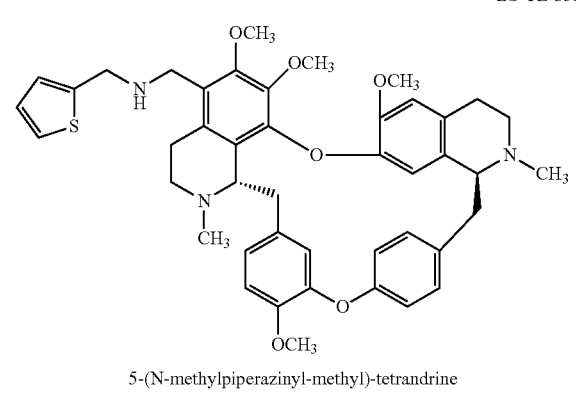

5-(N-methylpiperazinyl-methyl)-tetrandrine

BS-TE-360

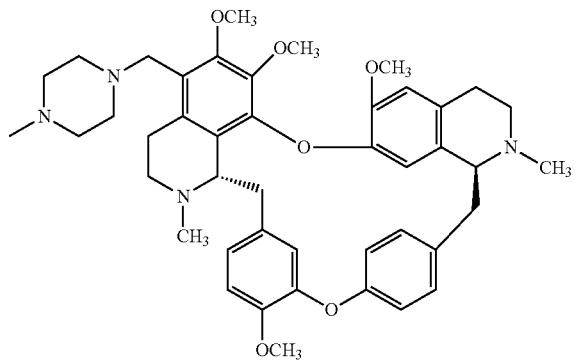

5-(N-methylpiperazinyl-methyl)-tetrandrine

BS-TE-402

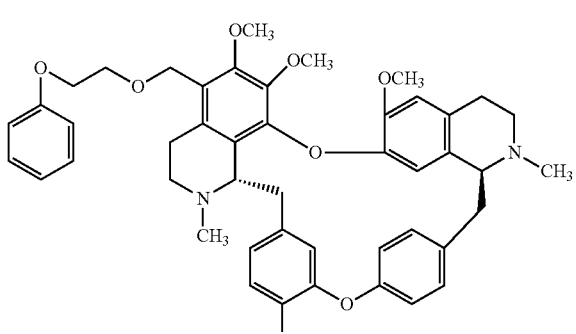

5-(phenoxy-ethoxy-methyl)-tetrandrine

BS-TE-403

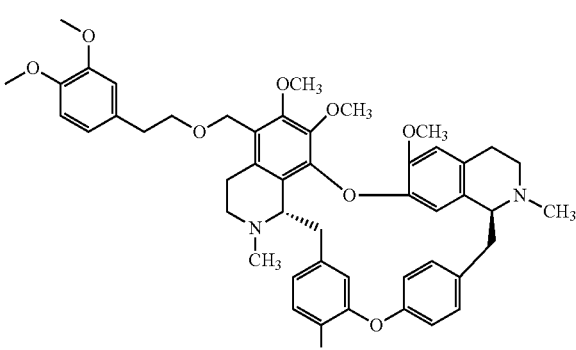

5-(3,4-dimethoxy-phenylethoxy-methyl)-tetrandrine

BS-TE-408

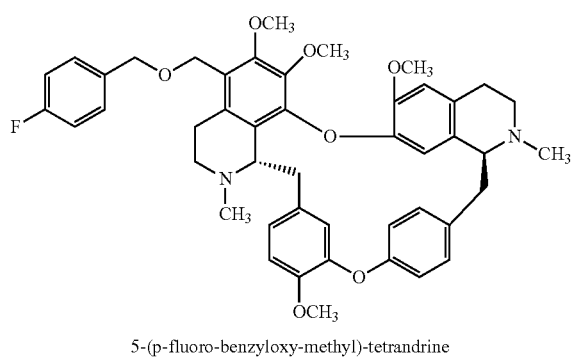

5-(p-fluoro-benzyloxy-methyl)-tetrandrine

-continued

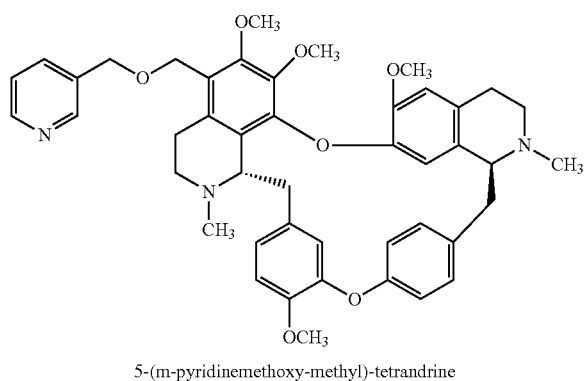

5-(m-pyridinemethoxy-methyl)-tetrandrine
BS-TE-411

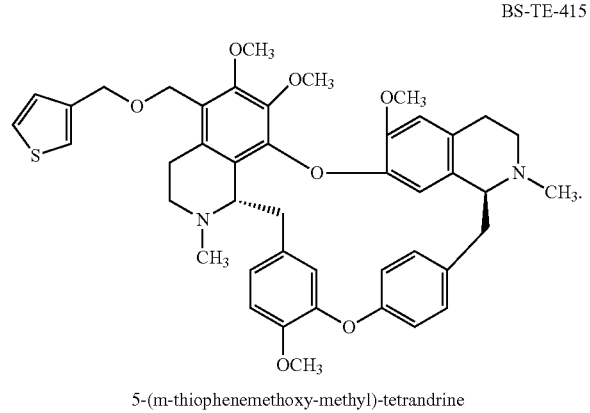

5-(m-thiophenemethoxy-methyl)-tetrandrine
BS-TE-415

16. A process for preparing the compound of formula (I) according to claim 1, comprising subjecting tetrandrine,

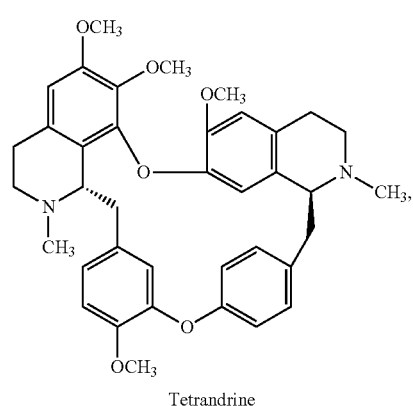 [SMILES: COc1ccc2cc1Oc1ccc(cc1)C[C@H]1c3cc(c(OC)cc3CCN1C)Oc1c(OC)c(OC)cc3c1[C@H](C2)N(C)CC3]

Tetrandrine and formaldehyde to Blanc Reaction of chloromethylation in the presence of hydrochloric acid and zinc chloride to produce 5-chloromethyltetrandrine (I-a, X=Cl),

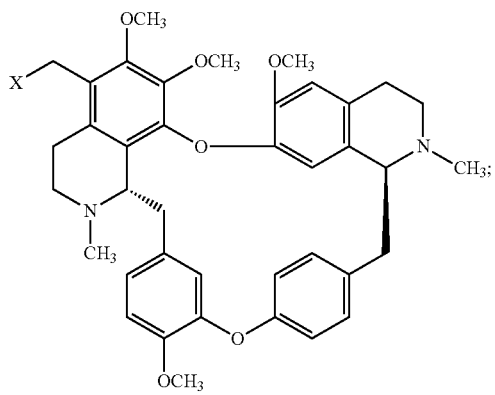

I-a and subjecting 5-chloromethyltetrandrine (I-a, X=Cl) to esterification, amination or etherification reaction to produce a compound of formula (I),

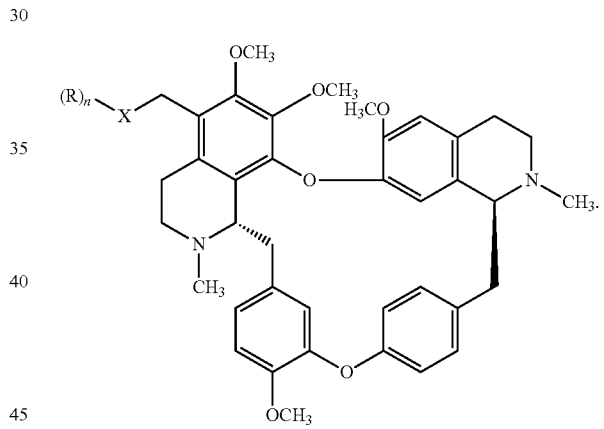

I

17. A pharmaceutical composition, comprising the compound or a pharmaceutically acceptable salt thereof according to claim 1 and a pharmaceutically acceptable excipient.

18. A method of treating cancer in a subject in need thereof, comprising administrating to the subject an effective amount of the compound or a pharmaceutically acceptable salt thereof according to claim 1, wherein the cancer is selected from the group consisting of leukemia, multiple myeloma, lymphoma, liver cancer, gastric cancer, breast cancer, cholangiocellular carcinoma, pancreatic cancer, lung cancer colorectal cancer osteosarcoma human cervical cancer, glioma, nasopharyngeal carcinoma, laryngeal carcinoma, esophageal cancer, middle ear tumor, melanoma and prostate cancer.

19. A compound of formula (I-a) or a salt thereof,

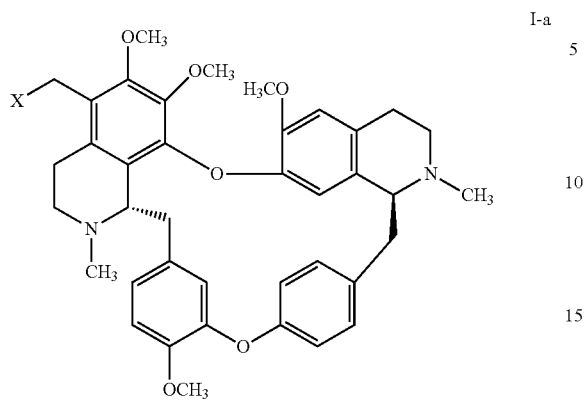

wherein X is selected from hydroxyl, SH, amino and halogen.

20. The method of claim 18, wherein the leukemia is selected from the group consisting of chronic myeloid leukemia, acute promyelocytic leukemia, acute myeloid leukemia, and acute lymphoblastic leukemia.

21. The method of claim 18, wherein the lung cancer is non-small cell lung cancer.

* * * * *